(12) United States Patent
Condeelis et al.

(10) Patent No.: US 9,970,057 B2
(45) Date of Patent: May 15, 2018

(54) HUMAN INVASION SIGNATURE FOR PROGNOSIS OF METASTATIC RISK

(75) Inventors: John Condeelis, Bronx, NY (US); Antonia Patsialou, Pelham, NY (US)

(73) Assignee: ALBERT EINSTEIN COLLEGE OF MEDICINE, INC., Bronx, NY (US)

( * ) Notice: Subject to any disclaimer, the term of this patent is extended or adjusted under 35 U.S.C. 154(b) by 0 days. days.

(21) Appl. No.: 14/115,928

(22) PCT Filed: May 4, 2012

(86) PCT No.: PCT/US2012/036544
§ 371 (c)(1),
(2), (4) Date: Dec. 20, 2013

(87) PCT Pub. No.: WO2012/154567
PCT Pub. Date: Nov. 15, 2012

(65) Prior Publication Data
US 2014/0314786 A1    Oct. 23, 2014

Related U.S. Application Data

(60) Provisional application No. 61/483,345, filed on May 6, 2011.

(51) Int. Cl.
*C12Q 1/68* (2018.01)

(52) U.S. Cl.
CPC ...... *C12Q 1/6886* (2013.01); *C12Q 2600/112* (2013.01); *C12Q 2600/158* (2013.01); *C12Q 2600/16* (2013.01)

(58) Field of Classification Search
CPC ............ C12Q 1/6886; C12Q 2600/112; C12Q 2600/158
See application file for complete search history.

(56) References Cited

U.S. PATENT DOCUMENTS

| 2007/0105133 A1 | 5/2007 | Clarke et al. |
| 2010/0047235 A1 | 2/2010 | Gorman et al. |

FOREIGN PATENT DOCUMENTS

| WO | 2008079263 A2 | 7/2008 |
| WO | 2008079269 A2 | 7/2008 |
| WO | 2010040571 A2 | 4/2010 |
| WO | 2010089443 A2 | 8/2010 |
| WO | 2010121212 A2 | 10/2010 |

OTHER PUBLICATIONS

Weigelt, B. et al. Nature Reviews—Cancer 5:591 (Aug. 2005).*
PCT International Search Report dated Jan. 23, 2014 in connection with PCT International Patent Application No. PCT/US2012/036544, 6 pages.
PCT Written Opinion of the International Searching Authority dated Jan. 23, 2014 in connection with PCT International Patent Application No. PCT/US2012/036544, 9 pages.

* cited by examiner

*Primary Examiner* — Diana B Johannsen
(74) *Attorney, Agent, or Firm* — Amster, Rothstein & Ebenstein LLP

(57) ABSTRACT

Methods and products are provided for determining if a subject having a tumor is (i) at risk of metastasis of the tumor, or (ii) at risk of recurrence of the tumor after treatment of the tumor. Methods of treatment of cancer, tumors and metastasis are also provided.

6 Claims, 13 Drawing Sheets

SEQUENCE LISTING

<160> NUMBER OF SEQ ID NOS: 114

<210> SEQ ID NO 1
<211> LENGTH: 20
<212> TYPE: DNA
<213> ORGANISM: Artificial Sequence
<220> FEATURE:
<223> OTHER INFORMATION: PRIMER DIRECTED TO HUMAN ARHGDIB

<400> SEQUENCE: 1
ctcggcctga ggagtatgag                                        20

<210> SEQ ID NO 2
<211> LENGTH: 20
<212> TYPE: DNA
<213> ORGANISM: Artificial Sequence
<220> FEATURE:
<223> OTHER INFORMATION: PRIMER DIRECTED TO HUMAN ARHGDIB

<400> SEQUENCE: 2
gtggtcttgc ttgtcatcgt                                        20

<210> SEQ ID NO 3
<211> LENGTH: 20
<212> TYPE: DNA
<213> ORGANISM: Artificial Sequence
<220> FEATURE:
<223> OTHER INFORMATION: PRIM ER DIRECTED TO HUAMN CAV1

<400> SEQUENCE: 3
cgtctgtgac ccactctttg                                        20

<210> SEQ ID NO 4
<211> LENGTH: 20
<212> TYPE: DNA
<213> ORGANISM: Artificial Sequence
<220> FEATURE:
<223> OTHER INFORMATION: PRIMER DIRECTED TO HUMAN CAV1

<400> SEQUENCE: 4
gatgcggaca ttgctgaata                                        20

<210> SEQ ID NO 5
<211> LENGTH: 20
<212> TYPE: DNA
<213> ORGANISM: Artificial Sequence
<220> FEATURE:
<223> OTHER INFORMATION: PRIMER DIRECTED TO CDC25A

<400> SEQUENCE: 5
cccaaactcc actaccctga                                        20

<210> SEQ ID NO 6
<211> LENGTH: 20
<212> TYPE: DNA
<213> ORGANISM: Artificial Sequence
<220> FEATURE:
<223> OTHER INFORMATION: PRIMER DIRECTED TO CDC25A

<400> SEQUENCE: 6
gcggaacttc ttcaggtctt                                        20

<210> SEQ ID NO 7
<211> LENGTH: 20
<212> TYPE: DNA
<213> ORGANISM: Artificial Sequence -continued

```
<220> FEATURE:
<223> OTHER INFORMATION: PRIMER DIRECTED TO HUMAN CDC42

<400> SEQUENCE: 7
tacgaccgct gagttatcca                                              20

<210> SEQ ID NO 8
<211> LENGTH: 20
<212> TYPE: DNA
<213> ORGANISM: Artificial Sequence
<220> FEATURE:
<223> OTHER INFORMATION: PRIMER DIRECTED TO HUMAN CDC42

<400> SEQUENCE: 8
atctcaggca cccactttc                                               20

<210> SEQ ID NO 9
<211> LENGTH: 20
<212> TYPE: DNA
<213> ORGANISM: Artificial Sequence
<220> FEATURE:
<223> OTHER INFORMATION: PRIMER DIRECTED TO HUMAN DAZAP2

<400> SEQUENCE: 9
tggtggaagg agggtatgat                                              20

<210> SEQ ID NO 10
<211> LENGTH: 20
<212> TYPE: DNA
<213> ORGANISM: Artificial Sequence
<220> FEATURE:
<223> OTHER INFORMATION: PRIMER DIRECTED TO HUMAN DAZAP2

<400> SEQUENCE: 10
aggaggtgga ggaggaatgt                                              20

<210> SEQ ID NO 11
<211> LENGTH: 20
<212> TYPE: DNA
<213> ORGANISM: Artificial Sequence
<220> FEATURE:
<223> OTHER INFORMATION: PRIMER DIRECTED TO HUMAN FADD

<400> SEQUENCE: 11
gacctccaga acaggagtgg                                              20

<210> SEQ ID NO 12
<211> LENGTH: 20
<212> TYPE: DNA
<213> ORGANISM: Artificial Sequence
<220> FEATURE:
<223> OTHER INFORMATION: PRIMER DIRECTED TO HUMAN FADD

<400> SEQUENCE: 12
atgcgtctga gttccatgac                                              20

<210> SEQ ID NO 13
<211> LENGTH: 20
<212> TYPE: DNA
<213> ORGANISM: Artificial Sequence
<220> FEATURE:
<223> OTHER INFORMATION: PRIMER DIRECTED TO HUMAN FOXM1

<400> SEQUENCE: 13
tgatggatct cagcaccact                                              20
```

<210> SEQ ID NO 14
<211> LENGTH: 20
<212> TYPE: DNA
<213> ORGANISM: Artificial Sequence
<220> FEATURE:
<223> OTHER INFORMATION: PRIMER DIRECTED TO HUMAN FOXM1

<400> SEQUENCE: 14
gggacggaga tgaggtctaa                                              20

<210> SEQ ID NO 15
<211> LENGTH: 20
<212> TYPE: DNA
<213> ORGANISM: Artificial Sequence
<220> FEATURE:
<223> OTHER INFORMATION: PRIMER DIRECTED TO HUMAN IFI16

<400> SEQUENCE: 15
catggacgac tgaccacaat                                              20

<210> SEQ ID NO 16
<211> LENGTH: 20
<212> TYPE: DNA
<213> ORGANISM: Artificial Sequence
<220> FEATURE:
<223> OTHER INFORMATION: PRIMER DIRECT TO HUMAN IFI16

<400> SEQUENCE: 16
cctggtcttg atgaccttga                                              20

<210> SEQ ID NO 17
<211> LENGTH: 20
<212> TYPE: DNA
<213> ORGANISM: Artificial Sequence
<220> FEATURE:
<223> OTHER INFORMATION: PRIMER DIRECTED TO HUMAN IL8

<400> SEQUENCE: 17
ctgcgccaac acagaaatta                                              20

<210> SEQ ID NO 18
<211> LENGTH: 20
<212> TYPE: DNA
<213> ORGANISM: Artificial Sequence
<220> FEATURE:
<223> OTHER INFORMATION: PRIMER DIRECTED TO HUMAN IL8

<400> SEQUENCE: 18
acttctccac aaccctctgc                                              20

<210> SEQ ID NO 19
<211> LENGTH: 20
<212> TYPE: DNA
<213> ORGANISM: Artificial Sequence
<220> FEATURE:
<223> OTHER INFORMATION: PRIMER DIRECTED TO HUMAN KLF11

<400> SEQUENCE: 19
gccggaagac ctacttcaaa                                              20

<210> SEQ ID NO 20
<211> LENGTH: 20
<212> TYPE: DNA
<213> ORGANISM: Artificial Sequence
<220> FEATURE:
<223> OTHER INFORMATION: PRIMER DIRECTED TO HUMAN KLF11

```
<400> SEQUENCE: 20
gctgcagttg aaaggcttct                                               20

<210> SEQ ID NO 21
<211> LENGTH: 20
<212> TYPE: DNA
<213> ORGANISM: Artificial Sequence
<220> FEATURE:
<223> OTHER INFORMATION: PRIMER DIRECTED TO HUMAN MSN

<400> SEQUENCE: 21
aaggagagtg aggctgtgga                                               20

<210> SEQ ID NO 22
<211> LENGTH: 20
<212> TYPE: DNA
<213> ORGANISM: Artificial Sequence
<220> FEATURE:
<223> OTHER INFORMATION: PRIMER DIRECTED TO HUMAN MSN

<400> SEQUENCE: 22
gctctgccac atgaggtgta                                               20

<210> SEQ ID NO 23
<211> LENGTH: 20
<212> TYPE: DNA
<213> ORGANISM: Artificial Sequence
<220> FEATURE:
<223> OTHER INFORMATION: PRIMER DIRECTED TO NCL

<400> SEQUENCE: 23
ttcaacagtg aggaggatgc                                               20

<210> SEQ ID NO 24
<211> LENGTH: 20
<212> TYPE: DNA
<213> ORGANISM: Artificial Sequence
<220> FEATURE:
<223> OTHER INFORMATION: PRIMER DIRECTED TO HUMAN NCL

<400> SEQUENCE: 24
agccaccttc acccttaggt                                               20

<210> SEQ ID NO 25
<211> LENGTH: 20
<212> TYPE: DNA
<213> ORGANISM: Artificial Sequence
<220> FEATURE:
<223> OTHER INFORMATION: PRIMER DIRECTED TO HUMAN PHACTR2

<400> SEQUENCE: 25
agaggcccac aactgaagaa                                               20

<210> SEQ ID NO 26
<211> LENGTH: 20
<212> TYPE: DNA
<213> ORGANISM: Artificial Sequence
<220> FEATURE:
<223> OTHER INFORMATION: PRIMER DIRECTED TO HUMAN PHACTR2

<400> SEQUENCE: 26
ggctgagctt tctgctgagt                                               20

<210> SEQ ID NO 27
```

```
<211> LENGTH: 20
<212> TYPE: DNA
<213> ORGANISM: Artificial Sequence
<220> FEATURE:
<223> OTHER INFORMATION: PRIMER DIRECTED TO PKM2

<400> SEQUENCE: 27
gggtgaactt tgccatgaat                                               20

<210> SEQ ID NO 28
<211> LENGTH: 20
<212> TYPE: DNA
<213> ORGANISM: Artificial Sequence
<220> FEATURE:
<223> OTHER INFORMATION: PRIMER DIRECTED TO PKM2

<400> SEQUENCE: 28
tgaccacatc tcccttcttg                                               20

<210> SEQ ID NO 29
<211> LENGTH: 20
<212> TYPE: DNA
<213> ORGANISM: Artificial Sequence
<220> FEATURE:
<223> OTHER INFORMATION: PRIMER DIRECTED TO PTPNII

<400> SEQUENCE: 29
atatggcgtc atgcgtgtta                                               20

<210> SEQ ID NO 30
<211> LENGTH: 20
<212> TYPE: DNA
<213> ORGANISM: Artificial Sequence
<220> FEATURE:
<223> OTHER INFORMATION: PRIMER DIRECTED TO PTPNII

<400> SEQUENCE: 30
tccgtattcc cttgtccaac                                               20

<210> SEQ ID NO 31
<211> LENGTH: 20
<212> TYPE: DNA
<213> ORGANISM: Artificial Sequence
<220> FEATURE:
<223> OTHER INFORMATION: PRIMER DIRECTED TO HUMAN SKP1

<400> SEQUENCE: 31
accctcctcc tcctgaagat                                               20

<210> SEQ ID NO 32
<211> LENGTH: 20
<212> TYPE: DNA
<213> ORGANISM: Artificial Sequence
<220> FEATURE:
<223> OTHER INFORMATION: PRIMER DIRECTED TO HUMAN SKP1

<400> SEQUENCE: 32
cttggtccca aacagggata                                               20

<210> SEQ ID NO 33
<211> LENGTH: 20
<212> TYPE: DNA
<213> ORGANISM: Artificial Sequence
<220> FEATURE:
<223> OTHER INFORMATION: PRIMER DIRECTED TO HUMAN SMAD2

<400> SEQUENCE: 33
```
gtgcaatctt tgtgcagagc                                              20

<210> SEQ ID NO 34
<211> LENGTH: 20
<212> TYPE: DNA
<213> ORGANISM: Artificial Sequence
<220> FEATURE:
<223> OTHER INFORMATION: PRIMER DIRECTED TO HUMAN SMAD2

<400> SEQUENCE: 34
agcagcaaat tcctggttgt                                              20

<210> SEQ ID NO 35
<211> LENGTH: 20
<212> TYPE: DNA
<213> ORGANISM: Artificial Sequence
<220> FEATURE:
<223> OTHER INFORMATION: PRIMER DIRECTED TO HUMAN SNTB2

<400> SEQUENCE: 35
ctgctgagct gatcaaggaa                                              20

<210> SEQ ID NO 36
<211> LENGTH: 20
<212> TYPE: DNA
<213> ORGANISM: Artificial Sequence
<220> FEATURE:
<223> OTHER INFORMATION: PRIMER DIRECTED TO HUMAN SNTB2

<400> SEQUENCE: 36
cggtacaata tgctgctgga                                              20

<210> SEQ ID NO 37
<211> LENGTH: 20
<212> TYPE: DNA
<213> ORGANISM: Artificial Sequence
<220> FEATURE:
<223> OTHER INFORMATION: PRIMER DIRECTED TO HUMAN TUBA1A

<400> SEQUENCE: 37
ccaagcgtac catccagttt                                              20

<210> SEQ ID NO 38
<211> LENGTH: 20
<212> TYPE: DNA
<213> ORGANISM: Artificial Sequence
<220> FEATURE:
<223> OTHER INFORMATION: PRIMER DIRECTED TO HUMAN TUBA1A

<400> SEQUENCE: 38
agtgggaggc tggtagttga                                              20

<210> SEQ ID NO 39
<211> LENGTH: 20
<212> TYPE: DNA
<213> ORGANISM: Artificial Sequence
<220> FEATURE:
<223> OTHER INFORMATION: PRIMER DIRECTED TO HUMAN UBC

<400> SEQUENCE: 39
cgtgaagacc ctgactggta                                              20

<210> SEQ ID NO 40
<211> LENGTH: 20
<212> TYPE: DNA

```
<213> ORGANISM: Artificial Sequence
<220> FEATURE:
<223> OTHER INFORMATION: PRIMER DIRECTED TO HUMAN UBC

<400> SEQUENCE: 40
cttggatctt tgccttgaca                                              20

<210> SEQ ID NO 41
<211> LENGTH: 20
<212> TYPE: DNA
<213> ORGANISM: Artificial Sequence
<220> FEATURE:
<223> OTHER INFORMATION: PRIMER DIRECTED TO HUMAN VAMP7

<400> SEQUENCE: 41
gctcgagcca tgtgtatgaa                                              20

<210> SEQ ID NO 42
<211> LENGTH: 20
<212> TYPE: DNA
<213> ORGANISM: Artificial Sequence
<220> FEATURE:
<223> OTHER INFORMATION: PRIMER DIRECTED TO HUMAN VAMP7

<400> SEQUENCE: 42
tccaccacag agaggtgaaa                                              20

<210> SEQ ID NO 43
<211> LENGTH: 20
<212> TYPE: DNA
<213> ORGANISM: Artificial Sequence
<220> FEATURE:
<223> OTHER INFORMATION: PRIMER DIRECTED TO HUAMN XRCC5

<400> SEQUENCE: 43
cctgaaagcc cttcaagaga                                              20

<210> SEQ ID NO 44
<211> LENGTH: 20
<212> TYPE: DNA
<213> ORGANISM: Artificial Sequence
<220> FEATURE:
<223> OTHER INFORMATION: PRIMER DIRECTED TO HUMAN XRCC5

<400> SEQUENCE: 44
agaggcttcc tctttggtga                                              20

<210> SEQ ID NO 45
<211> LENGTH: 20
<212> TYPE: DNA
<213> ORGANISM: Artificial Sequence
<220> FEATURE:
<223> OTHER INFORMATION: PRIMER DIRECTED TO HUMAN GADPH

<400> SEQUENCE: 45
cgaccacttt gtcaagctca                                              20

<210> SEQ ID NO 46
<211> LENGTH: 20
<212> TYPE: DNA
<213> ORGANISM: Artificial Sequence
<220> FEATURE:
<223> OTHER INFORMATION: PRIMER DIRECTED TO HUMAN GAPDH

<400> SEQUENCE: 46
ccctgttgct gtagccaaat                                              20
```

<210> SEQ ID NO 47
<211> LENGTH: 20
<212> TYPE: DNA
<213> ORGANISM: Artificial Sequence
<220> FEATURE:
<223> OTHER INFORMATION: PRIMER DIRECTED TO HUMAN B2M

<400> SEQUENCE: 47
gctcgcgcta ctctctcttt                                          20

<210> SEQ ID NO 48
<211> LENGTH: 20
<212> TYPE: DNA
<213> ORGANISM: Artificial Sequence
<220> FEATURE:
<223> OTHER INFORMATION: PRIMER DIRECTED TO HUMAN B2M

<400> SEQUENCE: 48
ttcaatgtcg gatggatgaa                                          20

<210> SEQ ID NO 49
<211> LENGTH: 20
<212> TYPE: DNA
<213> ORGANISM: Artificial Sequence
<220> FEATURE:
<223> OTHER INFORMATION: PRIMER DIRECTED TO HUMAN GADPH

<400> SEQUENCE: 49
cgaccacttt gtcaagctca                                          20

<210> SEQ ID NO 50
<211> LENGTH: 20
<212> TYPE: DNA
<213> ORGANISM: Artificial Sequence
<220> FEATURE:
<223> OTHER INFORMATION: PRIMER DIRECTED TO HUMAN GADPH

<400> SEQUENCE: 50
ccctgttgct gtagccaaat                                          20

<210> SEQ ID NO 51
<211> LENGTH: 20
<212> TYPE: DNA
<213> ORGANISM: Artificial Sequence
<220> FEATURE:
<223> OTHER INFORMATION: PRIMER DIRECTED TO HUMAN B2M

<400> SEQUENCE: 51
gctcgcgcta ctctctcttt                                          20

<210> SEQ ID NO 52
<211> LENGTH: 20
<212> TYPE: DNA
<213> ORGANISM: Artificial Sequence
<220> FEATURE:
<223> OTHER INFORMATION: PRIMER DIRECTED TO HUMAN B2M

<400> SEQUENCE: 52
ttcaatgtcg gatggatgaa                                          20

<210> SEQ ID NO 53
<211> LENGTH: 20
<212> TYPE: DNA
<213> ORGANISM: Artificial Sequence
<220> FEATURE:

<223> OTHER INFORMATION: PRIMER DIRECTED TO HUMAN ARHGDIB

<400> SEQUENCE: 53
ctcggcctga ggagtatgag                                                    20

<210> SEQ ID NO 54
<211> LENGTH: 20
<212> TYPE: DNA
<213> ORGANISM: Artificial Sequence
<220> FEATURE:
<223> OTHER INFORMATION: PRIMER DIRECTED TO HUMAN ARHGDIB

<400> SEQUENCE: 54
gtggtcttgc ttgtcatcgt                                                    20

<210> SEQ ID NO 55
<211> LENGTH: 20
<212> TYPE: DNA
<213> ORGANISM: Artificial Sequence
<220> FEATURE:
<223> OTHER INFORMATION: PRIMER DIRECTED TO HUMAN CAPZA2

<400> SEQUENCE: 55
tacgtcgaca gttgccagtt                                                    20

<210> SEQ ID NO 56
<211> LENGTH: 20
<212> TYPE: DNA
<213> ORGANISM: Artificial Sequence
<220> FEATURE:
<223> OTHER INFORMATION: PRIMER DIRECTED TO HUMAN CAPZA2

<400> SEQUENCE: 56
tctgcatctc tttgccaatc                                                    20

<210> SEQ ID NO 57
<211> LENGTH: 20
<212> TYPE: DNA
<213> ORGANISM: Artificial Sequence
<220> FEATURE:
<223> OTHER INFORMATION: PRIMER DIRECTED TO HUMAN CAPZB

<400> SEQUENCE: 57
atatcgtcaa tgggctgagg                                                    20

<210> SEQ ID NO 58
<211> LENGTH: 20
<212> TYPE: DNA
<213> ORGANISM: Artificial Sequence
<220> FEATURE:
<223> OTHER INFORMATION: PRIMER DIRECTED TO HUMAN CAPZB

<400> SEQUENCE: 58
ctcttcaaag cctccaccag                                                    20

<210> SEQ ID NO 59
<211> LENGTH: 20
<212> TYPE: DNA
<213> ORGANISM: Artificial Sequence
<220> FEATURE:
<223> OTHER INFORMATION: PRIMER DIRECTED TO HUMAN SNTB2

<400> SEQUENCE: 59
ctgctgagct gatcaaggaa                                                    20

-continued

```
<210> SEQ ID NO 60
<211> LENGTH: 20
<212> TYPE: DNA
<213> ORGANISM: Artificial Sequence
<220> FEATURE:
<223> OTHER INFORMATION: PRIMER DIRECTED TO HUMAN SNTB2

<400> SEQUENCE: 60
cggtacaata tgctgctgga                                                   20

<210> SEQ ID NO 61
<211> LENGTH: 20
<212> TYPE: DNA
<213> ORGANISM: Artificial Sequence
<220> FEATURE:
<223> OTHER INFORMATION: PRIMER DIRECTED TO HUMAN PHACTR2

<400> SEQUENCE: 61
agaggcccac aactgaagaa                                                   20

<210> SEQ ID NO 62
<211> LENGTH: 20
<212> TYPE: DNA
<213> ORGANISM: Artificial Sequence
<220> FEATURE:
<223> OTHER INFORMATION: PRIMER DIRECTED TO HUMAN PHACTR2

<400> SEQUENCE: 62
ggctgagctt tctgctgagt                                                   20

<210> SEQ ID NO 63
<211> LENGTH: 20
<212> TYPE: DNA
<213> ORGANISM: Artificial Sequence
<220> FEATURE:
<223> OTHER INFORMATION: PRIMER DIRECTED TO HUMAN TUBA1A

<400> SEQUENCE: 63
ccaagcgtac catccagttt                                                   20

<210> SEQ ID NO 64
<211> LENGTH: 20
<212> TYPE: DNA
<213> ORGANISM: Artificial Sequence
<220> FEATURE:
<223> OTHER INFORMATION: PRIMER DIRECTED TO HUMAN TUBA1A

<400> SEQUENCE: 64
agtgggaggc tggtagttga                                                   20

<210> SEQ ID NO 65
<211> LENGTH: 20
<212> TYPE: DNA
<213> ORGANISM: Artificial Sequence
<220> FEATURE:
<223> OTHER INFORMATION: PRIMER DIRECTED TO HUMAN CAV1

<400> SEQUENCE: 65
cgtctgtgac ccactctttg                                                   20

<210> SEQ ID NO 66
<211> LENGTH: 20
<212> TYPE: DNA
<213> ORGANISM: Artificial Sequence
<220> FEATURE:
<223> OTHER INFORMATION: PRIMER DIRECTED TO HUMAN CAV1
```

```
<400> SEQUENCE: 66
gatgcggaca ttgctgaata                                              20

<210> SEQ ID NO 67
<211> LENGTH: 20
<212> TYPE: DNA
<213> ORGANISM: Artificial Sequence
<220> FEATURE:
<223> OTHER INFORMATION: PRIMER DIRECTED TO HUMAN CDC42

<400> SEQUENCE: 67
tacgaccgct gagttatcca                                              20

<210> SEQ ID NO 68
<211> LENGTH: 20
<212> TYPE: DNA
<213> ORGANISM: Artificial Sequence
<220> FEATURE:
<223> OTHER INFORMATION: PRIMER DIRECTED TO HUMAN CDC42

<400> SEQUENCE: 68
atctcaggca cccactttc                                               20

<210> SEQ ID NO 69
<211> LENGTH: 20
<212> TYPE: DNA
<213> ORGANISM: Artificial Sequence
<220> FEATURE:
<223> OTHER INFORMATION: PRIMER DIRECTED AGAINST HUMAN IL8

<400> SEQUENCE: 69
ctgcgccaac acagaaatta                                              20

<210> SEQ ID NO 70
<211> LENGTH: 20
<212> TYPE: DNA
<213> ORGANISM: Artificial Sequence
<220> FEATURE:
<223> OTHER INFORMATION: PRIMER DIRECTED AGAINST HUMAN IL8

<400> SEQUENCE: 70
acttctccac aaccctctgc                                              20

<210> SEQ ID NO 71
<211> LENGTH: 20
<212> TYPE: DNA
<213> ORGANISM: Artificial Sequence
<220> FEATURE:
<223> OTHER INFORMATION: PRIMER DIRECTED AGSINT HUMAN LSM3

<400> SEQUENCE: 71
gacgacgtag accagcaaca                                              20

<210> SEQ ID NO 72
<211> LENGTH: 20
<212> TYPE: DNA
<213> ORGANISM: Artificial Sequence
<220> FEATURE:
<223> OTHER INFORMATION: PRIMER DIRECTED AGSINT HUMAN LSM3

<400> SEQUENCE: 72
cgaagctctc ggtcatttct                                              20

<210> SEQ ID NO 73
<211> LENGTH: 20
```

```
<212> TYPE: DNA
<213> ORGANISM: Artificial Sequence
<220> FEATURE:
<223> OTHER INFORMATION: PRIMER DIRECTED AGAINST HUMAN MSN

<400> SEQUENCE: 73
aaggagagtg aggctgtgga                                              20

<210> SEQ ID NO 74
<211> LENGTH: 20
<212> TYPE: DNA
<213> ORGANISM: Artificial Sequence
<220> FEATURE:
<223> OTHER INFORMATION: PRIMER DIRECTED AGAINST HUMAN LSM3

<400> SEQUENCE: 74
cgaagctctc ggtcatttct                                              20

<210> SEQ ID NO 75
<211> LENGTH: 20
<212> TYPE: DNA
<213> ORGANISM: Artificial Sequence
<220> FEATURE:
<223> OTHER INFORMATION: PRIMER DIRECTED AGAINST HUMAN PTPN11

<400> SEQUENCE: 75
atatggcgtc atgcgtgtta                                              20

<210> SEQ ID NO 76
<211> LENGTH: 20
<212> TYPE: DNA
<213> ORGANISM: Artificial Sequence
<220> FEATURE:
<223> OTHER INFORMATION: PRIMER DIRECTED AGAINST HUMAN PTPN11

<400> SEQUENCE: 76
tccgtattcc cttgtccaac                                              20

<210> SEQ ID NO 77
<211> LENGTH: 20
<212> TYPE: DNA
<213> ORGANISM: Artificial Sequence
<220> FEATURE:
<223> OTHER INFORMATION: PRIMER DIRECTED AGAINST HUMAN SMAD2

<400> SEQUENCE: 77
gtgcaatctt tgtgcagagc                                              20

<210> SEQ ID NO 78
<211> LENGTH: 20
<212> TYPE: DNA
<213> ORGANISM: Artificial Sequence
<220> FEATURE:
<223> OTHER INFORMATION: PRIMER DIRECTED AGSINT HUMAN SMAD2

<400> SEQUENCE: 78
agcagcaaat tcctggttgt                                              20

<210> SEQ ID NO 79
<211> LENGTH: 20
<212> TYPE: DNA
<213> ORGANISM: Artificial Sequence
<220> FEATURE:
<223> OTHER INFORMATION: PRIMER DIRECTED AGAINST HUMAN SNTB2

<400> SEQUENCE: 79
```
ctgctgagct gatcaaggaa                                                20

<210> SEQ ID NO 80
<211> LENGTH: 20
<212> TYPE: DNA
<213> ORGANISM: Artificial Sequence
<220> FEATURE:
<223> OTHER INFORMATION: PRIMER DIRECTED AGAINST HUMAN SNTB2

<400> SEQUENCE: 80
cggtacaata tgctgctgga                                                20

<210> SEQ ID NO 81
<211> LENGTH: 20
<212> TYPE: DNA
<213> ORGANISM: Artificial Sequence
<220> FEATURE:
<223> OTHER INFORMATION: PRIMER DIRECTED AGSINT HUMAN FADD

<400> SEQUENCE: 81
gacctccaga acaggagtgg                                                20

<210> SEQ ID NO 82
<211> LENGTH: 20
<212> TYPE: DNA
<213> ORGANISM: Artificial Sequence
<220> FEATURE:
<223> OTHER INFORMATION: PRIMER DIRECTED AGAINST HUMAN FADD

<400> SEQUENCE: 82
atgcgtctga gttccatgac                                                20

<210> SEQ ID NO 83
<211> LENGTH: 20
<212> TYPE: DNA
<213> ORGANISM: Artificial Sequence
<220> FEATURE:
<223> OTHER INFORMATION: PRIMER DIRECTED AGAISNT HUMAN KLF11

<400> SEQUENCE: 83
gccggaagac ctacttcaaa                                                20

<210> SEQ ID NO 84
<211> LENGTH: 20
<212> TYPE: DNA
<213> ORGANISM: Artificial Sequence
<220> FEATURE:
<223> OTHER INFORMATION: PRIMER DIRECTED AGAINST HUMAN FADD

<400> SEQUENCE: 84
gctgcagttg aaaggcttct                                                20

<210> SEQ ID NO 85
<211> LENGTH: 20
<212> TYPE: DNA
<213> ORGANISM: Artificial Sequence
<220> FEATURE:
<223> OTHER INFORMATION: PRIMER DIRECTED AGAINST HUMAN VAMP7

<400> SEQUENCE: 85
gctcgagcca tgtgtatgaa                                                20

<210> SEQ ID NO 86
<211> LENGTH: 20
<212> TYPE: DNA
<213> ORGANISM: Artificial Sequence

```
<220> FEATURE:
<223> OTHER INFORMATION: PRIMER DIRECTED AGAINST HUMAN VAMP7

<400> SEQUENCE: 86
tccaccacag agaggtgaaa                                                   20

<210> SEQ ID NO 87
<211> LENGTH: 20
<212> TYPE: DNA
<213> ORGANISM: Artificial Sequence
<220> FEATURE:
<223> OTHER INFORMATION: PRIMER DIRECTED AGAINST HUMAN YWHAE

<400> SEQUENCE: 87
gcagaactgg atacgctgag                                                   20

<210> SEQ ID NO 88
<211> LENGTH: 20
<212> TYPE: DNA
<213> ORGANISM: Artificial Sequence
<220> FEATURE:
<223> OTHER INFORMATION: PRIMER DIRECTED AGAINST HUMAN YWHAE

<400> SEQUENCE: 88
cctgcatgtc tgaagtccat                                                   20

<210> SEQ ID NO 89
<211> LENGTH: 20
<212> TYPE: DNA
<213> ORGANISM: Artificial Sequence
<220> FEATURE:
<223> OTHER INFORMATION: PRIMER DIRECTED AGAINST HUMAN DAZAP2

<400> SEQUENCE: 89
tggtggaagg agggtatgat                                                   20

<210> SEQ ID NO 90
<211> LENGTH: 20
<212> TYPE: DNA
<213> ORGANISM: Artificial Sequence
<220> FEATURE:
<223> OTHER INFORMATION: PRIMER DIRECTED AGAINST HUMAN DAZAP2

<400> SEQUENCE: 90
aggaggtgga ggaggaatgt                                                   20

<210> SEQ ID NO 91
<211> LENGTH: 20
<212> TYPE: DNA
<213> ORGANISM: Artificial Sequence
<220> FEATURE:
<223> OTHER INFORMATION: PRIMER DIRECTED AGAINST HUMAN FOXM1

<400> SEQUENCE: 91
tgatggatct cagcaccact                                                   20

<210> SEQ ID NO 92
<211> LENGTH: 20
<212> TYPE: DNA
<213> ORGANISM: Artificial Sequence
<220> FEATURE:
<223> OTHER INFORMATION: PRIMER DIRECTED AGAINST HUMAN FOXM1

<400> SEQUENCE: 92
gggacggaga tgaggtctaa                                                   20
```

<210> SEQ ID NO 93
<211> LENGTH: 20
<212> TYPE: DNA
<213> ORGANISM: Artificial Sequence
<220> FEATURE:
<223> OTHER INFORMATION: PRIMER DIRECTED AGAINST HUMAN CDC25A

<400> SEQUENCE: 93
cccaaactcc actaccctga          20

<210> SEQ ID NO 94
<211> LENGTH: 20
<212> TYPE: DNA
<213> ORGANISM: Artificial Sequence
<220> FEATURE:
<223> OTHER INFORMATION: PRIMER DIRECTED AGAINST HUMAN CDC25A

<400> SEQUENCE: 94
gcggaacttc ttcaggtctt          20

<210> SEQ ID NO 95
<211> LENGTH: 20
<212> TYPE: DNA
<213> ORGANISM: Artificial Sequence
<220> FEATURE:
<223> OTHER INFORMATION: PRIMER DIRECTED AGAINST HUMAN CKS1B

<400> SEQUENCE: 95
atagccaagc tggtccctaa          20

<210> SEQ ID NO 96
<211> LENGTH: 20
<212> TYPE: DNA
<213> ORGANISM: Artificial Sequence
<220> FEATURE:
<223> OTHER INFORMATION: PRIMER DIRECTED AGAINST HUMAN CKS1B

<400> SEQUENCE: 96
tgtgaggttc tggttcatgg          20

<210> SEQ ID NO 97
<211> LENGTH: 20
<212> TYPE: DNA
<213> ORGANISM: Artificial Sequence
<220> FEATURE:
<223> OTHER INFORMATION: PRIMER DIRECTED AGAINST HUMAN IFI16

<400> SEQUENCE: 97
catggacgac tgaccacaat          20

<210> SEQ ID NO 98
<211> LENGTH: 20
<212> TYPE: DNA
<213> ORGANISM: Artificial Sequence
<220> FEATURE:
<223> OTHER INFORMATION: PRIMER DIRECTED AGAINST HUMAN IFI16

<400> SEQUENCE: 98
cctggtcttg atgaccttga          20

<210> SEQ ID NO 99
<211> LENGTH: 20
<212> TYPE: DNA
<213> ORGANISM: Artificial Sequence
<220> FEATURE:
<223> OTHER INFORMATION: PRIMER DIRECTED AGAINST HUMAN NCL

```
<400> SEQUENCE: 99
ttcaacagtg aggaggatgc                                               20

<210> SEQ ID NO 100
<211> LENGTH: 20
<212> TYPE: DNA
<213> ORGANISM: Artificial Sequence
<220> FEATURE:
<223> OTHER INFORMATION: PRIMER DIRECTED AGAINST HUMAN NCL

<400> SEQUENCE: 100
agccaccttc acccttaggt                                               20

<210> SEQ ID NO 101
<211> LENGTH: 20
<212> TYPE: DNA
<213> ORGANISM: Artificial Sequence
<220> FEATURE:
<223> OTHER INFORMATION: PRIMER DIRECTED AGAINST HUMAN NPM1

<400> SEQUENCE: 101
ggtggttctc ttcccaaagt                                               20

<210> SEQ ID NO 102
<211> LENGTH: 20
<212> TYPE: DNA
<213> ORGANISM: Artificial Sequence
<220> FEATURE:
<223> OTHER INFORMATION: PRIMER DIRECTED AGAINST HUMAN NPM1

<400> SEQUENCE: 102
agcctcttgg tcagtcatcc                                               20

<210> SEQ ID NO 103
<211> LENGTH: 20
<212> TYPE: DNA
<213> ORGANISM: Artificial Sequence
<220> FEATURE:
<223> OTHER INFORMATION: PRIMER DIRECTED AGAINST HUMAN POLR2G

<400> SEQUENCE: 103
tgattcagca ggacgatgag                                               20

<210> SEQ ID NO 104
<211> LENGTH: 20
<212> TYPE: DNA
<213> ORGANISM: Artificial Sequence
<220> FEATURE:
<223> OTHER INFORMATION: PRIMER DIRECTED AGAINST HUMAN POLR2G

<400> SEQUENCE: 104
tcagcttaca agccccaagt                                               20

<210> SEQ ID NO 105
<211> LENGTH: 20
<212> TYPE: DNA
<213> ORGANISM: Artificial Sequence
<220> FEATURE:
<223> OTHER INFORMATION: PRIMER DIRECTED AGSINT HUMAN S100A11

<400> SEQUENCE: 105
tgccttcaca aagaaccaga                                               20

<210> SEQ ID NO 106
```

```
<211> LENGTH: 20
<212> TYPE: DNA
<213> ORGANISM: Artificial Sequence
<220> FEATURE:
<223> OTHER INFORMATION: PRIMER DIRECTED AGSINT HUMAN S100A11

<400> SEQUENCE: 106
ccttgaggaa ggagtcatgg                                              20

<210> SEQ ID NO 107
<211> LENGTH: 20
<212> TYPE: DNA
<213> ORGANISM: Artificial Sequence
<220> FEATURE:
<223> OTHER INFORMATION: PRIMER DIRECTED AGAINST HUMAN SKP1

<400> SEQUENCE: 107
accctcctcc tcctgaagat                                              20

<210> SEQ ID NO 108
<211> LENGTH: 20
<212> TYPE: DNA
<213> ORGANISM: Artificial Sequence
<220> FEATURE:
<223> OTHER INFORMATION: PRIMER DIRECTED AGAINST HUMAN SKP1

<400> SEQUENCE: 108
cttggtccca aacagggata                                              20

<210> SEQ ID NO 109
<211> LENGTH: 20
<212> TYPE: DNA
<213> ORGANISM: Artificial Sequence
<220> FEATURE:
<223> OTHER INFORMATION: PRIMER DIRECTED AGAINST HUMAN TRIM32

<400> SEQUENCE: 109
tcgccagatt agccacttct                                              20

<210> SEQ ID NO 110
<211> LENGTH: 20
<212> TYPE: DNA
<213> ORGANISM: Artificial Sequence
<220> FEATURE:
<223> OTHER INFORMATION: PRIMER DIRECTED AGAINST HUMAN TRIM32

<400> SEQUENCE: 110
tggagaattt ccttgcgact                                              20

<210> SEQ ID NO 111
<211> LENGTH: 20
<212> TYPE: DNA
<213> ORGANISM: Artificial Sequence
<220> FEATURE:
<223> OTHER INFORMATION: PRIMER DIRECTED AGAINST HUMAN UBC

<400> SEQUENCE: 111
cgtgaagacc ctgactggta                                              20

<210> SEQ ID NO 112
<211> LENGTH: 20
<212> TYPE: DNA
<213> ORGANISM: Artificial Sequence
<220> FEATURE:
<223> OTHER INFORMATION: PRIMER DIRECTED TO HUMAN UBC

<400> SEQUENCE: 112
```

```
cttggatctt tgccttgaca                                                   20

<210> SEQ ID NO 113
<211> LENGTH: 20
<212> TYPE: DNA
<213> ORGANISM: Artificial Sequence
<220> FEATURE:
<223> OTHER INFORMATION: PRIMER DIRECTED TO HUMAN XRCC5

<400> SEQUENCE: 113
cctgaaagcc cttcaagaga                                                   20

<210> SEQ ID NO 114
<211> LENGTH: 20
<212> TYPE: DNA
<213> ORGANISM: Artificial Sequence
<220> FEATURE:
<223> OTHER INFORMATION: PRIMER DIRECTED TO HUMAN XRCC5

<400> SEQUENCE: 114
agaggcttcc tctttggtga                                                   20
```

US 9,970,057 B2

HUMAN INVASION SIGNATURE FOR PROGNOSIS OF METASTATIC RISK

CROSS-REFERENCE TO RELATED APPLICATIONS

This application is a U.S. national stage entry under 35 U.S.C. § 371 of PCT International Patent Application No. PCT/US2012/036544, filed May 4, 2012, which claims benefit of U.S. Provisional Application No. 61/483,345, filed May 6, 2011, the contents of each of which are incorporated herein by reference into the subject application.

STATEMENT OF GOVERNMENT SUPPORT

This invention was made with government support under grant number grant numbers ROI CA 113395, CA100324 and CA 126511 from the National Institutes of Health. The government has certain rights in the invention.

BACKGROUND OF THE INVENTION

Throughout this application various publications are referred to by number in parentheses. Full citations for these references may be found at the end of the specification. The disclosures of these publications are hereby incorporated by reference in their entirety into the subject application to more fully describe the art to which the subject invention pertains.

Breast cancer is one of the most frequent malignant neoplasms occurring in women in developed countries and metastasis of breast cancer is the main cause of death in these patients. The idea of personalized medicine and molecular profiling for prognostic tests has lead to a plethora of studies in the past 10 years in search of genetic determinants of metastasis. Such studies have identified gene sets, or "signatures", the expression of which in primary tumors is associated with higher risk of metastasis and poor disease outcome for the patients. Early methods of analysis treated the tumor as a whole, without respect to the different metastatic stages or the microenvironments. For example, the first molecular classification of tumors and identification of gene signatures associated with metastasis, were all derived from whole pieces of tumor tissue (1-6). These signatures were predictive of metastasis in patients and an important step towards applying these methods in clinical care. However, these signatures, mostly built to act as a general prognostic tool for the clinic, gave little information about the molecular biology of the different cell types comprising the tumor tissue and little insight into the specific mechanisms of metastasis.

We now know that tumors are highly heterogeneous, that not all cells within a tumor are migratory and invasive, and that the tumor microenvironment gives spatial-temporal cues to tumor cells for invasion and metastasis. In addition, metastasis is a multi-step process that involves the escape of cells from the primary tumor either via lymphatic or blood vessels, transport to and arrest in a target organ, and growth of metastases in the target organ. Each of these steps is a multicomponent process, with potentially different tumor cell properties and molecules playing critical roles, and therefore each of these steps separately deserves detailed attention. More recent signatures give such emphasis in detailed analysis of the role of the microenvironment in metastasis (7), as well as analysis of the tissue tropism for metastatic growth (8). The latter studies have been informative in prognosis of site-specific metastasis, as well as the cell biology behind the mechanisms of extravasation, homing and colonization at the distant metastatic site (9-11). However, little information is available about the crucial early steps of the metastatic cascade: migration, invasion and entry of tumor cells into the systemic circulation.

The present invention addresses this need by providing a gene expression profile specific for invasion and dissemination in human tumors.

SUMMARY OF THE INVENTION

A method is provided of determining a' subject having a tumor as (i) at risk of metastasis of the tumor, (ii) at risk of invasion of the tumor, or (iii) at risk of recurrence of the tumor after treatment of the tumor, comprising obtaining a sample of the tumor and determining the level of expression in the sample of one or more of the following genes (1) CSDE1, PGK1, FAU, DAZAP2, NPM1, SUMO1, ARHGDIB, TBCA, WBP5, MSN, S100A11, PTPN11, PRDX3, IMPDH2, RPL19, BTG1, SNTB2, NOP10, RPL37, UBC, RPS6, SET, STXBP2, ANXA5, NONO, STRBP, PSME2, YWHAE, SNRPD1, DUSP16, UCRC, ALDOA, XRCC5, PMAIP1, IFI16, DGUOK, TUBA3D, DCBLD2, PHACTR2, COX7B, MRPL27, SF3B2, IL8, ERH, LSM3, ATP5I, RPL12, MYL12A, CDC25A, GLO1, TUBA4A, GARS, RPL30, ATP5G1, PKM2, PSMB2, RPL11, SF3B14, EMP1, OSGEP, SPHK2, RPS24, DDAH1, ILF2, CDC42, SNRPD3, SDHD, FOXM1, RABIF, CALU, NCL, ITGAE, CAV1, PRDX5, and DNAJC8, and/or of one or more of (2) GLUD1, LIMS1, MDM2, MLL4, and DPP9, wherein if the level of expression of one or more of the genes in (1) is upregulated relative to a predetermined control and/or the level of expression of one or more of the genes in (2) is downregulated relative to a predetermined control, then the subject having the tumor is (i) at risk of metastasis of the tumor, (ii) at risk of invasion of the tumor, or (iii) at risk of recurrence of the tumor after treatment of the tumor, and wherein if the level of expression of all of the genes in (1) is not upregulated relative to a predetermined control and the level of expression of all of the genes in (2) is not downregulated relative to a predetermined control, then the subject having the tumor is not determined to be at risk of metastasis of the tumor, at risk of invasion of the tumor, and/or not determined to be at risk of recurrence of a tumor after treatment of the tumor.

Also provided is a method of determining a subject having a tumor as (i) at risk of metastasis of the tumor, (ii) at risk of invasion of the tumor, or (iii) at risk of recurrence of the tumor after treatment of the tumor, comprising obtaining a sample of the tumor and determining the level of expression in the sample of one or more of the genes (1) in the upregulated DNA Replication and Repair section of Table 1; (2) in the upregulated Embryonic and Tissue Development section of Table 1; (3) in the upregulated Cellular Movement and Development section of Table 1; (4) in the upregulated Cell-to-Cell Signaling and Interaction section of Table 1; and/or (5) in the upregulated Cellular Assembly and Organization section of Table 1;
and/or of one or more of the genes (6) in the downregulated Nervous System Development and Function section of Table 1; (7) in the downregulated Cell Death and Cell Cycle section of Table 1; (8) in the downregulated Hematological Disease section of Table 1; (9) in the Protein Synthesis and Cell Morphology section of Table 1; and/or (10) in the downregulated Drug and Nucleic Acid Metabolism section of Table 1;

wherein if the level of expression of one or more of the genes in (1), (2), (3), (4), or (5) is upregulated relative to a predetermined control and/or the level of expression of one or more of the genes in (6), (7), (8), (9), or (10) is downregulated relative to a predetermined control, then the subject having the tumor is (i) at risk of metastasis of the tumor, (ii) at risk of invasion of the tumor, or (iii) at risk of recurrence of the tumor after treatment of the tumor, and wherein if the level of expression of all of the genes in (1), (2), (3), (4), and (5) is not upregulated relative to a predetermined control and the level of expression of all of the genes in (6), (7), (8), (9), and (10) is not downregulated relative to a predetermined control, then the subject having the tumor is not determined to be at risk of metastasis of the tumor, at risk of invasion of the tumor, and/or not determined to be at risk of recurrence of a tumor after treatment of the tumor.

Also provided is a method of determining a subject having a tumor as (i) at risk of metastasis of the tumor, or (ii) at risk of recurrence of the tumor after treatment of the tumor, comprising obtaining a sample of the tumor and determining the level of expression of the following genes (1) CSDE1, PGK1, FAU, SKP1, DAZAP2, NPM1, SUMO1, ARHGDIB, TBCA, WBP5, MSN, S100A11, PTPN11, PRDX3, IMPDH2, RPL19, BTG1, SNTB2, NOLA3, RPL37, UBC, RPS6, SET, STXBP2, ANXA5, NONO, STRBP, PSME2, YWHAE, SNRPD1, DUSP16, UCRC, ALDOA, XRCC5, PMAIP1, IFI16, DGUOK, TUBA3D, DCBLD2, PHACTR2, COX7B, MRPL27, SF3B2, IL8, ERH, LSM3, ATP5I, RPL12, MYL12A, CDC25A, GLO1, TUBA4A, GARS, RPL30, ATP5G1, PKM2, PSMB2, RPL11, SF3B14, NONO, EMP1, OSGEP, SPHK2, RPS24, DDAH1, ILF2, CDC42, SNRPD3, SDHD, FOXM1, RABIF, CALU, NCL, ITGAE, CAV1, PRDX5, DNAJC8, ATP6V0A1, SMAD2, CKS1B, CDC2, DDX24, CAP1, CNN3, NCAPD3, SLC20A1, TXNDC9, UBE2D3, INTS7, CDK3, USP13, ANO6, FMOD, TAF4, ASPH, TRIM32, UTRN, POLR2G, ZNF207, PPM1A, ACVR1B, RFC3, KLF11, ZNF184, ARHGAP11A, VAMP7, FADD, ACAP2, ISLR, and
(2) MLL4, DPP9, SLCO1B3, C8orf79, MDM2, LIMS1, GLUD1, BBS2, CPZ, CCBL1, ZNF814, STEAP2, STK25, IREB2, ZNF165, CEACAM6, NAIP, TRIM13, STAR, CREB1, TSPAN14, ITGB5, SNRP70, MIB2, SLC25A37, SLC16A4, CNN2, CECR1, GP2, SLC45A2, ZNF621, EPB49, TST, BCL7B, DNASE1, TES, LONP2, RASA4, SGCB, F11, TAS2R20, ZFC3H1, ZNF790, HEBP2, RHOBTB3, DOC2B, MACF1, DLG1, ABCA11P, ZNF331, TTF1, FRG1, PEX2, SLC2A3, RAG1AP1, ABCD4, PNRC1, MPRIP, IL11, INA, YTHDC1, SLC31A1, KCNJ9, ANKRD11, CORO2A, CPM, IL32, MYO1C, SLC38A2, IL10RB, VDR, NDN, ITGB3BP, HSPB6, POFUT1, SH3BP2, SFXN2, EIF4A1, CDS1, PPF1BP1, S1PR2, RPL37, GTF2I, RRP1, ATP8A1, GATAD2B, NDUFB2, PCYOX1, NUP62, TGFB1I1, ACRBP, TNFRSF9, AKAP13, PIP5K1C, UBR5, SYNC, CHP, GOSR1, PSMD5, ANKRD17, HSDL2, ZNF517 wherein if the level of expression of all of the genes in (1) is upregulated relative to a predetermined control and/or the level of expression of all of the genes in (2) is downregulated relative to a predetermined control, then the subject having the tumor is (i) at risk of metastasis of the tumor, or (ii) at risk of recurrence of the tumor after treatment of the tumor, and wherein if the level of expression of all of the genes in (1) is not upregulated relative to a predetermined control and/or the level of expression of all of the genes in (2) is not downregulated relative to a predetermined control, then the subject having the tumor is not determined to be at risk of metastasis of the tumor, and/or not determined to be at risk of recurrence of a tumor after treatment of the tumor.

A product is provided comprising one or more microarrays comprising a plurality of oligonucleotide probes for determining the level of expression of the following genes (1): CSDE1, PGK1, FAU, SKP1, DAZAP2, NPM1, SUMO1, ARHGDIB, TBCA, WBP5, MSN, S100A11, PTPN11, PRDX3, IMPDH2, RPL19, BTG1, SNTB2, NOLA3, RPL37, UBC, RPS6, SET, STXBP2, ANXA5, NONO, STRBP, PSME2, YWHAE, SNRPD1, DUSP16, UCRC, ALDOA, XRCC5, PMAIP1, IFI16, DGUOK, TUBA3D, DCBLD2, PHACTR2, COX7B, MRPL27, SF3B2, IL8, ERH, LSM3, ATP5I, RPL12, MYL12A, CDC25A, GLO1, TUBA4A, GARS, RPL30, ATP5G1, PKM2, PSMB2, RPL11, SF3B14, NONO, EMP1, OSGEP, SPHK2, RPS24, DDAH1, ILF2, CDC42, SNRPD3, SDHD, FOXM1, RABIF, CALU, NCL, ITGAE, CAV1, PRDX5, DNAJC8, ATP6V0A1, SMAD2, CKS1B, CDC2, DDX24, CAP1, CNN3, NCAPD3, SLC20A1, TXNDC9, UBE2D3, INTS7, CDK3, USP13, ANO6, FMOD, TAF4, ASPH, TRIM32, UTRN, POLR2G, ZNF207, PPM1A, ACVR1B, RFC3, KLF11, ZNF184, ARHGAP11A, VAMP7, FADD, ACAP2, ISLR.

A kit is provided for determining (i) risk of metastasis of a tumor in a subject, or (ii) risk of invasion of a tumor, or (iii) risk of recurrence of a tumor after treatment of the tumor in a subject, the kit comprising one or more microarray(s) comprising the product of any of claims 12-14 and instructions for use. In an embodiment, the kit further comprises one or more control samples. In an embodiment, the kit further comprises reverse transcriptase-polymerase chain reaction (RT PCR) reagents.

A method is also provided of inhibiting metastasis of a tumor in a subject, of inhibiting invasion of a tumor in a subject, or of reducing risk of recurrence of a tumor in a subject after treatment of the tumor, comprising administering to the subject an inhibitor of interleukin-8 and/or an inhibitor of phosphatase Shpt and/or an inhibitor of TGF☐ and/or an inhibitor of PTPN11, in an amount effective to inhibit metastasis of a tumor or inhibit invasion of a tumor or duce risk of recurrence of a tumor after treatment of the tumor.

A method of treating a cancer in a subject comprising administering, to a subject determined by the method of any of claims 1-11 or 18-25 to be (i) at risk of metastasis of a tumor of the cancer or (ii) at risk of invasion of a tumor, or (iii) at risk of recurrence of a tumor of the cancer after treatment of the tumor, an anti-metastatic therapy or an anti-invasion therapy or an anti-recurrent therapy, respectively, so as to thereby treat the cancer in the subject. In an embodiment of the method, the cancer is a breast cancer. In an embodiment of the method, the subject is a human.

Figure 7:
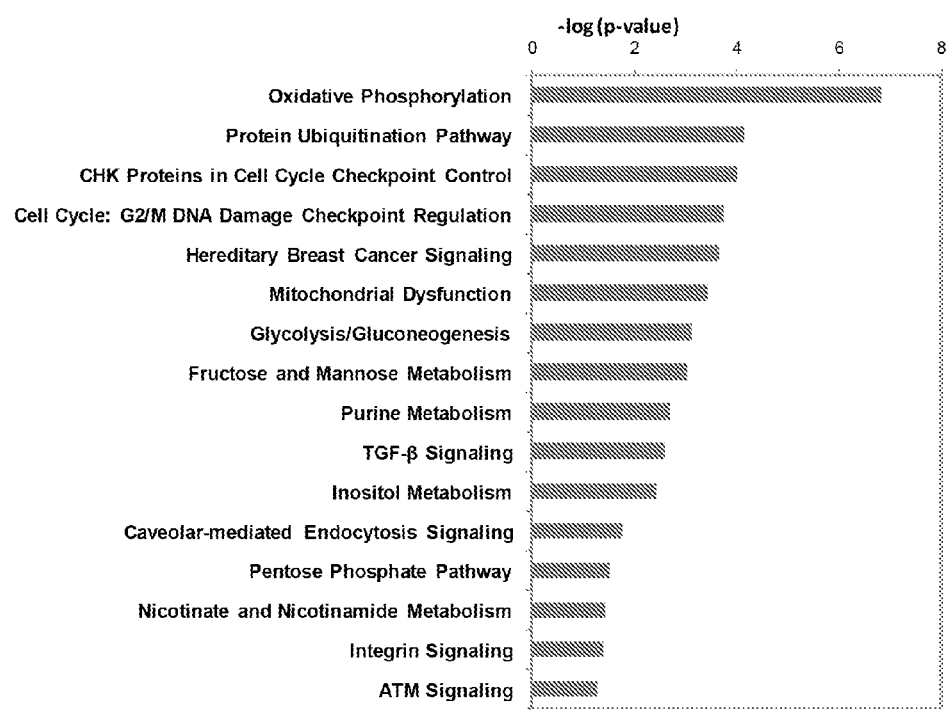

p-value for log-rank test p=0.000. (1C). Cox proportional hazards model analysis was repeated for the UNC database, excluding the patients of the basal-like breast cancer subtype. The human invasion signature is significantly correlated with recurrence in the remaining patients. p-value for log-rank test p=0.000. (1D). Cox proportional hazards model analysis was repeated for the NKI database, excluding the patients of the basal-like breast cancer subtype. The human invasion signature is significantly correlated with distant metastasis in the remaining patients. p-value for log-rank test p=0.001. (1E). An R value (see Methods & Materials) was calculated to assess the correlation between the human invasion signature pattern and the gene expression of each tumor in the UNC database. In the plot shown, R values for all patients are clustered by breast cancer subtype. R values above the dotted line are significant at $p<0.05$. Genes used in FIG. 1 are a subset of the HIS and are listed in table 6 below. Use of all genes of the HIS for prediction of outcome is shown in FIG. 7. (Complete list of genes of the HIS can be found in Tables 7 and 8).

Figure 2:
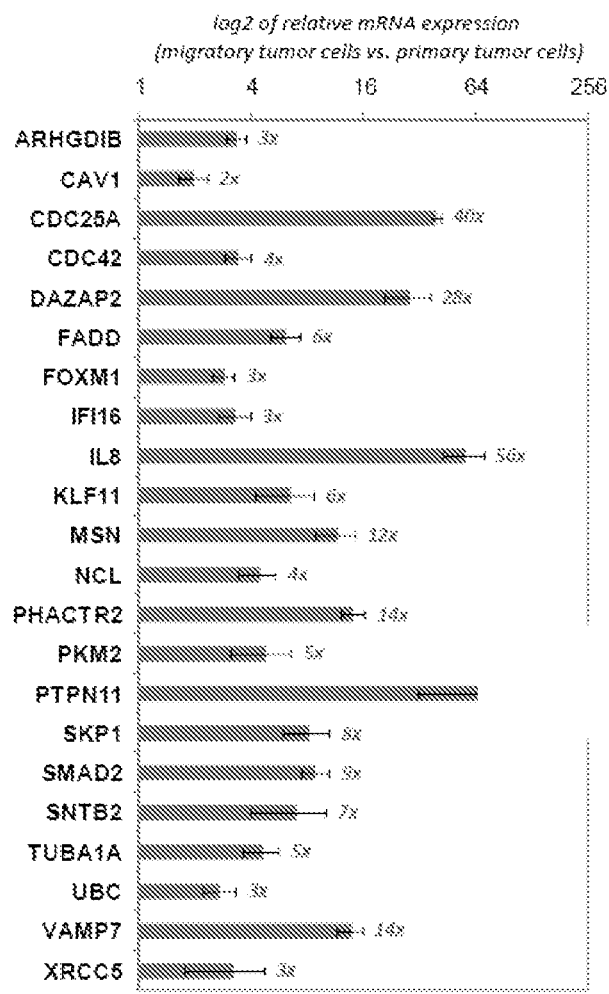

FIG. 2: Validation of specific genes upregulated in the migratory tumor cells. mRNA expression of genes from the top three significant upregulated function networks in Table 1 was assessed by real-time PCR in independent biological repeats of migratory tumor cells vs. average primary tumor cells from MDA-MB-231 breast tumors. Bars: relative mRNA expression of migratory tumor cells compared to average primary tumor (average), log 2 transformed scale. The linear fold-upregulation for every gene is shown at the end of every bar. Error bars: SEM, n=6, p<0.05 for all data shown in this graph (Student's t-test).

Figures 3A, 3B, 3C:
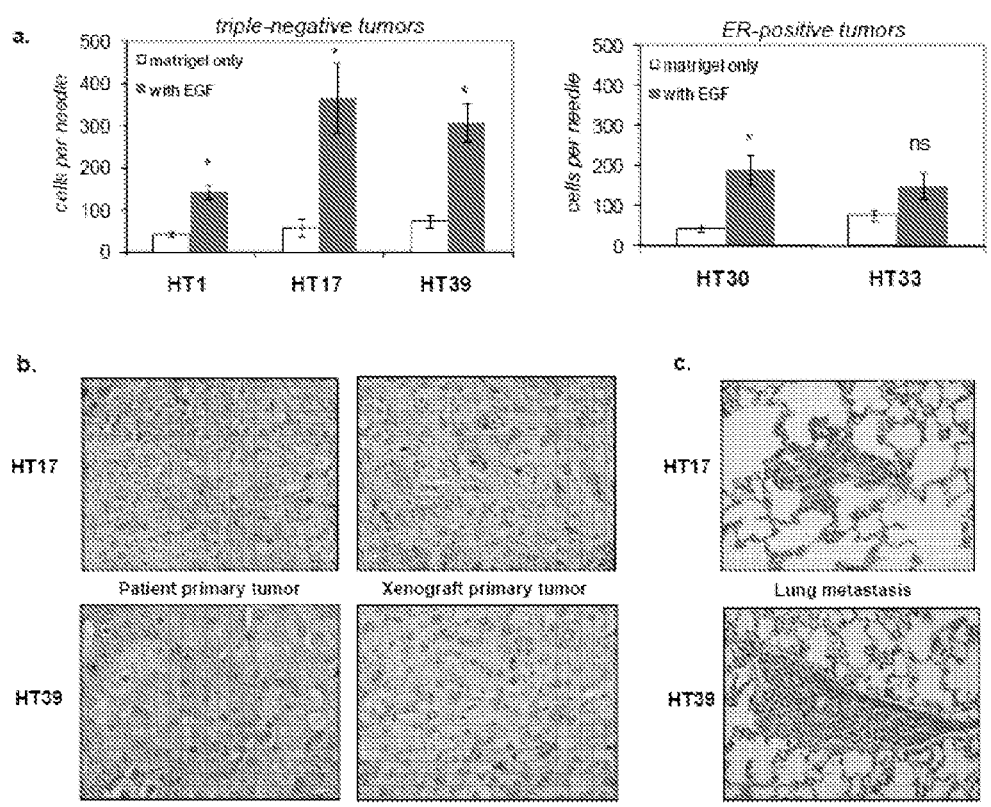

FIG. 3A-3C: Orthotopic patient-derived breast tumor xenografts are invasive and metastatic in the mice. (3A). Migratory cells were collected from the patient-derived primary tumors with the in vivo invasion assay in response to human EGF. Matrigel needles with no added chemoattractant were used as control. Fetal bovine serum (FBS) was also used as a general chemoattractant source with similar results (not shown). Results are plotted as average number of total cells per needle. Error bars: SEM, *: p<0.05 by Student's t-test, ns: not significant, n≥5 mice. (3B). Histology of the xenograft primary tumors and the primary tumor from the corresponding patient of origin for HT17 and HT39. Magnification: 40×. (3C) Histology of spontaneous lung metastasis in the mice from the orthotopic breast tumors HT17 and HT39. Magnification: 40×.

Figures 4A, 4B, 4C:
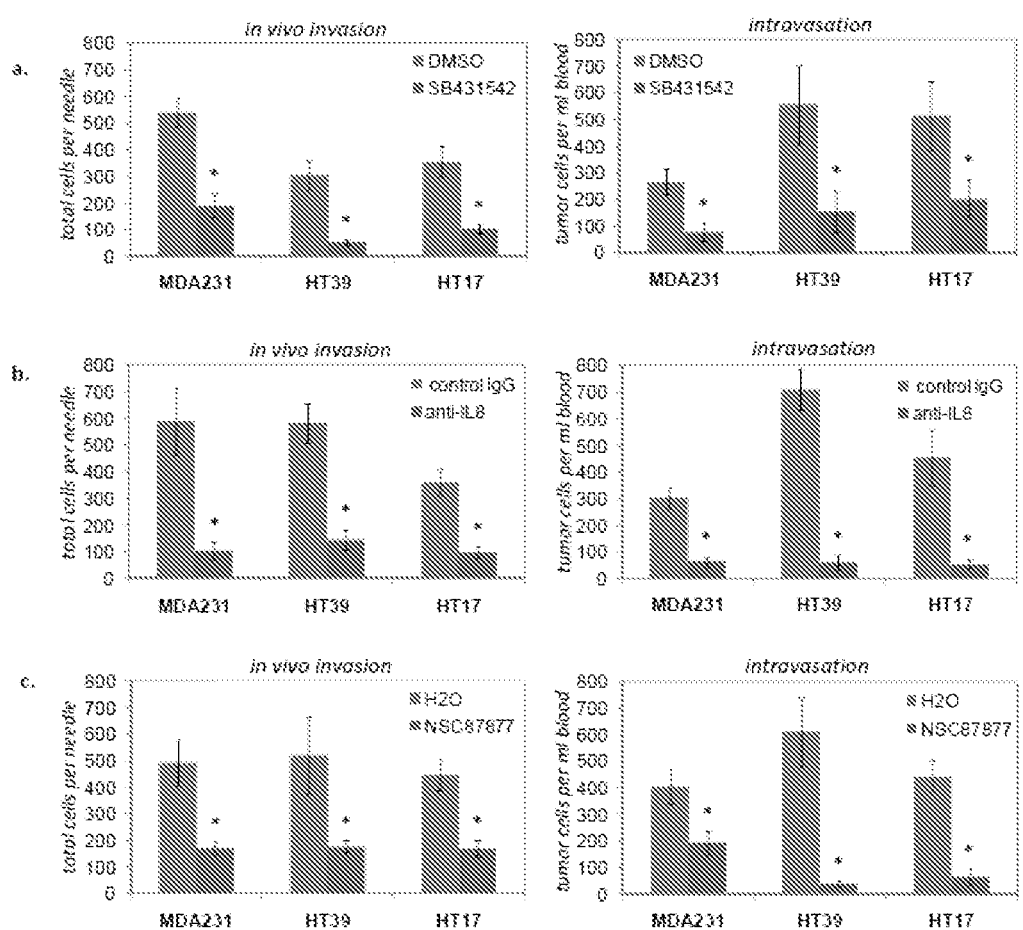

FIG. 4A-4C: Functional validation of specific targets from the human invasion signature in patient-derived primary breast tumors. In vivo invasion and intravasation were measured in MDA-MB-231 tumors and in the patient-derived tumors HT17 and HT39. In vivo invasion is plotted as average number of cells per needle, intravasation is plotted as average number of circulating tumor cells per ml of blood. Bars: average number of cells, Error Bars: SEM, n≥6 microneedles from at least four mice for the in vivo invasion assay, n≥6 mice for the intravasation assay, *: p<0.05 by Student's t-test and Mann-Whitney U-test. (4A). In vivo invasion and intravasation measurement in tumor-bearing mice treated with either DMSO vehicle control or the TGFβ specific inhibitor SB431542. (4B). Same measurements in mice treated either with a control IgG or a blocking antibody for IL8. (4C). Same measurements in mice treated either with water vehicle control or the PTPN11 specific inhibitor NSC87877.

Figure 5:
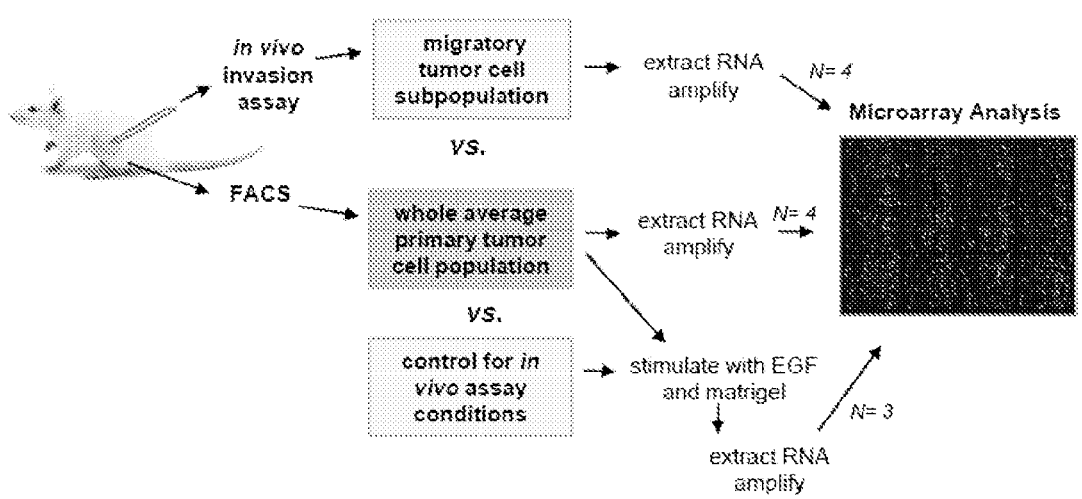

FIG. 5. Schematic of the experimental method for the gene expression analysis of invasive human breast tumor cells. Orthotopic xenografts of human MDA-MB-231-GFP breast adenocarcinoma cells were made in SCID mice. Migratory cells were isolated with the in vivo invasion assay, where cells are stimulated to migrate towards an EGF gradient and through a matrigel gel. The average primary tumor cells (APTCs) were isolated by FACS sorting for live GFP-positive cells from a whole tumor cell preparation. Both populations are tumor cells by more than 95% purity: we have shown that invasive cells from MDA-MB-231 tumors consist 95% tumor cells (Patsialou et al., 2009), and the purity of the APTCs was determined by post-sort FACS analysis. RNA was extracted from both the purified cell populations and used for microarray analysis after amplification. A total of 6 biological repeats were used per sample for the analysis.

Figures 6A, 6B, 6C:
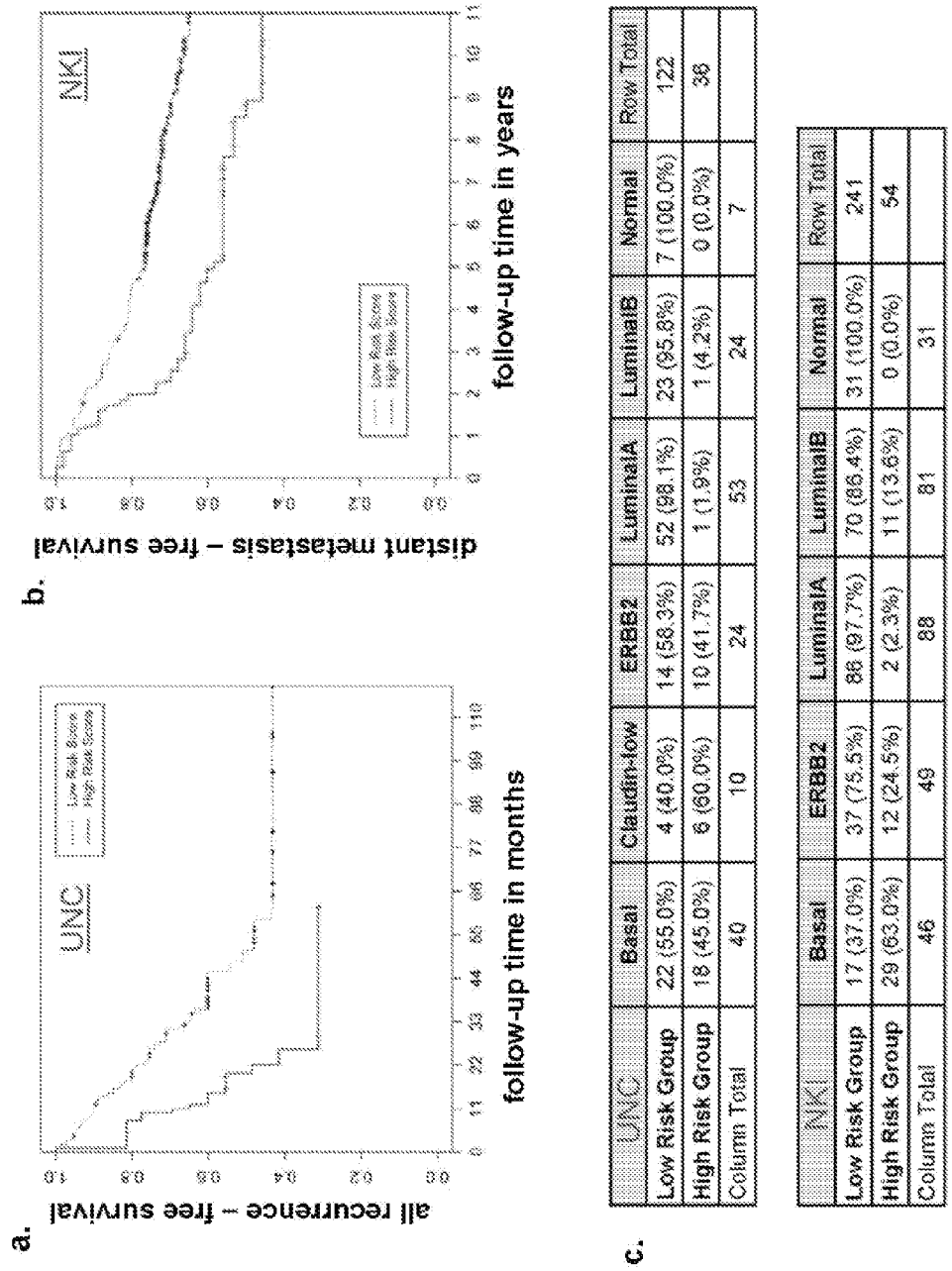

FIG. 6A-6C. The human invasion signature is correlated with risk of metastasis and recurrence in breast cancer patients. Expression of all 185 genes in the human invasion signature (HIS) was correlated with the disease outcomes of breast cancer patients in public microarray databases using the Cox proportional hazards model. (6A). The whole HIS signature is predictive of disease recurrence in the UNC database. p-value for log-rank test p=0.000. (6B) The whole HIS signature is predictive of distant metastasis in the NKI database. p-value for log-rank test p=0.003. (6C) Subgrouping by molecular subtype of the low-risk and high-risk patients groups of the above analysis. Patients of all breast cancer subtypes, except for Normal subtypes, were categorized in high-risk group by the analysis.

FIG. 7. Canonical pathways significantly enriched in the human invasion signature. Ingenuity Pathway Analysis (IPA) of the human invasion signature was performed towards canonical pathways. Shown are the pathways that were designated significant by the software, with a p-value <0.05 by Fisher's Exact test.

Figures 8A, 8B:
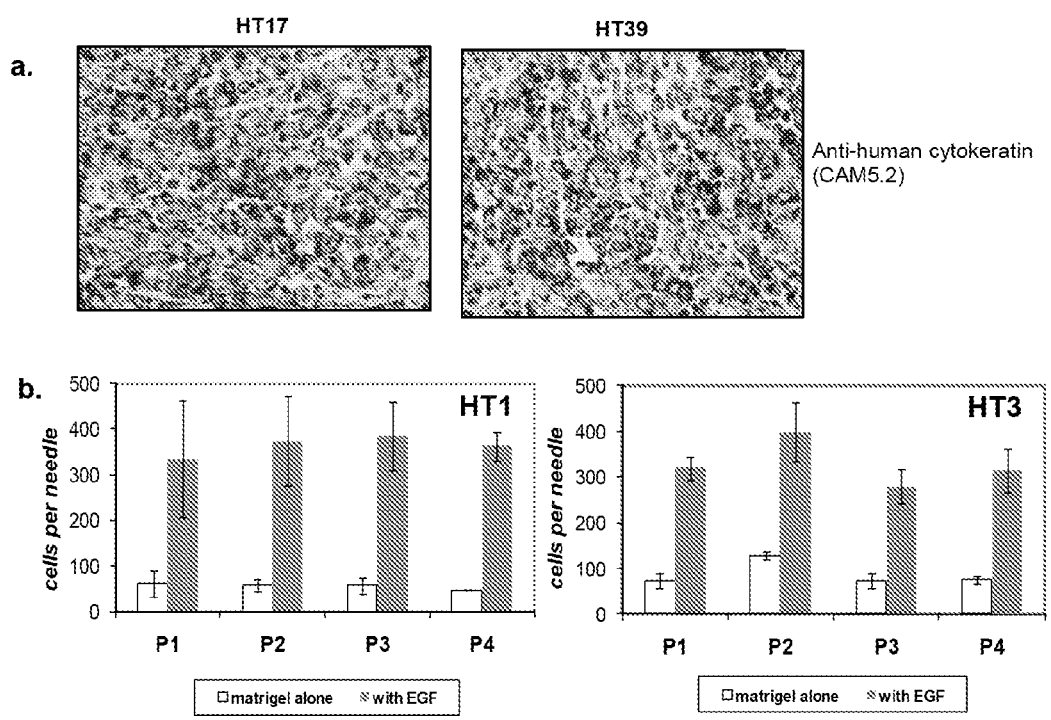

FIG. 8A-8B. (8A) Primary tumor tissue from the patient-derived xenografts was immunostained with a human specific anti-cytokeratin antibody (CAM5.2—Becton Dickinson, San Jose Calif.), shown as brown staining in the images), in order to verify that the tumor remains human after growth in the mouse. As a control, primary tumor tissue from MMTV-PyMT transgenic mice was immunostained and negative staining of tumor cells with the CAM5.2 antibody was confirmed. (8B) In vivo invasion assay for the patient-derived tumors HT17 and HT39 to an EGF gradient, in passage 1 through passage 4 of the tumor in the mice. The number of migratory cells remains similar over the passages (by Student's t-test, p=0.47 for HT17, p=0.82 for HT39).

Figures 9A, 9B, 9C:
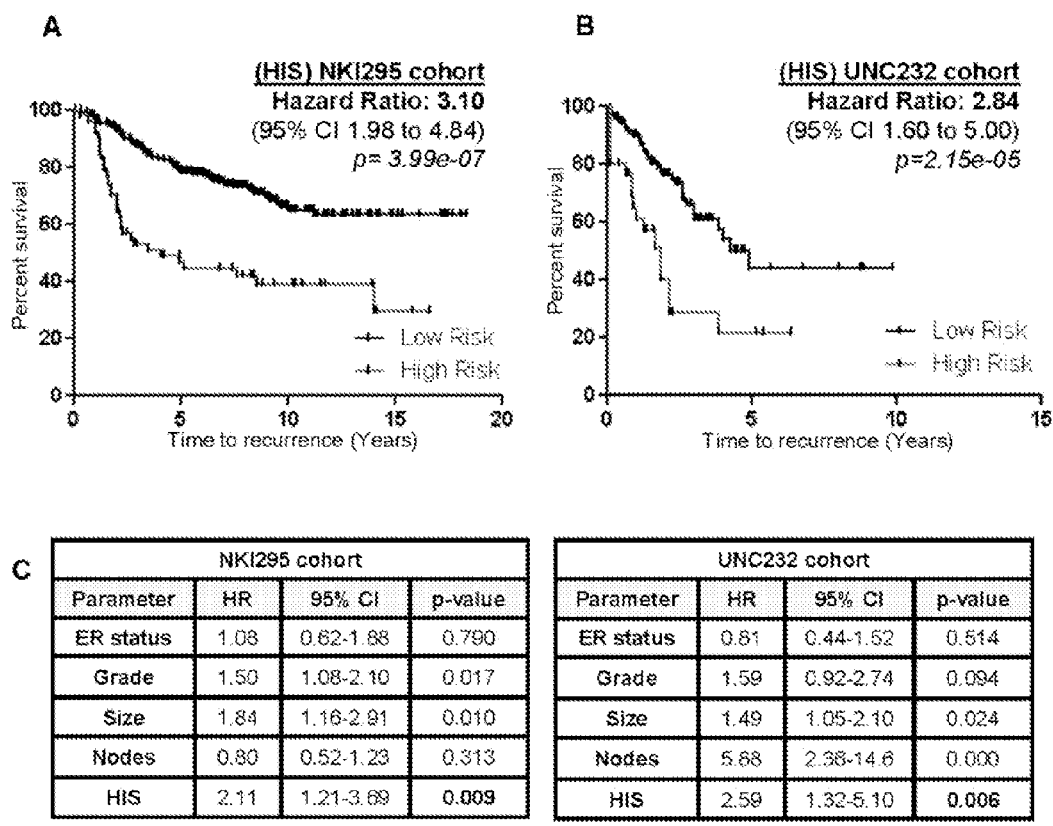

FIG. 9A-9C: The Human Invasion Signature is prognostic of metastasis in breast cancer patient cohorts. (9A) Metastasis-free survival Kaplan-Meier analysis on cases identified as high and low risk by the Human Invasion Signature (HIS) in the NKI295 cohort. Hazard ratio 3.10, 95% CI 1.98 to 4.84. p=3.99e-07(log-rank test). (9B) Recurrence-free survival Kaplan-Meier analysis on cases identified as high and low risk by the HIS in the UNC232 cohort. Hazard ratio 2.84, 95% CI 1.60 to 5.00. p=2.15e-05 (log-rank test). One thousand signatures of equal size to the HIS were generated by picking random genes from the genome, and their association to distant metastasis in the NKI295 cohort was calculated. (9C) Multivariate Cox-Proportional Hazard Regression Analysis of the HIS in the NKI295 and UNC232 cohorts, incorporating established clinical parameters. HR: Hazard Ratio, CI: Confidence Intervals. A Pearson's correlation R value was calculated to assess the relationship between the HIS gene expression pattern and the gene expression of each tumor in the UNC232 database. Patients in all breast cancer subtype were found to have R values significant at p<0.05.

Figure 10:
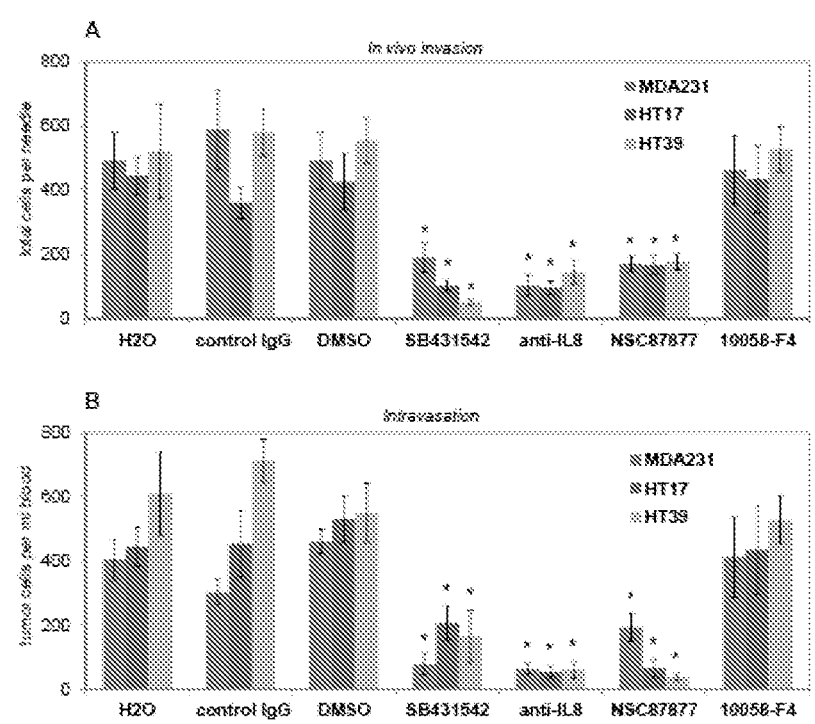

FIG. 10. Functional validation of specific targets from the human invasion signature in patient-derived breast tumors. In vivo invasion and intravasation were measured in MDA-MB-231, HT17 and HT39 tumors. (A) In vivo invasion is plotted as average number of cells per microneedle. (B) Intravasation is plotted as average number of circulating tumor cells per ml of blood. Results are shown for mice that received treatment with either vehicle control or specific inhibitor: TGFβ receptor specific inhibitor SB431542, PTPN11 specific inhibitor NSC87877, neutralizing antibody specific to human IL8, MYC specific inhibitor 10058-F4 (negative control). Bars: average number of cells, Error Bars: SEM, *: p<0.05 (Student's t-test), n≥6 microneedles from at least four mice for the in vivo invasion assay, n≥6 mice for the intravasation assay.

Figure 11:
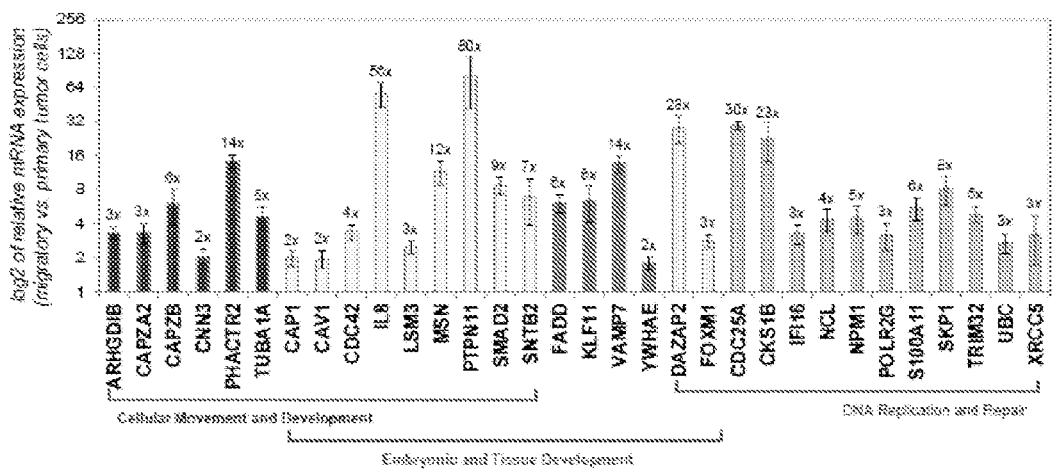
Figures 12A, 12B, 12C, 12D:
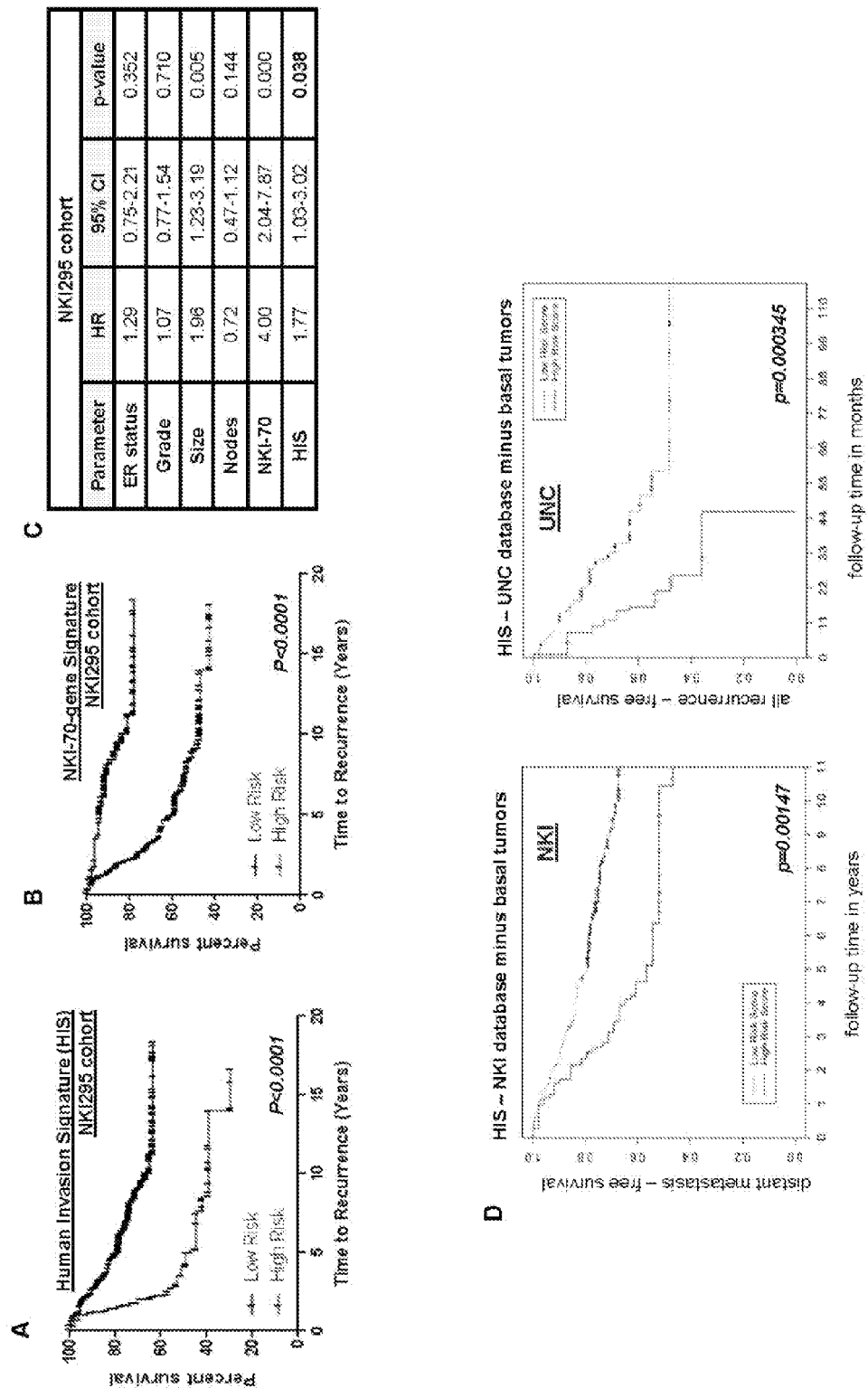

FIG. 11. A further investigation of the earlier results shown in FIG. 2. Validation of specific genes from the top upregulated functions in the Human Invasion Signature. The human invasion signature was analyzed for significant regulated functions using the Ingenuity Pathway Analysis software. Significance is calculated through IPA by righttailed Fisher's exact test. mRNA expression of genes from the top three significant upregulated functions was assessed by real-time PCR in independent biological repeats from MDA-MB-231 breast tumors. Genes are grouped in colors by function, as determined by IPA and Gene Ontology annotations. Red: Cellular Movement and Development, Blue: Embryonic and Tissue Development, Brown: DNA replication and Repair, Yellow or light blue: genes with double function annotations. Bars: relative average mRNA expression of migratory cells compared to average primary tumor, log 2 transformed scale for ease of display. The linear fold upregulation is shown at the end of every bar. Error bars: SEM, n=6, p<0.05 for all data shown in this graph (Student's t-test). The biggest overlap for genes having double annotated functions was seen between the "embryonic and tissue development" and the "cellular movement" gene networks, with more than half of the genes shared between the two functions.

FIG. 12A-12D. Comparative analysis of the Human Invasion Signature with the NKI-70-signature and analysis of the Human Invasion Signature excluding basal-like patients. (13A). Metastasis-free survival Kaplan-Meier analysis on cases identified as high and low risk by the Human Invasion Signature HIS in the NKI295 cohort (P<0.0001). Graph is repeated here for ease of comparison. (13B). Metastasis-free survival Kaplan-Meier analysis on cases identified as high and low risk by the NKI-70-gene signature in the NKI295 cohort (P<0.0001). (13C). Multivariate Cox Proportional Hazard Regression Analysis was performed to evaluate the relationship between the HIS and distant metastasis in the NKI295 cohort incorporating relevant clinical variables as well as the NKI-70-signature (HR: Hazard Ratio, I: Confidence Interval). The HIS is significant even in the presence of the NKI-70-signature, indicating that it contains additional prognostic information for this cohort over what is captured by the NKI-70-signature. (13D). The HIS remains prognostic of outcome in patient cohorts after exclusion of basal-like patients. Cox proportional hazards model analysis was repeated for the NKI and the UNC cohorts, excluding the patients of the basal-like breast cancer subtype. p=0.00147 for NKI and p=0.000345 for UNC (log-rank test).

Figures 13A, 13B, 13C:
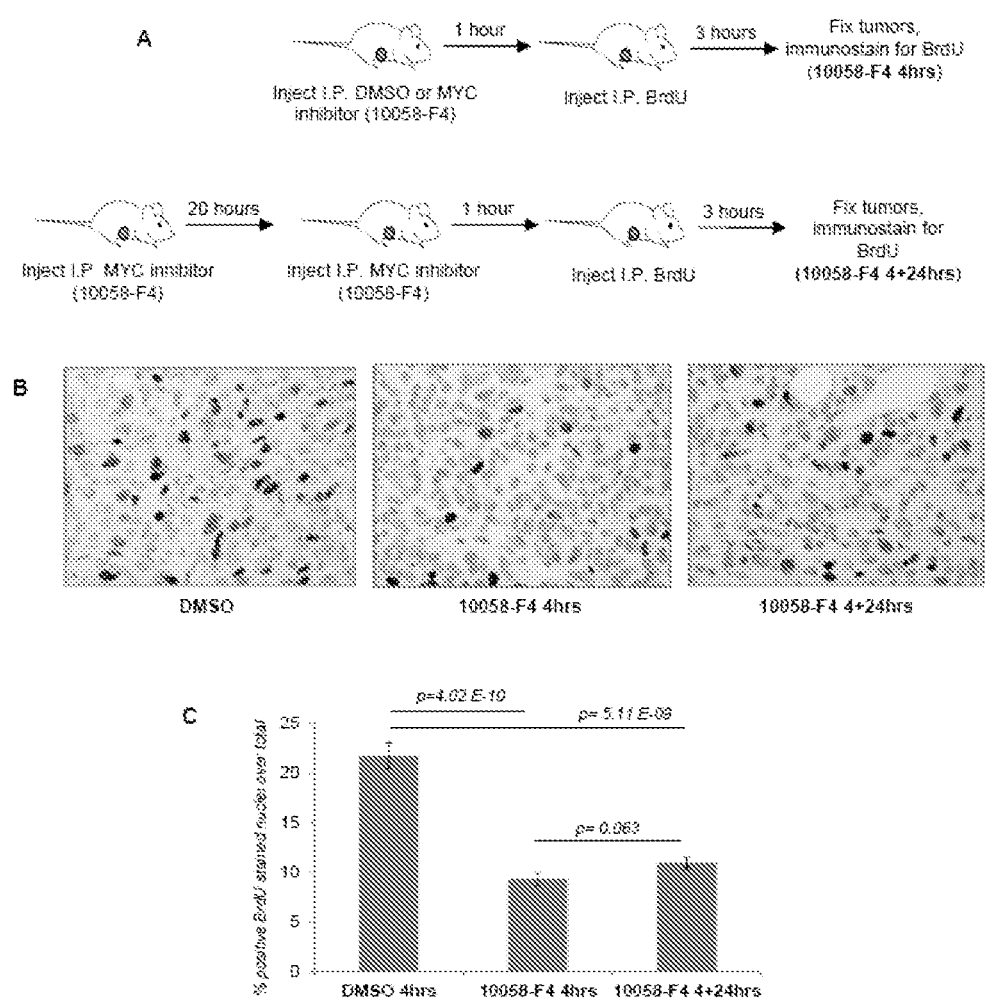

FIG. 13A-13C. Injection of the MYC inhibitor 10058-F4 in MDA-MB-231 xenograft mice significantly inhibits proliferation in vivo. (15A). Schematic of experimental design for the inhibitor treatments. (15B). Representative images of immunostained tumors sections with BrdU antibody (black) and counterstained for nuclei (gray). (15C). Quantification of the above experiments is shown for 3 mice per group, and 10 random 40x images per mouse/tumor (excluding necrotic areas). Bars represent the average percentage of BrdU positive nuclei (black) over total (gray). Error bars: SEM. p-values by Student's t-test.

DETAILED DESCRIPTION OF THE INVENTION

A method is provided of determining a subject having a tumor as (i) at risk of metastasis of the tumor, (ii) at risk of invasion of the tumor, or (iii) at risk of recurrence of the tumor after treatment of the tumor, comprising obtaining a sample of the tumor and determining the level of expression in the sample of one or more of the following genes (1) CSDE1, PGK1, FAU, DAZAP2, NPM1, SUMO1, ARHGDIB, TBCA, WBP5, MSN, S100A11, PTPN11, PRDX3, IMPDH2, RPL19, BTG1, SNTB2, NOP10, RPL37, UBC, RPS6, SET, STXBP2, ANXA5, NONO, STRBP, PSME2, YWHAE, SNRPD1, DUSP16, UCRC, ALDOA, XRCC5, PMAIP1, IFI16, DGUOK, TUBA3D, DCBLD2, PHACTR2, COX7B, MRPL27, SF3B2, IL8, ERH, LSM3, ATP5I, RPL12, MYL12A, CDC25A, GLO1, TUBA4A, GARS, RPL30, ATP5G1, PKM2, PSMB2, RPL11, SF3B 14, EMP1, OSGEP, SPHK2, RPS24, DDAH1, ILF2, CDC42, SNRPD3, SDHD, FOXM1, RABIF, CALU, NCL, ITGAE, CAV1, PRDX5, and DNAJC8, and/or of one or more of (2) GLUD1, LIMS1, MDM2, MLL4, and DPP9, wherein if the level of expression of one or more of the genes in (1) is upregulated relative to a predetermined control and/or the level of expression of one or more of the genes in (2) is downregulated relative to a predetermined control, then the subject having the tumor is (i) at risk of metastasis of the tumor, (ii) at risk of invasion of the tumor, or (iii) at risk of recurrence of the tumor after treatment of the tumor, and wherein if the level of expression of all of the genes in (1) is not upregulated relative to a predetermined control and the level of expression of all of the genes in (2) is not downregulated relative to a predetermined control, then the subject having the tumor is not determined to be at risk of metastasis of the tumor, at risk of invasion of the tumor, and/or not determined to be at risk of recurrence of a tumor after treatment of the tumor.

In an embodiment, the method comprises determining the level of expression of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, or 74 genes of or all 75 genes of, (1) CSDE1, PGK1, FAU, DAZAP2, NPM1, SUMO1, ARHGDIB, TBCA, WBP5, MSN, S100A11, PTPN11, PRDX3, IMPDH2, RPL19, BTG1, SNTB2, NOP10, RPL37, UBC, RPS6, SET, STXBP2, ANXA5, NONO, STRBP, PSME2, YWHAE, SNRPD1, DUSP16, UCRC, ALDOA, XRCC5, PMAIP1, IFI16, DGUOK, TUBA3D, DCBLD2, PHACTR2, COX7B, MRPL27, SF3B2, IL8, ERH, LSM3, ATP5I, RPL12, MYL12A, CDC25A, GLO1, TUBA4A, GARS, RPL30, ATP5G1, PKM2, PSMB2, RPL11, SF3B14, EMP1, OSGEP, SPHK2, RPS24, DDAH1, ILF2, CDC42, SNRPD3, SDHD, FOXM1, RABIF, CALU, NCL, ITGAE, CAV1, PRDX5, and DNAJC8.

In an embodiment, the method comprises determining the level of expression of 2, 3, 4, or all 5 genes of (2) GLUD1, LIMS1, MDM2, MLL4, and DPP9.

In an embodiment of the method, if the level of expression of 2 or more, 3 or more, 4 or more, 5 or more, 10 or more, 15 or more, 20 or more, 25 or more, 30 or more, 35 or more, 40 or more, 45 or more, 50 or more, 55 or more, 60 or more, 65 or more, 70 or more, or all 75 of the genes in (1) is upregulated relative to a predetermined control then the subject having the tumor is (i) at risk of metastasis of the tumor, (ii) at risk of invasion of the tumor, or (iii) at risk of recurrence of the tumor after treatment of the tumor, and wherein if the level of expression of all of the genes in (1) is not upregulated relative to a predetermined control, then the subject having the tumor is not determined to be at risk of metastasis of the tumor, at risk of invasion of the tumor, and/or not determined to be at risk of recurrence of a tumor after treatment of the tumor.

In an embodiment of the method, if the level of expression of 2, 3, 4 or 5 of the genes in (2) is downregulated relative to a predetermined control then the subject having the tumor is (i) at risk of metastasis of the tumor, (ii) at risk of invasion of the tumor, or (iii) at risk of recurrence of the tumor after treatment of the tumor, and wherein if the level of expression of all of the genes in (2) is not downregulated relative to a predetermined control, then the subject having the tumor is not determined to be at risk of metastasis of the tumor, at risk of invasion of the tumor, and/or not determined to be at risk of recurrence of a tumor after treatment of the tumor.

Also provided is a method of determining a subject having a tumor as (i) at risk of metastasis of the tumor, (ii) at risk of invasion of the tumor, or (iii) at risk of recurrence of the tumor after treatment of the tumor, comprising obtaining a sample of the tumor and determining the level of expression in the sample of one or more of the genes (1) in the upregulated DNA Replication and Repair section of Table 1; (2) in the upregulated Embryonic and Tissue Development section of Table 1; (3) in the upregulated Cellular Movement and Development section of Table 1; (4) in the upregulated Cell-to-Cell Signaling and Interaction section of Table 1; and/or (5) in the upregulated Cellular Assembly and Organization section of Table 1;
and/or of one or more of the genes (6) in the downregulated Nervous System Development and Function section of Table 1; (7) in the downregulated Cell Death and Cell Cycle section of Table 1; (8) in the downregulated Hematological Disease section of Table 1; (9) in the Protein Synthesis and Cell Morphology section of Table 1; and/or (10) in the downregulated Drug and Nucleic Acid Metabolism section of Table 1;
wherein if the level of expression of one or more of the genes in (1), (2), (3), (4), or (5) is upregulated relative to a predetermined control and/or the level of expression of one or more of the genes in (6), (7), (8), (9), or (10) is downregulated relative to a predetermined control, then the subject having the tumor is (i) at risk of metastasis of the tumor, (ii) at risk of invasion of the tumor, or (iii) at risk of recurrence of the tumor after treatment of the tumor, and wherein if the level of expression of all of the genes in (1), (2), (3), (4), and (5) is not upregulated relative to a predetermined control and the level of expression of all of the genes in (6), (7), (8), (9), and (10) is not downregulated relative to a predetermined control, then the subject having the tumor is not determined to be at risk of metastasis of the tumor, at risk of invasion of the tumor, and/or not determined to be at risk of recurrence of a tumor after treatment of the tumor.

In an embodiment, the method comprises determining the level of expression of all of the genes in (1), (2), (3), (4) or (5). In an embodiment, the method comprises determining the level of expression of one or more of the genes in (1), (2), (3), (4) or (5), or five or more of the genes in (1), (2), (3), (4) or (5), or ten or more of the genes in (1), (2), (3), (4) or (5), or fifteen or more of the genes in (1), (2), (3), (4) or (5).

In an embodiment, the method comprises determining the level of expression of all of the genes in (6), (7), (8), (9) or (10). In an embodiment, the method comprises determining the level of expression of one or more of the genes in (6), (7), (8), (9) or (10), or five or more of the genes in (6), (7), (8), (9) or (10), or ten or more of the genes in (6), (7), (8), (9) or (10), or twelve or more of the genes in (6), (7), (8), (9) or (10), or fifteen or more of the genes in (6), (7), (8), (9) or (10).

Also provided is a method of determining a subject having a tumor as (i) at risk of metastasis of the tumor, or (ii) at risk of recurrence of the tumor after treatment of the tumor, comprising obtaining a sample of the tumor and determining the level of expression of the following genes (1) CSDE1, PGK1, FAU, SKP1, DAZAP2, NPM1, SUMO1, ARHGDIB, TBCA, WBP5, MSN, S100A11, PTPN11, PRDX3, IMPDH2, RPL19, BTG1, SNTB2, NOLA3, RPL37, UBC, RPS6, SET, STXBP2, ANXA5, NONO, STRBP, PSME2, YWHAE, SNRPD1, DUSP16, UCRC, ALDOA, XRCC5, PMAIP1, IFI16, DGUOK, TUBA3D, DCBLD2, PHACTR2, COX7B, MRPL27, SF3B2, IL8, ERH, LSM3, ATP5I, RPL12, MYL12A, CDC25A, GLO1, TUBA4A, GARS, RPL30, ATP5G1, PKM2, PSMB2, RPL11, SF3B14, NONO, EMP1, OSGEP, SPHK2, RPS24, DDAH1, ILF2, CDC42, SNRPD3, SDHD, FOXM1, RABIF, CALU, NCL, ITGAE, CAV1, PRDX5, DNAJC8, ATP6V0A1, SMAD2, CKS1B, CDC2, DDX24, CAP1, CNN3, NCAPD3, SLC20A1, TXNDC9, UBE2D3, INTS7, CDK3, USP13, ANO6, FMOD, TAF4, ASPH, TRIM32, UTRN, POLR2G, ZNF207, PPM1A, ACVR1B, RFC3, KLF11, ZNF184, ARHGAP11A, VAMP7, FADD, ACAP2, ISLR, and
(2) MLL4, DPP9, SLCO1B3, C8orf79, MDM2, LIMS1, GLUD1, BBS2, CPZ, CCBL1, ZNF814, STEAP2, STK25, IREB2, ZNF165, CEACAM6, NAIP, TRIM13, STAR, CREB1, TSPAN14, ITGB5, SNRP70, MIB2, SLC25A37, SLC16A4, CNN2, CECR1, GP2, SLC45A2, ZNF62I, EPB49, TST, BCL7B, DNASE1, TES, LONP2, RASA4, SGCB, F11, TAS2R20, ZFC3H1, ZNF790, HEBP2, RHOBTB3, DOC2B, MACF1, DLG1, ABCA11P, ZNF331, TTF1, FRG1, PEX2, SLC2A3, RAG 1AP1, ABCD4, PNRC1, MPRIP, IL11, INA, YTHDC1, SLC31A1, KCNJ9, ANKRD11, CORO2A, CPM, IL32, MYO1C, SLC38A2, IL10RB, VDR, NDN, ITGB3BP, HSPB6, POFUT1, SH3BP2, SFXN2, EIF4A1, CDS1, PPF1BP1, S1PR2, RPL37, GTF2I, RRP1, ATP8A1, GATAD2B, NDUFB2, PCYOX1, NUP62, TGFB1I1, ACRBP, TNFRSF9, AKAP13, PIP5K1C, UBR5, SYNC, CHP, GOSR1, PSMD5, ANKRD17, HSDL2, ZNF517 wherein if the level of expression of all of the genes in (1) is upregulated relative to a predetermined control and/or the level of expression of all of the genes in (2) is downregulated relative to a predetermined control, then the subject having the tumor is (i) at risk of metastasis of the tumor, or (ii) at risk of recurrence of the tumor after treatment of the tumor, and wherein if the level of expression of all of the genes in (1) is not upregulated relative to a predetermined control and/or the level of expression of all of the genes in (2) is not downregulated relative to a predetermined control, then the subject having the tumor is not determined to be at risk of metastasis of the tumor, and/or not determined to be at risk of recurrence of a tumor after treatment of the tumor.

In an embodiment, the method comprises determining if the level of expression of at least CSDE1, PGK1, FAU, DAZAP2, NPM1, SUMO1, ARHGDIB, TBCA, WBP5, MSN, S100A11, PTPN11, PRDX3, IMPDH2, RPL19, BTG1, SNTB2, NOP10, RPL37, UBC, RPS6, SET, STXBP2, ANXA5, NONO, STRBP, PSME2, YWHAE, SNRPD1, DUSP16, UCRC, ALDOA, XRCC5, PMAIP1, IFI16, DGUOK, TUBA3D, DCBLD2, PHACTR2, COX7B, MRPL27, SF3B2, IL8, ERH, LSM3, ATP5I, RPL12, MYL12A, CDC25A, GLO1, TUBA4A, GARS, RPL30, ATP5G1, PKM2, PSMB2, RPL11, SF3B14, EMP1, OSGEP, SPHK2, RPS24, DDAH1, ILF2, CDC42, SNRPD3, SDHD, FOXM1, RABIF, CALU, NCL, ITGAE, CAV1, PRDX5, and DNAJC8 is upregulated relative to a predetermined control and if the level of expression of at least (2) GLUD1, LIMS1, MDM2, MLL4, DPP9 is downregulated relative to a predetermined control.

In embodiments of the method, the subject is deemed to be (i) at risk of metastasis of the tumor, or (ii) at risk of recurrence of the tumor after treatment of the tumor, if the level of expression of all of the genes in (1) is upregulated relative to a predetermined control and the level of expression of all of the genes in (2) is downregulated relative to a predetermined control.

In an embodiment of the methods, determining the level of expression of a gene is effected by quantifying a) the level of mRNA transcripts of the gene or b) the level of unique fragments of mRNA transcripts of the gene in the sample. In an embodiment of the methods, quantifying the level of mRNA transcripts of the gene comprises performing a quantitative polymerase chain reaction. In an embodiment of the methods, the subject has previously suffered a metastasis of the tumor, and the method determines whether the subject is at risk of is a distant recurrent metastasis. In an embodiment of the methods, the sample is obtained by micro-needle biopsy.

In an embodiment of the methods, the tumor is a breast cancer tumor. In an embodiment of the methods, the breast cancer tumor is estrogen receptor-negative, progesterone receptor-negative and human epidermal growth factor receptor 2-negative (triple-negative). In an embodiment of the methods, the breast cancer tumor is estrogen receptor-positive. In an embodiment of the methods, the breast cancer tumor is estrogen receptor-negative.

A product is provided comprising one or more microarrays comprising a plurality of oligonucleotide probes for determining the level of expression of the following genes (1): CSDE1, PGK1, FAU, SKP1, DAZAP2, NPM1, SUMO1, ARHGDIB, TBCA, WBP5, MSN, S100A11, PTPN11, PRDX3, IMPDH2, RPL19, BTG1, SNTB2, NOLA3, RPL37, UBC, RPS6, SET, STXBP2, ANXA5, NONO, STRBP, PSME2, YWHAE, SNRPD1, DUSP16, UCRC, ALDOA, XRCC5, PMAIP1, IFI16, DGUOK, TUBA3D, DCBLD2, PHACTR2, COX7B, MRPL27, SF3B2, IL8, ERH, LSM3, ATP5I, RPL12, MYL12A, CDC25A, GLO1, TUBA4A, GARS, RPL30, ATP5G1, PKM2, PSMB2, RPL11, SF3B14, NONO, EMP1, OSGEP, SPHK2, RPS24, DDAH1, ILF2, CDC42, SNRPD3, SDHD, FOXM1, RABIF, CALU, NCL, ITGAE, CAV1, PRDX5, DNAJC8, ATP6V0A1, SMAD2, CKS1B, CDC2, DDX24, CAP1, CNN3, NCAPD3, SLC20A1, TXNDC9, UBE2D3, INTS7, CDK3, USP13, ANO6, FMOD, TAF4, ASPH, TRIM32, UTRN, POLR2G, ZNF207, PPM1A, ACVR1B, RFC3, KLF11, ZNF184, ARHGAP11A, VAMP7, FADD, ACAP2, ISLR.

In an embodiment, at least one oligonucleotide probe of the plurality of probes is specific for each of said genes.

In an embodiment, the one or more microarrays also comprise oligonucleotide probes for determining the level of expression of the following genes (2): MLL4, DPP9, SLCO1B3, C8orf79, MDM2, LIMS1, GLUD1, BBS2, CPZ, CCBL1, ZNF814, STEAP2, STK25, IREB2, ZNF165, CEACAM6, NAIP, TRIM13, STAR, CREB1, TSPAN14, ITGB5, SNRP70, MIB2, SLC25A37, SLC16A4, CNN2, CECR1, GP2, SLC45A2, ZNF621, EPB49, TST, BCL7B, DNASE1, TES, LONP2, RASA4, SGCB, F11, TAS2R20, ZFC3H1, ZNF790, HEBP2, RHOBTB3, DOC2B, MACF1, DLG1, ABCA11P, ZNF331, TTF1, FRG1, PEX2, SLC2A3, RAG1AP1, ABCD4, PNRC1, MPRIP, IL11, INA, YTHDC1, SLC31A1, KCNJ9, ANKRD11, CORO2A, CPM, IL32, MYO1C, SLC38A2, IL10RB, VDR, NDN, ITGB3BP, HSPB6, POFUT1, SH3BP2, SFXN2, EIF4A1, CDS1, PPF1BP1, S1PR2, RPL37, GTF2I, RRP1, ATP8A1, GATAD2B, NDUFB2, PCYOX1, NUP62, TGFB1I1, ACRBP, TNFRSF9, AKAP13, PIP5K1C, UBR5, SYNC, CHP, GOSR1, PSMD5, ANKRD17, HSDL2, ZNF517.

In an embodiment, at least one oligonucleotide probe of the plurality of probes is specific for each of said genes. In an embodiment, the plurality of oligonucleotide probes comprises at least one oligonucleotide probe specific for each of said genes.

A kit is provided for determining (i) risk of metastasis of a tumor in a subject, or (ii) risk of invasion of a tumor, or (iii) risk of recurrence of a tumor after treatment of the tumor in a subject, the kit comprising one or more microarray(s) comprising the product of any of claims 12-14 and instructions for use. In an embodiment, the kit further comprises one or more control samples. In an embodiment, the kit further comprises reverse transcriptase-polymerase chain reaction (RT PCR) reagents.

A method is also provided of inhibiting metastasis of a tumor in a subject, of inhibiting invasion of a tumor in a subject, or of reducing risk of recurrence of a tumor in a subject after treatment of the tumor, comprising administering to the subject an inhibitor of interleukin-8 and/or an inhibitor of phosphatase Shp2 and/or an inhibitor of TGFβ and/or an inhibitor of PTPN11, in an amount effective to inhibit metastasis of a tumor or inhibit invasion of a tumor or duce risk of recurrence of a tumor after treatment of the tumor.

In an embodiment of the method, the inhibitor of interleukin-8 is administered. In an embodiment of the method, the inhibitor of phosphatase Shp2 is administered. In an embodiment of the method, the inhibitor of TGFβ is administered. In an embodiment of the method, the inhibitor of PTPN11 is administered. In an embodiment of the method, the tumor is a breast cancer tumor. In an embodiment of the method, the inhibitor is a small molecule which is an organic molecule of 2000 Daltons or less. In an embodiment, the organic molecule is a molecule comprises at least two carbon-carbon bonds and may comprise inorganic atoms. In an embodiment of the method, the inhibitor is SB431542 or 4-[4-(1,3-benzodioxol-5-yl)-5-(2-pyridinyl)-1H-imidazol-2-yl]benzamide. In an embodiment of the method, the inhibitor is NSC87877 or 8-Hydroxy-7-[(6-sulfo-2-naphthyl)azo]-5-quinolinesulfonic acid. In an embodiment of the method, the inhibitor of interleukin-8 is a monoclonal antibody, or antigen-binding fragment thereof, directed against human interleukin-8. In an embodiment of the method, the inhibitor of phosphatase Shp2 is 8-Hydroxy-7-[(6-sulfo-2-naphthyl)azo]-5-quinolinesulfonic acid (NSC 87877).

A method of treating a cancer in a subject comprising administering, to a subject determined by the method of any of claim 1-11 or 18-25 to be (i) at risk of metastasis of a tumor of the cancer or (ii) at risk of invasion of a tumor, or (iii) at risk of recurrence of a tumor of the cancer after treatment of the tumor, an anti-metastatic therapy or an anti-invasion therapy or an anti-recurrent therapy, respectively, so as to thereby treat the cancer in the subject. In an embodiment of the method, the cancer is a breast cancer. In an embodiment of the method, the subject is a human.

A kit is provided for determining (i) risk of metastasis of a tumor in a subject, or (ii) risk of recurrence of a tumor after treatment of the tumor in a subject, the kit comprising one or more microarray(s) comprising oligonucleotide probes for genes (1): CSDE1, PGK1, FAU, SKP1, DAZAP2, NPM1, SUMO1, ARHGDIB, TBCA, WBP5, MSN, S100A11, PTPN11, PRDX3, IMPDH2, RPL19, BTG1, SNTB2, NOLA3, RPL37, UBC, RPS6, SET, STXBP2, ANXA5, NONO, STRBP, PSME2, YWHAE, SNRPD1, DUSP16, UCRC, ALDOA, XRCC5, PMAIP1, IFI16, DGUOK, TUBA3D, DCBLD2, PHACTR2, COX7B, MRPL27, SF3B2, IL8, ERH, LSM3, ATP5I, RPL12, MYL12A, CDC25A, GLO1, TUBA4A, GARS, RPL30, ATP5G1, PKM2, PSMB2, RPL11, SF3B14, NONO, EMP1, OSGEP, SPHK2, RPS24, DDAH1, ILF2, CDC42, SNRPD3, SDHD, FOXM1, RABIF, CALU, NCL, ITGAE, CAV1, PRDX5, DNAJC8, ATP6V0A1, SMAD2, CKS1B, CDC2, DDX24, CAP1, CNN3, NCAPD3, SLC20A1, TXNDC9, UBE2D3, INTS7, CDK3, USP13, ANO6, FMOD, TAF4, ASPH, TRIM32, UTRN, POLR2G, ZNF207, PPM1A, ACVR1B, RFC3, KLF11, ZNF184, ARHGAP11A, VAMP7, FADD, ACAP2, ISLR, and (2): MLL4, DPP9, SLCO1B3, C8orf79, MDM2, LIMS1, GLUD1, BBS2, CPZ, CCBL1, ZNF814, STEAP2, STK25, IREB2, ZNF165, CEACAM6, NAIP, TRIM13, STAR, CREB1, TSPAN14, ITGB5, SNRP70, MIB2, SLC25A37, SLC16A4, CNN2, CECR1, GP2, SLC45A2, ZNF621, EPB49, TST, BCL7B, DNASE1, TES, LONP2, RASA4, SGCB, F11, TAS2R20, ZFC3H1, ZNF790, HEBP2, RHOBTB3, DOC2B, MACF1, DLG1, ABCA11P, ZNF331, TTF1, FRG1, PEX2, SLC2A3, RAG1AP1, ABCD4, PNRC1, MPRIP, IL11, INA, YTHDC1, SLC31A1, KCNJ9, ANKRD11, CORO2A, CPM, IL32, MYO1C, SLC38A2, IL10RB, VDR, NDN, ITGB3BP, HSPB6, POFUT1, SH3BP2, SFXN2, EIF4A1, CDS1, PPFIBP1, S1PR2, RPL37, GTF2I, RRP1, ATP8A1, GATAD2B, NDUFB2, PCYOX1, NUP62, TGFB1I1, ACRBP, TNFRSF9, AKAP13, PIP5K1C, UBR5, SYNC, CHP, GOSR1, PSMD5, ANKRD17, HSDL2, ZNF517, and a computer system for determining the level of expression of each gene in a sample obtained from the tumor compared to a predetermined control level of expression for each gene, the computer system comprising a processor and a memory encoding one or more programs coupled to the processor, wherein the one or more programs cause the processor to perform a method comprising computing the level of expression of each gene compared to the predetermined control level for each gene, and instructions for use.

A method is also provided of determining a subject having a tumor as (i) at risk of metastasis of the tumor, or (ii) at risk of recurrence of the tumor after treatment of the tumor, comprising obtaining a sample of the tumor and determining the level of expression of one or more of the following gene sets (1) CSDE1, PGK1, FAU, SKP1, DAZAP2, NPM1, SUMO1, ARHGDIB, TBCA, WBP5, MSN, S100A11, PTPN11, PRDX3, IMPDH2, RPL19, BTG1, SNTB2, NOLA3, RPL37, UBC, RPS6, SET, STXBP2, ANXA5, NONO, STRBP, PSME2, YWHAE, SNRPD1, DUSP16, UCRC, ALDOA, XRCC5, PMAIP1, IFI16, DGUOK, TUBA3D, DCBLD2, PHACTR2, COX7B, MRPL27, SF3B2, IL8, ERH, LSM3, ATP5I, RPL12, MYL12A, CDC25A, GLO1, TUBA4A, GARS, RPL30, ATP5G1, PKM2, PSMB2, RPL11, SF3B14, NONO, EMP1, OSGEP, SPHK2, RPS24, DDAH1, ILF2, CDC42, SNRPD3, SDHD, FOXM1, RABIF, CALU, NCL, ITGAE, CAV1, PRDX5, DNAJC8, ATP6V0A1, SMAD2, CKS1B, CDC2, DDX24, CAP1, CNN3, NCAPD3, SLC20A1, TXNDC9, UBE2D3, INTS7, CDK3, USP13, ANO6, FMOD, TAF4, ASPH, TRIM32, UTRN, POLR2G, ZNF207, PPM1A, ACVR1B, RFC3, KLF11, ZNF184, ARHGAP11A, VAMP7, FADD, ACAP2, ISLR, and (2): MLL4, DPP9, SLCO1B3, C8orf79, MDM2, LIMS1, GLUD1, BBS2, CPZ, CCBL1, ZNF814, STEAP2, STK25, IREB2, ZNF165, CEACAM6, NAIP, TRIM13, STAR, CREB1, TSPAN14, ITGB5, SNRP70, MIB2, SLC25A37, SLC16A4, CNN2, CECR1, GP2, SLC45A2, ZNF621, EPB49, TST, BCL7B, DNASE1, TES, LONP2, RASA4, SGCB, F11, TAS2R20, ZFC3H1, ZNF790, HEBP2, RHOBTB3, DOC2B, MACF1, DLG1, ABCA11P, ZNF331, TTF1, FRG1, PEX2, SLC2A3, RAG1AP1, ABCD4, PNRC1, MPRIP, IL11, INA, YTHDC1, SLC31A1, KCNJ9, ANKRD11, CORO2A, CPM, IL32, MYO1C, SLC38A2, IL10RB, VDR, NDN, ITGB3BP, HSPB6, POFUT1, SH3BP2, SFXN2, EIF4A1, CDS1, PPFIBP1, S1PR2, RPL37, GTF2I, RRP1, ATP8A1, GATAD2B, NDUFB2, PCYOX1, NUP62, TGFB1I1, ACRBP, TNFRSF9, AKAP13, PIP5K1C, UBR5, SYNC, CHP, GOSR1, PSMD5, ANKRD17, HSDL2, ZNF517, wherein if the level of expression of genes in (1) is upregulated relative to a predetermined control and/or the level of expression of genes in (2) is downregulated relative to a predetermined control, then the subject having the tumor is (i) at risk of metastasis of the tumor, or (ii) at risk of recurrence of the tumor after treatment of the tumor, and wherein if the level of expression of genes in (1) is not upregulated relative to a predetermined control and the level of expression of genes in (2) is not downregulated relative to a predetermined control, then the subject having the tumor is not determined to be at risk of metastasis of the tumor, and/or not determined to be at risk of recurrence of a tumor after treatment of the tumor.

A kit is also provided for determining (i) risk of metastasis of a tumor in a subject, or (ii) risk of recurrence of a tumor after treatment of the tumor in a subject, the kit comprising one or more microarray(s) comprising oligonucleotide probes for genes (1): CSDE1, PGK1, FAU, SKP1, DAZAP2, NPM1, SUMO1, ARHGDIB, TBCA, WBP5, MSN, S100A11, PTPN11, PRDX3, IMPDH2, RPL19, BTG1, SNTB2, NOLA3, RPL37, UBC, RPS6, SET, STXBP2, ANXA5, NONO, STRBP, PSME2, YWHAE, SNRPD1, DUSP16, UCRC, ALDOA, XRCC5, PMAIP1, IFI16, DGUOK, TUBA3D, DCBLD2, PHACTR2, COX7B, MRPL27, SF3B2, IL8, ERH, LSM3, ATP5I, RPL12, MYL12A, CDC25A, GLO1, TUBA4A, GARS, RPL30, ATP5G1, PKM2, PSMB2, RPL11, SF3B14, NONO, EMP1, OSGEP, SPHK2, RPS24, DDAH1, ILF2, CDC42, SNRPD3, SDHD, FOXM1, RABIF, CALU, NCL, ITGAE, CAV1, PRDX5, DNAJC8, ATP6V0A1, SMAD2, CKS1B, CDC2, DDX24, CAP1, CNN3, NCAPD3, SLC20A1, TXNDC9, UBE2D3, INTS7, CDK3, USP13, ANO6, FMOD, TAF4, ASPH, TRIM32, UTRN, POLR2G, ZNF207, PPM1A, ACVR1B, RFC3, KLF11, ZNF184, ARHGAP11A, VAMP7, FADD, ACAP2, ISLR, and (2): MLL4, DPP9, SLCO1B3, C8orf79, MDM2, LIMS1, GLUD1, BBS2, CPZ, CCBL1, ZNF814, STEAP2, STK25, IREB2, ZNF165, CEACAM6, NAIP, TRIM13, STAR, CREB1, TSPAN14, ITGB5, SNRP70, MIB2, SLC25A37, SLC16A4, CNN2, CECR1, GP2, SLC45A2, ZNF621, EPB49, TST, BCL7B, DNASE1, TES, LONP2, RASA4, SGCB, F11, TAS2R20, ZFC3H1, ZNF790, HEBP2, RHOBTB3, DOC2B, MACF1, DLG1, ABCA11P, ZNF331, TTF1, FRG1, PEX2, SLC2A3, RAG1AP1, ABCD4, PNRC1, MPRIP, IL11, INA, YTHDC1, SLC31A1, KCNJ9, ANKRD11, CORO2A, CPM, IL32, MYO1C, SLC38A2, IL10RB, VDR, NDN, ITGB3BP, HSPB6, POFUT1, SH3BP2, SFXN2, EIF4A1, CDS1, PPFIBP1, S1PR2, RPL37, GTF2I, RRP1, ATP8A1, GATAD2B, NDUFB2, PCYOX1, NUP62, TGFB1I1, ACRBP, TNFRSF9, AKAP13, PIP5K1C, UBR5, SYNC, CHP, GOSR1, PSMD5, ANKRD17, HSDL2, ZNF517, and a computer system for determining the level of expression of each gene in a sample obtained from the tumor compared to a predetermined control level of expression for each gene, the computer system comprising a processor and a memory encoding one or more programs coupled to the processor, wherein the one or more programs cause the processor to perform a method comprising computing the level of expression of each gene compared to the predetermined control level for each gene, and instructions for use.

A method is provided of inhibiting metastasis of a tumor in a subject, or reducing risk of recurrence of a tumor in a subject after treatment of the tumor, comprising administering to the subject an inhibitor of a gene product of one or more of the following CSDE1, PGK1, FAU, SKP1, DAZAP2, NPM1, SUMO1, ARHGDIB, TBCA, WBP5, MSN, S100A11, PTPN11, PRDX3, IMPDH2, RPL19, BTG1, SNTB2, NOLA3, RPL37, UBC, RPS6, SET, STXBP2, ANXA5, NONO, STRBP, PSME2, YWHAE, SNRPD1, DUSP16, UCRC, ALDOA, XRCC5, PMAIP1, IFI16, DGUOK, TUBA3D, DCBLD2, PHACTR2, COX7B, MRPL27, SF3B2, IL8, ERH, LSM3, ATP5I, RPL12, MYL12A, CDC25A, GLO1, TUBA4A, GARS, RPL30, ATP5G1, PKM2, PSMB2, RPL11, SF3B14, NONO, EMP1, OSGEP, SPHK2, RPS24, DDAH1, ILF2, CDC42, SNRPD3, SDHD, FOXM1, RABIF, CALU, NCL, ITGAE, CAV1, PRDX5, DNAJC8, ATP6V0A1, SMAD2, CKS1B, CDC2, DDX24, CAP1, CNN3, NCAPD3, SLC20A1, TXNDC9, UBE2D3, INTS7, CDK3, USP13, ANO6, FMOD, TAF4, ASPH, TRIM32, UTRN, POLR2G, ZNF207, PPM1A, ACVR1B, RFC3, KLF11, ZNF184, ARHGAP11A, VAMP7, FADD, ACAP2, ISLR, and/or an activator of a gene product of one or more of the following: MLL4, DPP9, SLCO1B3, C8orf79, MDM2, LIMS1, GLUD1, BBS2, CPZ, CCBL1, ZNF814, STEAP2, STK25, IREB2, ZNF165, CEACAM6, NAIP, TRIM13, STAR, CREB1, TSPAN14, ITGB5, SNRP70, MIB2, SLC25A37, SLC16A4, CNN2, CECR1, GP2, SLC45A2, ZNF621, EPB49, TST, BCL7B, DNASE1, TES, LONP2, RASA4, SGCB, F11, TAS2R20, ZFC3H1, ZNF790, HEBP2, RHOBTB3, DOC2B, MACF1, DLG1, ABCA11P, ZNF331, TTF1, FRG1, PEX2, SLC2A3, RAG1AP1, ABCD4, PNRC1, MPRIP, IL11, INA, YTHDC1, SLC31A1, KCNJ9, ANKRD11, CORO2A, CPM, IL32, MYO1C, SLC38A2, IL10RB, VDR, NDN, ITGB3BP, HSPB6, POFUT1, SH3BP2, SFXN2, EIF4A1, CDS1, PPFIBP1, S1PR2, RPL37, GTF2I, RRP1, ATP8A1, GATAD2B, NDUFB2, PCYOX1, NUP62, TGFB1I1, ACRBP, TNFRSF9, AKAP13, PIP5K1C, UBR5, SYNC, CHP, GOSR1, PSMD5, ANKRD17, HSDL2, ZNF517, in an amount effective to inhibit metastasis of the tumor in the subject or reduce risk of recurrence of a tumor in the subject after treatment of the tumor.

A method is provided of determining a subject having a tumor as (i) at risk of metastasis of the tumor, or (ii) at risk of recurrence of the tumor after treatment of the tumor, comprising obtaining a sample of the tumor and determining the level of expression of the following genes (1) CSDE1, PGK1, FAU, DAZAP2, NPM1, SUMO1, ARHGDIB, TBCA, WBP5, MSN, S100A11, PTPN11, PRDX3, IMPDH2, RPL19, BTG1, SNTB2, NOP10, RPL37, UBC, RPS6, SET, STXBP2, ANXA5, NONO, STRBP, PSME2, YWHAE, SNRPD1, DUSP16, UCRC, ALDOA, XRCC5, PMAIP1, IFI16, DGUOK, TUBA3D, DCBLD2, PHACTR2, COX7B, MRPL27, SF3B2, IL8, ERH, LSM3, ATP5I, RPL12, MYL12A, CDC25A, GLO1, TUBA4A, GARS, RPL30, ATP5G1, PKM2, PSMB2, RPL11, SF3B14, EMP1, OSGEP, SPHK2, RPS24, DDAH1, ILF2, CDC42, SNRPD3, SDHD, FOXM1, RABIF, CALU, NCL, ITGAE, CAV1, PRDX5, and DNAJC8, and (2) GLUD1, LIMS1, MDM2, MLL4, DPP9 wherein if the level of expression of all of the genes in (1) is upregulated relative to a predetermined control and the level of expression of all of the genes in (2) is downregulated relative to a predetermined control, then the subject having the tumor is (i) at risk of metastasis of the tumor, or (ii) at risk of recurrence of the tumor after treatment of the tumor, and wherein if the level of expression of all of the genes in (1) is not upregulated relative to a predetermined control and the level of expression of all of the genes in (2) is not downregulated relative to a predetermined control, then the subject having the tumor is not determined to be at risk of metastasis of the tumor, and/or not determined to be at risk of recurrence of a tumor after treatment of the tumor.

A method is provided of determining a subject having a tumor as (i) at risk of metastasis of the tumor, or (ii) at risk of recurrence of the tumor after treatment of the tumor, comprising determining in a sample previously obtained from the tumor the level of expression of the following genes using a microarray having one or more probes for each of the following genes (1) CSDE1, PGK1, FAU, SKP1, DAZAP2, NPM1, SUMO1, ARHGDIB, TBCA, WBP5, MSN, S100A11, PTPN11, PRDX3, IMPDH2, RPL19, BTG1, SNTB2, NOLA3, RPL37, UBC, RPS6, SET, STXBP2, ANXA5, NONO, STRBP, PSME2, YWHAE, SNRPD1, DUSP16, UCRC, ALDOA, XRCC5, PMAIP1, IFI16, DGUOK, TUBA3D, DCBLD2, PHACTR2, COX7B, MRPL27, SF3B2, IL8, ERH, LSM3, ATP5I, RPL12, MYL12A, CDC25A, GLO1, TUBA4A, GARS, RPL30, ATP5G1, PKM2, PSMB2, RPL1, SF3B14, NONO, EMP1, OSGEP, SPHK2, RPS24, DDAH1, ILF2, CDC42, SNRPD3, SDHD, FOXM1, RABIF, CALU, NCL, ITGAE, CAV1, PRDX5, DNAJC8, ATP6V0A1, SMAD2, CKS1B, CDC2, DDX24, CAP1, CNN3, NCAPD3, SLC20A1, TXNDC9, UBE2D3, INTS7, CDK3, USP13, ANO6, FMOD, TAF4, ASPH, TRIM32, UTRN, POLR2G, ZNF207, PPM1A, ACVR1B, RFC3, KLF11, ZNF184, ARHGAP11A, VAMP7, FADD, ACAP2, ISLR, and (2) MLL4, DPP9, SLCO1B3, C8orf79, MDM2, LIMS1, GLUD1, BBS2, CPZ, CCBL1, ZNF814, STEAP2, STK25, IREB2, ZNF165, CEACAM6, NAIP, TRIM13, STAR, CREB1, TSPAN14, ITGB5, SNRP70, MIB2, SLC25A37, SLC16A4, CNN2, CECR1, GP2, SLC45A2, ZNF621, EPB49, TST, BCL7B, DNASE1, TES, LONP2, RASA4, SGCB, F11, TAS2R20, ZFC3H1, ZNF790, HEBP2, RHOBTB3, DOC2B, MACF1, DLG1, ABCA11P, ZNF331, TTF1, FRG1, PEX2, SLC2A3, RAG1AP1, ABCD4, PNRC1, MPRIP, IL11, INA, YTHDC1, SLC31A1, KCNJ9, ANKRD11, CORO2A, CPM, IL32, MYO1C, SLC38A2, IL10RB, VDR, NDN, ITGB3BP, HSPB6, POFUT1, SH3BP2, SFXN2, EIF4A1, CDS1, PPFIBP1, S1PR2, RPL37, GTF2I, RRP1, ATP8A1, GATAD2B, NDUFB2, PCYOX1, NUP62, TGFB1I1, ACRBP, TNFRSF9, AKAP13, PIP5K1C, UBR5, SYNC, CHP, GOSR1, PSMD5, ANKRD17, HSDL2, ZNF517 wherein if the level of expression of all of the genes in (1) is upregulated relative to a predetermined control and/or the level of expression of all of the genes in (2) is downregulated relative to a predetermined control, then the subject having the tumor is (i) at risk of metastasis of the tumor, or (ii) at risk of recurrence of the tumor after treatment of the tumor, and wherein if the level of expression of all of the genes in (1) is not upregulated relative to a predetermined control and/or the level of expression of all of the genes in (2) is not downregulated relative to a predetermined control, then the subject having the tumor is not determined to be at risk of metastasis of the tumor, and/or not determined to be at risk of recurrence of a tumor after treatment of the tumor.

In an embodiment of any of the methods disclosed herein, determining the level of expression of a gene is effected by quantifying the level of mRNA transcripts of the gene or the level of unique fragments of mRNA transcripts of the gene in the sample. In an embodiment, quantifying the level of mRNA transcripts of the gene comprises performing a quantitative polymerase chain reaction.

In an embodiment of any of the methods disclosed herein, the subject has previously suffered a metastasis of the tumor, and the method determines whether the subject is at risk of is a distant recurrent metastasis. In an embodiment, the sample is obtained by micro-needle biopsy. In an embodiment of any of the methods disclosed herein, the tumor is a breast cancer tumor. In an embodiment, the breast cancer tumor is estrogen receptor-negative, progesterone receptor-negative and human epidermal growth factor receptor 2-negative (triple-negative). In an embodiment, the breast cancer tumor is estrogen receptor-positive. In an embodiment, the breast cancer tumor is estrogen receptor-negative.

In an embodiment of the methods herein, the inhibitor of interleukin-8 is administered. In an embodiment, the inhibitor of phosphatase Shp2 is administered. In an embodiment, the inhibitor of TGFβ is administered. In an embodiment, the tumor is a breast cancer tumor. In an embodiment, the inhibitor is a small molecule inhibitor which is an organic molecule of 2000 Daltons or less. As used herein a "small organic molecule" is an organic compound which contains carbon-carbon bonds, and has a molecular weight of less than 2000. The small molecule may be a substituted hydrocarbon or an substituted hydrocarbon. In an embodiment, the small molecule has a molecular weight of less than 1500. In an embodiment, the small molecule has a molecular weight of less than 1000. In an embodiment, the inhibitor of interleukin-8 is a monoclonal antibody, or antigen-binding fragment thereof, directed against human interleukin-8. In an embodiment, the inhibitor of phosphatase Shp2 is 8-Hydroxy-7-[(6-sulfo-2-naphthyl)azo]-5-quinolinesulfonic acid (NSC 87877). In an embodiment, the inhibitor of TGFβ is 4-[4-(1,3-benzodioxol-5-yl)-5-(2-pyridinyl)-1H-imidazol-2-yl]benzamide (SB431542). In an embodiment, the cancer is a breast cancer. In an embodiment of the methods disclosed herein, the subject is a human. In an embodiment, the inhibitor is administered in an amount effective to treat the cancer or to inhibit the metastasis.

In an embodiment, the product comprises one microarray comprising oligonucleotide probes for both (1) and (2). In an embodiment, the product comprises one microarray comprising oligonucleotide probes for (1) and one microarray comprising oligonucleotide probes for (2).

In an embodiment, being determined "at risk of metastasis" of a tumor by performance of the method means that the subject is expected to have metastasis of the tumor within five years after being determined as "at risk" by performance of the method on the subject. In an embodiment, being determined "at risk of invasion" of a tumor by performance of the method means that the subject is expected to have invasion of the tumor within five years after being determined as "at risk" by performance of the method on the subject. In an embodiment, being determined "at risk of recurrence" of a tumor by performance of the method means that the subject is expected to have recurrence of a tumor within five years after treatment of the tumor in the subject. At risk is understood in one embodiment to mean to be in a position of greater propensity (than one not at risk) of experiencing the relevant event, for example, metastasis, invasion or recurrence. In this regard, publications in the art refer to populations or subjects identified as at risk so as to distinguish the population from those not identified to be at risk, especially due to the presence or absence of the particular relevant factor. In an embodiment, at risk means more likely to than not.

In an embodiment of the methods described herein the expression level of genes can be determined from the level of the corresponding gene-derived polynucleotide. "Gene-derived polynucleotide" means the RNA transcribed from a gene, such as a mRNA, or any cDNA or cRNA produced therefrom, and any nucleic acid derived therefrom, such as a synthetic nucleic acid having a sequence derived from the gene sequence.

A sample may comprise any clinically relevant tissue sample, such as a tumor biopsy or fine needle aspirate, or a sample of bodily fluid, such as blood, plasma, serum, lymph, ascitic fluid, cystic fluid, urine or nipple exudate, or a sample obtained by methods such as lysis, centrifugation or separation of the tissue. The sample may be taken from a human subject, or, in a veterinary context, from non-human subjects such as ruminants, horses, swine or sheep, or from domestic companion animals such as felines and canines. In an embodiment the sample is a tumor biopsy or fine needle aspirate. The sample may be treated for use.

In an embodiment a control is provided, wherein the control is standardized or normalized (e.g. derived from a normal population which is, for example, free of cancer), or is a standard human reference value, e.g. mRNA level. The control amount or value can be predetermined, e.g. mathematically, or empirically. The concept of a control is well-established in the field, and can be determined, in a non-limiting example, empirically from non-afflicted subjects (versus afflicted subjects), or from, for example, samples of tumors which have not metastasized over a control time (versus tumors which have), as is relevant. The control amount or value may be normalized to negate the effect of one or more variables.

If desired, where expression level of the genes is measured as mRNA levels or as levels of a molecule or marker derived from mRNA, such as a cDNA, the mRNA in the sample can be enriched with respect to other cellular RNAs, such as transfer RNA (tRNA) and ribosomal RNA (rRNA). Most mRNAs contain a poly(A) tail at their 3' end. This allows them to be enriched by affinity chromatography, for example, using oligo(dT) or poly(U) coupled to a solid support, such as cellulose or Sephadex™ (see Ausubel et al., CURRENT PROTOCOLS IN MOLECULAR BIOLOGY, vol. 2, Current Protocols Publishing, New York (1994), hereby incorporated by reference). Once bound, poly(A)+ mRNA is eluted from the affinity column using 2 mM EDTA/0.1% SDS. Methods for preparing total and poly(A)+ RNA are well known and are described generally in Sambrook et al., MOLECULAR CLONING—A LABORATORY MANUAL (2ND ED.), Vols. 1-3, Cold Spring Harbor Laboratory, Cold Spring Harbor, N.Y. (1989)) and Ausubel et al., CURRENT PROTOCOLS IN MOLECULAR BIOLOGY, vol. 2, Current Protocols Publishing, New York (1994)), the contents of both of which are incorporated herein. RNA may be isolated from samples of eukaryotic cells by procedures that involve lysis of the cells and denaturation of the proteins contained therein. Additional steps may be employed to remove DNA. Cell lysis may be accomplished with a nonionic detergent, followed by microcentrifugation to remove the nuclei and hence the bulk of the cellular DNA. In one embodiment, RNA is extracted from cells of the various types of interest using guanidinium thiocyanate lysis followed by CsCl centrifugation to separate the RNA from DNA (Chirgwin et al., Biochemistry 18:5294-5299 (1979) hereby incorporated by reference). Poly(A)+ RNA can be selected by selection with oligo-dT cellulose (see Sambrook et al, MOLECULAR CLONING—A LABORATORY MANUAL (2ND ED.), Vols. 1-3, Cold Spring Harbor Laboratory, Cold Spring Harbor, N.Y. (1989). Alternatively, separation of RNA from DNA can be accomplished by organic extraction, for example, with hot phenol or phenol/chloroform/isoamyl alcohol. If desired, RNase inhibitors may be added to the lysis buffer. Likewise, for certain cell types, it may be desirable to add a protein denaturation/digestion step to the protocol. Methods of preparing cDNA from mRNA are well-known in the art.

In one embodiment, the method of determining a metastatic risk of a tumor or risk of recurrence of a tumor of a subject comprises the steps of (1) hybridizing sample, or sample-derived, target polynucleotides from the subject to a microarray containing one of the above gene probe sets described herein; (2) hybridizing standard or control polynucleotides molecules to the microarray, wherein the standard or control molecules are differentially labeled from the target polynucleotides; and (3) determining the difference in transcript levels, if any, between the target and standard or control, wherein the difference, or lack thereof, determines the metastatic risk of a tumor, or risk of recurrence of a tumor of the subject.

The predetermined control levels of expression are chosen or determined from an appropriate control. In an embodiment, the standard or control molecules (or predetermined control levels) comprise gene-derived polynucleotides (or levels determined) from a pool of samples from normal individuals. In an embodiment the normal individuals do not have a cancer. In an embodiment the normal individuals do not have a breast cancer. In an embodiment, the standard or control molecules (or predetermined control levels) comprise gene-derived polynucleotides (or levels determined) from a pool of samples from individuals having a tumor/cancer, but wherein the tumor/cancer is deemed not at risk of metastasis.

In an embodiment, the microarray comprises probes attached via surface engineering to a solid surface by a covalent bond to a chemical matrix (via, in non-limiting examples, epoxy-silane, amino-silane, lysine, polyacrylamide). Suitable solid surface can be, in non-limiting examples, glass or a silicon chip, a solid bead forms of for example, polystyrene. As used herein, unless otherwise specified, a microarray includes both solid-phase microarrays and bead microarrays. In an embodiment, the microarray is a solid-phase microarray. In an embodiment, the microarray is a plurality of beads microarray. In an embodiment, the microarray is a spotted microarray. In an embodiment, the microarray is an oligonucleotide microarray. The oligonucleotide probes of the microarray may be of any convenient length necessary for unique discrimination of targets. In non limiting examples, the oligonucleotide probes are 20 to 30 nucleotides in length, 31 to 40 nucleotides in length, 41 to 50 nucleotides in length, 51 to 60 nucleotides in length, 61 to 70 nucleotides in length, or 71 to 80 nucleotides in length. In an embodiment, the target sample, or nucleic acids derived from the target sample, such as mRNA or cDNA, are contacted with a detectable marker, such as one or more fluorophores, under conditions permitting the fluorophore to attach to the target sample or nucleic acids derived from the target sample. In non-limiting examples the fluorophores are cyanine 3, cyanine 5. In an embodiment, the target hybridized to the probe can be detected by conductance, MS, electrophoresis etc. The microarray can be manufactured by any method known in the art including by photolithography, pipette, drop-touch, piezoelectric (ink-jet), and electric techniques.

As used herein an "anti-metastatic" therapy is any art-recognized therapy used to reduce the incidence of metastasis in an individual. In an embodiment, the metastasis is of a primary tumor. Anti-metastatic therapy includes an agent that attenuates, reduces or prevents one or more symptoms or one or more other parameters by which metastasis is characterized. Non-limiting examples of such parameters include uncontrolled degradation of the basement membrane and proximal extracellular matrix, and travel of tumor cells through the bloodstream or lymphatics, invasion, dysregulated adhesion, and proliferation at a secondary site.

As used herein an "anti-invasion" therapy is any art-recognized therapy used to reduce the incidence of tumor invasion in an individual. As used herein, "invasion" of a tumor means progression of the tumor such as to a site immediately adjacent to the origin site of the tumor. This contrasts with metastasis which involves spread of tumor distal to the origin site.

As used herein an "anti-recurrent" therapy is any art-recognized therapy used to reduce the recurrence of a cancer or of a tumor type in an individual. As used herein, "recurrence" of a tumor, means a later recurrence of the tumor in the same location in the individual, or a later recurrence of the same tumor type.

"And/or" as used herein, for example, with option A and/or option B, encompasses the embodiments of (i) option A, (ii) option B, and (iii) option A plus option B.

The methods described herein can be used, mutatis mutandis, with regard to protein levels. Accordingly, proteins encoded by the genes of interest herein can be isolated from the foregoing sources, by methods known in the art, for use in expression analysis at the protein level.

In an embodiment of the methods or kits described herein, all of the genes are human genes.

All combinations of the various elements described herein are within the scope of the invention unless otherwise indicated herein or otherwise clearly contradicted by context.

This invention will be better understood from the Experimental Details, which follow. However, one skilled in the art will readily appreciate that the specific methods and results discussed are merely illustrative of the invention as described more fully in the claims that follow thereafter.

EXPERIMENTAL DETAILS

Example 1

Introduction

Using novel assays, herein is identified a gene expression profile specific for invasion and dissemination in tumors, such as human primary breast tumors. Unsupervised analysis (i.e. an analysis which imports no knowledge about the samples being analyzed other than the expression data) of this human invasion signature shows that the migratory breast tumor cells use embryonic development gene networks in order to migrate, invade and intravasate inside the primary tumor, with TGF signaling being a central regulator of these upregulated phenotypes. In addition, this human invasion signature can significantly predict risk of metastasis in public breast cancer databases independently of breast cancer subtype. The importance of selected target genes for in vivo invasion and tumor cell dissemination, namely Interleukin-8 and PTPN11, was functionally verified using both cell line and patient derived primary breast tumors. This gene expression profile identified is of value for determining prognosis and for therapy in cancers, including breast cancer invasion and metastasis.

Results

Gene expression profile of migratory human tumor cells in vivo: the human invasion signature. Since the focus of this study was to analyze the migration and invasion properties of tumor cells in a model of metastatic human breast cancer, MDA-MB-231 human breast tumor cells were used as an orthotopic xenograft in immunodeficient mice to begin, and further analysis was performed in patient-derived xenograft tumors. MDA-MB-231 is an ATCC established breast adenocarcinoma cell line, resembling basal-like breast cancer (12), that is widely used by the scientific community for studying in vivo metastasis because of its ability to grow orthotopic tumors in mice that spontaneously metastasize to the lungs. It has previously been shown that the migratory cells can be collected from MDAMB-231 primary tumors in response to epidermal growth factor (EGF) or colony stimulating factor-1 (CSF-1) using an in vivo invasion assay (13,14). This assay tests the cells' ability in vivo to chemotax toward a chemokine gradient, to invade through the solid tumor matrix and finally migrate over long distances toward the source of the gradient 15. The tumor cells collected with this assay will be hereafter called for brevity "migratory tumor cells". Using this assay, it has been shown that the invasive properties of the MDA-MB-231 human breast adenocarcinoma cells are different in vitro and in vivo, due to a TGFβ-initiated autocrine CSF-1/CSF-1R loop that happens only in the tumor microenvironment (14). This emphasizes the importance of isolating the migratory tumor cells directly from the primary tumor in viva, to understand their full potential and characteristics.

Using the in vivo invasion assay, migratory tumor cells were isolated from the MDA-MB-231 primary tumors and then their gene expression profile compared by microarray analysis to the total or "average" primary tumor cell population, which is primarily non-migratory and resident cells (see FIG. 5). Orthotopic xenografts of human MDA-MB-231-GFP breast adenocarcinoma cells were made in SCID mice. Migratory cells were isolated with the in vivo invasion assay, where cells are stimulated to migrate towards an EGF gradient and through a matrigel gel. The average primary tumor cells (APTCs) were isolated by FACS sorting for live GFP-positive cells from a whole tumor cell preparation. Both populations are tumor cells by more than 95% purity: invasive cells from MDA-MB-231 tumors consist 95% tumor cells (Patsialou et al., 2009), and the purity of the APTCs was determined by post-sort FACS analysis. RNA was extracted from both the purified cell populations and used for microarray analysis after amplification. A total of 6 biological repeats were used per sample for the analysis (discussed further in Materials and Methods). In addition, the conditions of cell collection were controlled for to ensure that the invasion gene signature for the tumor cells is independent of the cell collection method. Three additional biological repeats of APTCs were used that we treated with matrigel and EGF inside needles, to mimic the conditions of the in vivo invasion assay. These control samples were used for RNA extraction, amplification, hybridization and quantification in exactly the same method as the experimental samples. Statistical analysis of the control samples versus the APTCs gave a list of genes upregulated solely due to the matrigel/EGF stimulation. These genes were subtracted from the final signature, so that the Invasion Signature would account for the gene profile of the breast tumor cells while they migrate and invade in viva through the tumor microenvironment, and not the cell collection method. Additional controls performed in previous studies for this assay, to exclude that the migration measured in this assay is not a result of local inflammation because of the insertion of the microneedles, are: a). in vivo invasion assay in normal mammary tissue showed no significant migration to the gradient; and b). in vivo invasion assay in mammary primary tumors in the absence of a chemotactic gradient (only matrigel in the microneedles) shows no significant migration. Overall, 185 annotated genes with known protein products were significantly altered in the migratory tumor cells (see Table 1). Herein this gene list is also referred to as the human invasion signature (HIS).

In order to discover tissue trophic functions of the migratory breast tumor cells, Ingenuity Pathway Analysis (IPA) was used first to rank enriched function categories of gene networks relating to the transcripts regulated in the HIS. Table 1 shows the top five most significantly upregulated and downregulated functions related to the gene networks of the HIS, along with the list of the corresponding genes per function network.

TABLE 1

Significant upregulated and downregulaled functions of the invasive human tumor cells. This is a subset of the HIS genes that fall into the functions indicated.

Upregulated

Rank -1; Score - 48; Type - DNA Replication and Repair
ALDOA, CDC25A, CDK1, CKS1B, CSDE1, DAZAP2, DBP, EMP1, FOXM1, IFI16, NCL,
NONO, NPM1, PMAIP1, POLR2G, PTAFR, S100A11, SET, SF3B2, SKP1, SLC20A1,
TRIM32, UBC TABLE 1-continued Significant upregulated and downregulated functions of the invasive human tumor cells. This is a subset of the HIS genes that fall into the functions indicated.

2; 36; Embryonic and Tissue Development
ACVR1B, ARHGDIB, CAP1, CAV1, CDC42, DDX24, FADD, GLO1, IL8, KLF11, LSM3, MSN,
NCAPD3, PPM1A, PTPN11, RPS6, SMAD2, SNRPD1, SNRPD3, SNTB2, UTRN, VAMP7,
XRCC5, YWHAE
3; 33; Cellular Movement and Development
ARHGAP11A, CNN3, ITGAE, MRPL27, OSGEP, PHACTR2, PRDX5, RFC3, RPL30, RPL37,
RPL12, SNRPD3, TUBA1A, TUBA4A, TXNDC9, UBE2D3, ZNF184
4; 33; Cell-to-Cell Signaling and Interaction
ACAP2, ASPH, CALU, COX7B, GARS, IMPDH2, ISLR, NOP10, PRDX3, RABIF, RPL11.
RPL19, SDHD, STRBP, USP13, WBP5, ZNF207
5; 27; Cellular Assembly and Organization
ATP5G1, ATP5I, ATP6V0A1, DDAH1, DGUOK, ERH, FMOD, MYL12A, PSMB2, PSME2,
SF3B14, STXBP2, TBCA, UQCR10, VAMP7
Downregulated Rank - 1; Score - 44; Nervous System Development and Function
AKAP13, BBS2, CEACAM6, CHP, CREB1, DLG1, HSPB6, IL11, IL32, INA, ITGB3BP, NUP62,
PNRC1, S1PR2, SH3BP2, SLC2A3, SLCO1B3, STAR, TNFRSF9, TRIM13, VDR
2; 31; Cell death and Cell Cycle
ACRBP, ATP8A1, BCL7B, DOC2B, GOSR1, IREB2, MIB2, NDUFB2, PSMD5, RASA4, RPL37,
SLC2A3, TGFB1I1, TNF, TP53I3, TP53INP1, TST, TTF1, YTHDC1
3; 22; Hematological Disease
CHP, CNN2, F11, FRG1, GATAD2B, HSDL2, KCNJ9, POFUT1, SGCB, TSPAN14, ZFC3H1,
ZNF165
4; 19; Protein Synthesis and Cell Morphology
EIF4A1, EPB49, HEBP2, MACF1, MLL4, MPRIP, MYO1C, RAGIAP1, TES, UBR5, ZNF790
5; 18; Drug and Nucleic Acid Metabolism
IL10RB, MDM2, NAIP, PIP5K1C, PPFIBP1, SLC25A37, SLC2A3, SLC38A2, SNRNP70, STK25,
ZNF331

The most highly upregulated gene networks in the migratory tumor cells control the functions of DNA replication and repair, embryonic and tissue development, and cellular movement. Interestingly, an independent study of tumor-associated macrophages (TAM) has recently shown that invasive macrophages isolated from primary mammary tumors of transgenic mice also demonstrate a resemblance in their genetic profile to embryonic macrophages when compared to the general TAM population (16). These data suggest that a recapitulation of expression of embryonic gene pathways is adopted by the breast tumor cells and their partner macrophages during invasion and migration in primary tumors.

In the functions that are downregulated in the migratory tumor cells, cell cycle and cell death were among the most significant (Table 1). This result is consistent with previous results from this lab that showed that invasive cells isolated from a transgenic mouse mammary tumor showed decreased proliferation and apoptosis compared to the average primary tumor cells, resulting in an increased resistance to chemotherapy (17).

Figures 1A, 1B, 1C, 1D:
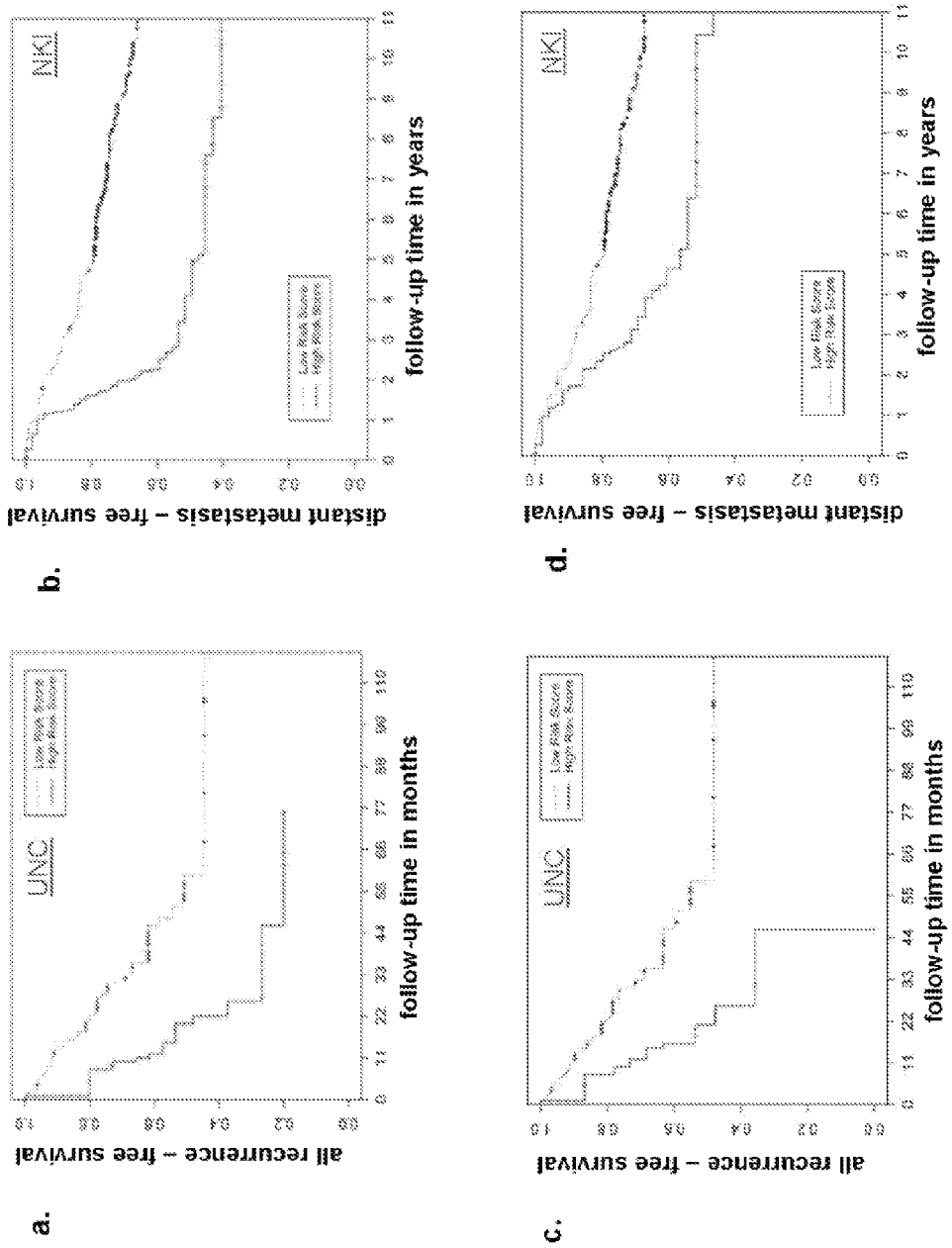
FIG. 1A-1D: The human invasion signature is significantly correlated with risk of recurrence and metastasis in breast cancer patients. Expression of the top regulated genes in the human invasion signature was correlated with the disease outcomes of breast cancer patients in public microarray databases using the Cox proportional hazards model. (1A). The Invasion signature is significantly correlated with increased risk of disease recurrence in the UNC patient database. p-value for log-rank test p=0.000. (1B). The invasion signature is significantly correlated with increased risk of distant metastasis in the NKI patient database.

The human invasion signature has prognostic value in breast cancer patients. To determine whether the HIS has prognostic value in determining metastatic risk for patients with breast cancer a Cox proportional hazards model analysis was performed to investigate the association between recurrence-free or metastasis-free survival and the gene expression profiles of the HIS for breast cancer patients from publicly available databases. Two databases were analyzed, one from a UNC cohort study (18) and one from a NKI cohort study (3). Expression of the genes in the HIS significantly separated breast cancer patients with increased risk of overall recurrence and distant metastasis in the UNC and the NKI cohorts respectively (FIGS. 1A-1B and FIGS. 6A+6B). This suggests that the migratory cells that were analyzed in this study are the tumor cells that will most likely invade and disseminate to form distant metastasis in patients. Therefore patients with enriched numbers of these cells in their primary tumors are at higher risk for developing metastasis or recurrence.

Since the microarray analysis was based on MDA-MB-231 orthotopic tumors, which is a triple negative basal-like breast cancer cell line 12, a concern may be that the signature is prognostic because it simply groups the basal patients which are known to have a worse outcome (19). However, if the high-risk groups are subdivided from the above analysis in both the NKI and UNC cohorts by breast cancer subtype, one can see patients of all subtypes (except for Normal subtypes) were classified as high-risk with the gene list (FIG. 6C). This suggests that the HIS was not prognostic simply because it identified the basal patients. To further investigate this, the Cox proportional hazards model analysis was repeated, completely excluding the basal patients from both cohorts, and again it was found that the HIS was prognostic of recurrence and metastasis in the patients of all remaining subtypes (FIGS. 1C and 1D). Finally, a correlation analysis was performed of the HIS pattern to the gene expression of individual patients in the UNC cohort (method as performed previously in reference 20), and found that the signature does not correlate significantly with any single breast cancer subtype.

Validation of Specific Genes from the Human Invasion Signature

The gene expression changes found in the HIS were validated by real-time PCR in independent biological repeats of migratory tumor cells and average primary tumor cells isolated from MDA-MB-231 tumors. Experiments concentrated on the genes of the three most significantly upregulated functional networks identified by IPA: DNA replication and repair, embryonic and tissue development, and cellular movement (Table 1). These genes will be most likely to have central roles in invasion and metastasis of the breast tumor cells, and therefore most likely to be more useful and more relevant as potential future prognostic markers and/or therapeutic targets. Upregulation of the majority of these genes with the independent biological repeats was confirmed and in most cases the fold change of the mRNA expression was actually under-represented in the DNA microarrays (FIG. 2). Some of the upregulated genes confirmed here have well established roles in invasion and metastasis, such as SMAD2 (21), CDC42 (22) and VAMP7 (23). Other genes have been correlated with carcinogenesis, such as CDC25A (24), PTPN11 (25) and IL8 (26), but have not been studied in invasion and metastasis of breast cancer. Of additional interest, some of the genes confirmed here are completely novel to the roles of cancer and metastasis, such as DAZAP2 and KLF11. Interestingly, DAZAP2 is essential for neural patterning in *Xenopus laevis* embryos (27) and KLF11 is an activator of embryonic and fetal beta-like globin genes (28), again pointing to a connection between regulation of embryonic development and cancer invasion. Overall, the HIS has identified novel genes that could potentially have important roles in the regulation of invasion and migration inside primary breast tumors.

The TGFβ pathway is a central regulator of the gene profile of the invasive breast tumor cells. To determine which canonical pathways were most highly enriched in the genetic profile of the migratory invasive breast tumor cells an IPA and GSEA analysis was performed of the HIS with known curated canonical pathway gene lists. Both software programs gave similar results, with many metabolism and cytoskeleton regulating pathways being enriched in the signature (Table 2 and FIG. 8).

Gene networks of the three most highly upregulated functions of the invasive tumor cells (as discovered by CPA, shown in Table 1) were investigated using the IPA software to map the interactions of the proteins encoded by these genes. Indeed, TGFβ is a central node of the interactions between these gene networks. NFκB and VEGF were also implicated as central nodes of interaction, but these were not identified by IPA or GSEA as significantly enriched pathways (Table 2 and FIG. 8). Therefore, TGFβ signaling appears to be a central and significantly enriched signaling regulator of the major function networks of the migratory human breast tumor cells.

Development of Orthotopic Patient-Derived Breast Tumors in Mice

Since most of the above described study was performed in xenografts derived from the MDA-MB-231 cell line, the results were verified in patient-derived primary tumors and thus further validate their clinical significance. A panel of xenografts from patient-derived breast tumor tissue was developed, collected from surgical resections and orthotopically implanted in the mammary fat pad of mice. In total over 30 patient breast tumor tissue samples were implanted in mice, with a growth take rate of approximately 28% (detailed information about the take rate and the histological properties of the patient samples can be found in Tables 3 and 4).

TABLE 2

GSEA analysis of the human invasion signature was performed compared to the KEGG list of gene sets (available at the GSEA Molecular Signatures database). Shown are the pathways designated by the software as significant based on FDR <25%.

| Gene set | Size | Enrichment Score | Normalized Enrichment Score | Nominal p-value |
|---|---|---|---|---|
| HSA00190_OXIDATIVE_PHOSPHORYLATION | 72 | 0.53593624 | 1.6825051 | 0 |
| HSA00240_PYRIMIDINE_METABOLISM | 45 | 0.45250845 | 1.5814575 | 0 |
| HSA00230_PURINE_METABOLISM | 67 | 0.39516756 | 1.470321 | 0 |
| HSA03020_RNA_POLYMERASE | 15 | 0.564014 | 1.4446641 | 0 |
| HSA04350_TGF_BETA_SIGNALING_PATHWAY | 52 | 0.33286476 | 1.3473384 | 0.010615711 |
| HSA00970_AMINOACYL_TRNA_BIOSYNTHESIS | 18 | 0.50897855 | 1.4736814 | 0.01984127 |
| HSA00010_GLYCOLYSIS_AND_GLUCONEOGENESIS | 31 | 0.50495917 | 1.5837573 | 0.0256917 |
| HSA03010_RIBOSOME | 29 | 0.72607535 | 1.6891521 | 0.026422765 |
| HSA05120_EPITHELIAL_CELL_SIGNALING_IN_HELICOBACTER_PYLORI_INFECTION | 34 | 0.48527545 | 1.5133995 | 0.029350106 |
| HSA04115_P53_SIGNALING_PATHWAY | 30 | 0.4093354 | 1.473076 | 0.030800821 |
| HSA00620_PYRUVATE_METABOLISM | 17 | 0.5118131 | 1.4412352 | 0.035714287 |
| HSA00252_ALANINE_AND_ASPARTATE_METABOLISM | 15 | 0.4375976 | 1.4436632 | 0.050200805 |
| HSA04810_REGULATION_OF_ACTIN_CYTOSKELETON | 86 | 0.37577453 | 1.4934524 | 0.065126054 |
| HSA00590_ARACHIDONIC_ACID_METABOLISM | 22 | 0.44838226 | 1.3874453 | 0.06889353 |
| HSA04110_CELL_CYCLE | 62 | 0.39508766 | 1.4528823 | 0.09375 |

Interestingly, both analyses designated the TGFβ pathway as being highly enriched in the migratory tumor cells, a pathway that is consistent with an "embryonic state" for these cells while in the process of migration (29,30). TGFβ is known to be crucial to tumor progression, but also to the development of the normal mammary gland 31. It has also recently been shown that TGFβ is the macroenvironmental factor that initiates an autocrine invasion phenotype for the human breast tumor cells by upregulating the expression of the colony-stimulating factor-1 receptor (CSF-1R) in the MDA-MB-231 breast tumor cells in vivo (14). Other groups have also shown the importance of transient TGFβ signaling upon tumor migration, heterogeneity and progression (32-35).

TABLE 3

Number of samples implanted and take rates for the mouse implantation.

| | Total | ER+ | ER− | Triple Negative |
|---|---|---|---|---|
| Patient samples received: | 29 | 17 | 12 | 7 |
| Samples that grew tumors: | 8 | 4 | 4 | 4 |
| Take rate: | 27.59% | 23.53% | 33.33% | 57.14% |

TABLE 4

Pathological characteristics of the patient tumors that successfully grew a tumor in mice in first passage.

| sample ID | pathological diagnosis | grade | ER | PR | Her2 | AJCC stage |
|---|---|---|---|---|---|---|
| HT1 | Invasive ductal carcinoma | HG-9 | neg | neg | neg | T2N1micMx |
| HT3 | Invasive lobular carcinoma, pleomorphic type | n/a | pos | pos | neg | T1bN0Mx |
| HT17 | Invasive ductal carcinoma | HG-9 | neg | neg | neg | T4bN0Mx |
| HT24 | Invasive ductal carcinoma | HG-8 | pos | pos | neg | T1cN0(i+)Mx |
| HT30 | Invasive ductal carcinoma | HG-9 | pos | <2% | neg | T2N0Mx |
| HT33 | Invasive ductal carcinoma | HG-9 | pos | neg | neg | T2N0Mx |
| HT34 | Invasive ductal carcinoma | HG-9 | neg | neg | neg | T1cN0Mx |
| HT39 | Invasive ductal carcinoma | HG-8 | neg | neg | neg | T4dNxMx |

Other studies of implantation of patient breast tumor tissue have reported somewhat higher take rates. However, these were not orthotopic but used subcutaneous sites or the abdominal fat pad as implantation sites (36,37). The mammary fat pad was used as an implantation site in order to have a more relevant microenvironment for breast tumor growth and a clinically relevant route for invasion and dissemination of the migratory human breast cancer cells. In summary, it was found that triple-negative (TN) breast tumors had a superior engraftment rate, as well as propagation and metastatic properties in the mice (Tables 3-5).

TABLE 5

Growth, passage and metastatic characteristics of the tumor xenografts.

| sample ID | latency | passage in mice | migration to FBS or EGF | lung metastasis |
|---|---|---|---|---|
| HT1 | 9 months | yes | yes | yes (4/8mice) |
| HT3 | 4 months | no | n/a | n/a |
| HT17 | 2 months | yes | yes | yes (4/8mice) |
| HT24 | 5 months | no | n/a | n/a |
| HT30 | 6 months | yes | yes | yes (1/4mice) |
| HT33 | 3 months | yes | no | no (0/6 mice) |
| HT34 | 4 months | no | n/a | n/a |
| HT39 | 3 months | yes | yes | yes (5/8mice) |

It was also found that the estrogen receptor (ER)-positive (ER+) tumors lost their ER expression very quickly after growth in the mouse, generally by passage 1 or 2 (even when the mice were supplemented with estrogen), making it technically challenging to work with ER+ tumors for this specific study (data not shown). Overall, the in vivo invasion assay could be used to collect migratory tumor cells from both TN and ER+ types of patient-derived primary breast tumors, with again the triple-negative tumors having an advantage for higher numbers of migratory cells than the ER+ tumors (FIG. 3A and Table 5). As this study focused on invasion in the primary tumor of metastatic breast cancer, it was chosen to focus on human tumor samples HT17 and HT39, which were found to be both invasive (FIG. 3A) and metastatic in the mouse (FIG. 3C and Table 5). It was confirmed that even after up to four passages in mice these tumors remained human in origin, their histology was similar to the patient (FIG. 3B) and that their invasive potential remained the same throughout the passages. Therefore, it was concluded that the patient-derived breast primary tumors HT17 and HT39 were suitable models for further validation of specific genes from the HIS in patient material.

Functional Validation of Specific Genes from the Human Invasion Signature in Patient-Derived Breast Tumors.

Given that TGFβ was found to be a central regulator of the most significant phenotypes of the invasive tumor cells (FIG. 3), the effect of inhibiting TGFβ was determined in invasion and intravasation of the human breast tumor cells in vivo. SB431542 was used, a small molecule specific inhibitor of the TGFβ receptor (14,38), which was injected into the tumor-bearing mice prior to measurements of invasion and intravasation. Invasion was measured by count of the total cells that chemotax and invade in the primary tumor towards a gradient source (EGF or FBS) with the in vivo invasion assay. Intravasation and dissemination was measured by count of the circulating tumor cells in the total blood of tumorbearing mice. Indeed, it was found that inhibition of TGFβ signaling could effectively abrogate both invasion and tumor cell dissemination, in the MDA-MB-231 tumors as well as in the patient-derived HT17 and HT39 tumors (FIG. 4A).

Also investigated was the role of specific genes from the HIS in invasion and tumor cell dissemination of the human breast tumors. The two most upregulated genes according to our real-time PCR validation (FIG. 2) are IL8 and PTPN11, with a 56-fold and 80-fold upregulation in the migratory tumor cells respectively. Both IL8 and PTPN11 were categorized by IPA in the tissue development function (Table 1), but their roles in invasion and metastasis of breast cancer has not been directly explored. IL8 (Interleukin-8 or CXCL8) was originally cloned as a monocyte-derived factor capable of attracting and activating neutrophils, eosinophils and T lymphocytes (26). In breast cancer, IL8 has been shown to promote invasion of breast tumor cell lines through reconstituted matrices in vitro (39,40), and to enhance angiogenesis in vivo, an effect thought to happen mainly through the recruitment of neutrophils to the primary tumor 26. PTPN11 (which encodes for the phosphatase Shpt) was first found as a gene of which germline mutations are linked to the developmental disorder syndromes Noonan and LEOPARD (41). Somatic mutations in this gene are also associated with several types of human malignancies, most notably juvenile myelomonocytic leukemia (41,42). In relation to the mammary gland, a conditional deletion of PTPN11 in transgenic mice showed impaired mammary gland development and morphogenesis of the alveolar structures (43).

The role of these two genes in in vivo invasion and dissemination of breast tumor cells was tested by injecting into tumor-bearing mice either a specific neutralizing antibody to human IL8 or a specific small molecule inhibitor to PTPN11, NSC87877. Blocking of either IL8 or PTPN11 significantly abrogated invasion in the primary tumors, as well as dissemination of the tumor cells in the blood stream, in the MDA-MB-231 tumors, as well as in the patient-derived HT17 and HT39 tumors (FIG. 4B, 4C). It is therefore identified here for the first time that in vivo IL8 and PTPN11 are key mediators for invasion and dissemination of tumor cells in human breast cancer.

Results for top 80 genes upregulated or downregulated are shown in Table 6:

| UniGene ID | Gene Symbol | Dot info | Fold Change |
| --- | --- | --- | --- |
| Hs.69855 | CSDE1 | N76338 | 6.4668 |
| Hs.701989 | PGK1 | AA599187 | 5.5217 |
| Hs.387208 | FAU | AA316067 | 4.6375 |
| Hs.369761 | DAZAP2 | R19889 | 4.3699 |
| Hs.557550 | NPM1 | W44488 | 4.3202 |
| Hs.621179 | SUMO1 | BG529395 | 3.8619 |
| Hs.504877 | ARHGDIB | N91838 | 3.4972 |
| Hs.291212 | TBCA | W21373 | 3.3315 |
| Hs.533287 | WBP5 | H96654 | 3.3265 |
| Hs.87752 | MSN | R22977 | 3.3206 |
| Hs.417004 | S100A11 | AA464731 | 3.3023 |
| Hs.506852 | PTPN11 | AA465603 | 3.2784 |
| Hs.523302 | PRDX3 | H19203 | 3.2424 |
| Hs.654400 | IMPDH2 | BF316301 | 3.1980 |
| Hs.381061 | RPL19 | BF691720 | 3.1803 |
| Hs.255935 | BTG1 | N70463 | 3.0838 |
| Hs.461117 | SNTB2 | N59766 | 3.0679 |
| Hs.14317 | NOP10 | AA464531 | 3.0538 |
| Hs.558601 | RPL37 | AW969881 | 2.9766 |
| Hs.520348 | UBC | AU160779 | 2.9737 |
| Hs.408073 | RPS6 | N91584 | 2.9252 |
| Hs.436687 | SET | AA608548 | 2.8876 |
| Hs.515104 | STXBP2 | R93237 | 2.7784 |
| Hs.658778 | ANXA5 | AA451895 | 2.7708 |
| Hs.533282 | NONO | BE384419 | 2.7324 |
| Hs.696159 | STRBP | N53133 | 2.6670 |
| Hs.434081 | PSME2 | BG387808 | 2.6008 |
| Hs.513851 | YWHAE | N21624 | 2.5719 |
| Hs.464734 | SNRPD1 | H16454 | 2.5708 |
| Hs.536535 | DUSP16 | AI807619 | 2.5480 |
| Hs.284292 | UCRC | AA447731 | 2.5477 |
| Hs.513490 | ALDOA | AA775241 | 2.5427 |
| Hs.388739 | XRCC5 | AA775355 | 2.5292 |
| Hs.96 | PMAIP1 | BG392214 | 2.5191 |
| Hs.380250 | IFI16 | AA491191 | 2.4972 |
| Hs.469022 | DGUOK | R07560 | 2.4487 |
| Hs.503749 | TUBA3D | AA626698 | 2.4255 |
| Hs.701630 | DCBLD2 | AA431438 | 2.4227 |
| Hs.654921 | PHACTR2 | W58563 | 2.4023 |
| Hs.92236 | MLL4 | AA625915 | 0.2944 |
| Hs.515081 | DPP9 | AA011400 | 0.3543 |
| Hs.522699 | COX7B | AA629999 | 2.3994 |
| Hs.7736 | MRPL27 | BG328180 | 2.3879 |
| Hs.406423 | SF3B2 | AA633757 | 2.3872 |
| Hs.632880 | IL8 | AA102526 | 2.3714 |
| Hs.509791 | ERH | BG504520 | 2.3529 |
| Hs.111632 | LSM3 | AA461098 | 2.3464 |
| Hs.85539 | ATP5I | AA431433 | 2.3406 |
| Hs.408054 | RPL12 | BG282851 | 2.3347 |
| Hs.190086 | MYL12A | AA345289 | 2.3071 |
| Hs.437705 | CDC25A | R09063 | 2.2909 |
| Hs.268849 | GLO1 | AA136710 | 2.2855 |
| Hs.75318 | TUBA4A | AA180912 | 2.2755 |
| Hs.404321 | GARS | AA629909 | 2.2707 |
| Hs.400295 | RPL30 | AA775364 | 2.2407 |
| Hs.80986 | ATP5G1 | AA046701 | 2.2334 |
| Hs.534770 | PKM2 | AW007619 | 2.2315 |
| Hs.471441 | PSMB2 | T98663 | 2.2270 |
| Hs.388664 | RPL11 | AA680244 | 2.2245 |
| Hs.177861 | SF3B14 | N22302 | 2.2051 |
| Hs.436298 | EMP1 | N92872 | 2.1852 |
| Hs.525196 | OSGEP | AA421311 | 2.1816 |
| Hs.528006 | SPHK2 | AA630354 | 2.1812 |
| Hs.356794 | RPS24 | AI005519 | 2.1566 |
| Hs.379858 | DDAH1 | N24042 | 2.1459 |
| Hs.75117 | ILF2 | AU135389 | 2.1417 |
| Hs.567303 | MDM2 | U33199 | 0.4660 |
| Hs.690198 | CDC42 | AA668681 | 2.1270 |

-continued

| UniGene ID | Gene Symbol | Dot info | Fold Change |
| --- | --- | --- | --- |
| Hs.356549 | SNRPD3 | BF220008 | 2.1199 |
| Hs.356270 | SDHD | AA035384 | 2.1078 |
| Hs.239 | FOXM1 | AI150022 | 2.0950 |
| Hs.90875 | RABIF | U74324 | 2.0710 |
| Hs.7753 | CALU | R78585 | 2.0672 |
| Hs.79110 | NCL | AU123684 | 2.0166 |
| Hs.655316 | LIMS1 | AA024832 | 0.4952 |
| Hs.513867 | ITGAE | AV762515 | 1.9796 |
| Hs.74034 | CAV1 | BG541572 | 1.9716 |
| Hs.502823 | PRDX5 | N91311 | 1.9583 |
| Hs.433540 | DNAJC8 | W37375 | 1.9480 |
| Hs.500409 | GLUD1 | N68424 | 0.5059 |

Results for genes upregulated are shown in Table 7:

| UniGene ID | Gene Symbol | Dot info | Fold Change |
| --- | --- | --- | --- |
| Hs.69855 | CSDE1 | N76338 | 6.47 |
| Hs.701989 | PGK1 | AA599187 | 5.52 |
| Hs.387208 | FAU | AA316067 | 4.64 |
| Hs.171626 | SKP1 | BG334963 | 4.46 |
| Hs.369761 | DAZAP2 | R19889 | 4.37 |
| Hs.557550 | NPM1 | W44488 | 4.32 |
| Hs.621179 | SUMO1 | BG529395 | 3.86 |
| Hs.504877 | ARHGDIB | N91838 | 3.50 |
| Hs.291212 | TBCA | W21373 | 3.33 |
| Hs.533287 | WBP5 | H96654 | 3.33 |
| Hs.87752 | MSN | R22977 | 3.32 |
| Hs.417004 | S100A11 | AA464731 | 3.30 |
| Hs.506852 | PTPN11 | AA465603 | 3.28 |
| Hs.523302 | PRDX3 | H19203 | 3.24 |
| Hs.654400 | IMPDH2 | BF316301 | 3.20 |
| Hs.381061 | RPL19 | BF691720 | 3.18 |
| Hs.255935 | BTG1 | N70463 | 3.08 |
| Hs.461117 | SNTB2 | N59766 | 3.07 |
| Hs.14317 | NOLA3 | AA464531 | 3.05 |
| Hs.654400 | IMPDH2 | AA996028 | 2.99 |
| Hs.558601 | RPL37 | AW969881 | 2.98 |
| Hs.520348 | UBC | AU160779 | 2.97 |
| Hs.408073 | RPS6 | N91584 | 2.93 |
| Hs.436687 | SET | AA608548 | 2.89 |
| Hs.515104 | STXBP2 | R93237 | 2.78 |
| Hs.658778 | ANXA5 | AA451895 | 2.77 |
| Hs.533282 | NONO | BE384419 | 2.73 |
| Hs.696159 | STRBP | N53133 | 2.67 |
| Hs.557550 | NPM1 | AA669758 | 2.64 |
| Hs.434081 | PSME2 | BG387808 | 2.60 |
| Hs.513851 | YWHAE | N21624 | 2.57 |
| Hs.464734 | SNRPD1 | H16454 | 2.57 |
| Hs.536535 | DUSP16 | AI807619 | 2.55 |
| Hs.284292 | UCRC | AA447731 | 2.55 |
| Hs.513490 | ALDOA | AA775241 | 2.54 |
| Hs.388739 | XRCC5 | AA775355 | 2.53 |
| Hs.96 | PMAIP1 | BG392214 | 2.52 |
| Hs.380250 | IFI16 | AA491191 | 2.50 |
| Hs.469022 | DGUOK | R07560 | 2.45 |
| Hs.503749 | TUBA3D | AA626698 | 2.43 |
| Hs.701630 | DCBLD2 | AA431438 | 2.42 |
| Hs.654921 | PHACTR2 | W58563 | 2.40 |
| Hs.522699 | COX7B | AA629999 | 2.40 |
| Hs.7736 | MRPL27 | BG328180 | 2.39 |
| Hs.406423 | SF3B2 | AA633757 | 2.39 |
| Hs.632880 | IL8 | AA102526 | 2.37 |
| Hs.509791 | ERH | BG504520 | 2.35 |
| Hs.111632 | LSM3 | AA461098 | 2.35 |
| Hs.85539 | ATP5I | AA431433 | 2.34 |
| Hs.408054 | RPL12 | BG282851 | 2.33 |
| Hs.190086 | MYL12A | AA345289 | 2.31 |
| Hs.504877 | ARHGDIB | AA487634 | 2.30 |
| Hs.437705 | CDC25A | R09063 | 2.29 |
| Hs.268849 | GLO1 | AA136710 | 2.29 |
| Hs.75318 | TUBA4A | AA180912 | 2.28 |
| Hs.404321 | GARS | AA629909 | 2.27 |
| Hs.400295 | RPL30 | AA775364 | 2.24 |
| Hs.80986 | ATP5G1 | AA046701 | 2.23 |

| UniGene ID | Gene Symbol | Dot info | Fold Change |
|---|---|---|---|
| Hs.534770 | PKM2 | AW007619 | 2.23 |
| Hs.471441 | PSMB2 | T98663 | 2.23 |
| Hs.388664 | RPL11 | AA680244 | 2.22 |
| Hs.190086 | MYL12A | BG434307 | 2.22 |
| Hs.177861 | SF3B14 | N22302 | 2.21 |
| Hs.533282 | NONO | AA056465 | 2.19 |
| Hs.388739 | XRCC5 | AU139370 | 2.19 |
| Hs.436298 | EMP1 | N92872 | 2.19 |
| Hs.525196 | OSGEP | AA421311 | 2.18 |
| Hs.528006 | SPHK2 | AA630354 | 2.18 |
| Hs.356794 | RPS24 | AI005519 | 2.16 |
| Hs.379858 | DDAH1 | N24042 | 2.15 |
| Hs.75117 | ILF2 | AU135389 | 2.14 |
| Hs.690198 | CDC42 | AA668681 | 2.13 |
| Hs.356549 | SNRPD3 | BF220008 | 2.12 |
| Hs.356270 | SDHD | AA035384 | 2.11 |
| Hs.239 | FOXM1 | AI150022 | 2.10 |
| Hs.90875 | RABIF | U74324 | 2.07 |
| Hs.7753 | CALU | R78585 | 2.07 |
| Hs.79110 | NCL | AU123684 | 2.02 |
| Hs.513867 | ITGAE | AV762515 | 1.98 |
| Hs.74034 | CAV1 | BG541572 | 1.97 |
| Hs.502823 | PRDX5 | N91311 | 1.96 |
| Hs.433540 | DNAJC8 | W37375 | 1.95 |
| Hs.463074 | ATP6V0A1 | AA427472 | 1.85 |
| Hs.598146 | SMAD2 | AA081871 | 1.81 |
| Hs.374378 | CKS1B | AA459292 | 1.80 |
| Hs.334562 | CDC2 | BG033634 | 1.77 |
| Hs.510328 | DDX24 | H93249 | 1.77 |
| Hs.370581 | CAP1 | BG286995 | 1.71 |
| Hs.700591 | CNN3 | AA043228 | 1.69 |
| Hs.438550 | NCAPD3 | AK025549 | 1.66 |
| Hs.187946 | SLC20A1 | W47073 | 1.66 |
| Hs.536122 | TXNDC9 | AA085749 | 1.66 |
| Hs.557550 | NPM1 | AL547236 | 1.64 |
| Hs.518773 | UBE2D3 | AA017199 | 1.64 |
| Hs.522699 | COX7B | AV695162 | 1.63 |
| Hs.369285 | INTS7 | N80458 | 1.61 |
| Hs.593566 | CDK3 | NM_001258 | 1.60 |
| Hs.591319 | USP13 | AA211448 | 1.60 |
| Hs.696326 | ANO6 | N31270 | 1.56 |
| Hs.519168 | FMOD | AL551623 | 1.55 |
| Hs.18857 | TAF4 | AA487148 | 1.53 |
| Hs.622998 | ASPH | S83325 | 1.51 |
| Hs.591910 | TRIM32 | BC003154 | 1.51 |
| Hs.133135 | UTRN | NM_007124 | 1.49 |
| Hs.14839 | POLR2G | AA477428 | 1.49 |
| Hs.500775 | ZNF207 | BE383414 | 1.48 |
| Hs.592298 | PPM1A | NM_021003 | 1.44 |
| Hs.438918 | ACVR1B | NM_004302 | 1.44 |
| Hs.115474 | RFC3 | H94617 | 1.42 |
| Hs.12229 | KLF11 | NM_003597 | 1.40 |
| Hs.158174 | ZNF184 | AA455712 | 1.40 |
| Hs.591130 | ARHGAP11A | NM_014783 | 1.39 |
| Hs.24167 | VAMP7 | R27644 | 1.37 |
| Hs.86131 | FADD | AA430751 | 1.35 |
| Hs.654597 | ACAP2 | AA490493 | 1.33 |
| Hs.513022 | ISLR | H62387 | 1.31 |

Results for genes downregulated are shown in Table 8:

| UniGene ID | Gene Symbol | Dot info | Fold Change |
|---|---|---|---|
| Hs.92236 | MLL4 | AA625915 | 0.29 |
| Hs.515081 | DPP9 | AA011400 | 0.35 |
| Hs.92236 | MLL4 | BE410539 | 0.42 |
| Hs.504966 | SLCO1B3 | H75435 | 0.45 |
| Hs.202521 | C8orf79 | R97970 | 0.45 |
| Hs.567303 | MDM2 | U33199 | 0.47 |
| Hs.655316 | LIMS1 | AA024832 | 0.50 |
| Hs.500409 | GLUD1 | N68424 | 0.51 |
| Hs.333738 | BBS2 | N93740 | 0.52 |
| Hs.78068 | CPZ | AA427724 | 0.52 |
| Hs.495250 | CCBL1 | H92216 | 0.52 |
| Hs.644595 | ZNF814 | H90946 | 0.53 |
| Hs.489051 | STEAP2 | N52554 | 0.53 |
| Hs.516807 | STK25 | BE278206 | 0.54 |
| Hs.436031 | IREB2 | BF002434 | 0.54 |
| Hs.535177 | ZNF165 | W31899 | 0.54 |
| Hs.466814 | CEACAM6 | AA130584 | 0.55 |
| Hs.646951 | NAIP | H21071 | 0.56 |
| Hs.436922 | TRIM13 | R07594 | 0.56 |
| Hs.521535 | STAR | AA679454 | 0.56 |
| Hs.584750 | CREB1 | H12320 | 0.57 |
| Hs.310453 | TSPAN14 | AA158352 | 0.57 |
| Hs.380164 | ITGB5 | H54393 | 0.58 |
| Hs.654500 | NAIP | NM_004536 | 0.58 |
| Hs.467097 | SNRP70 | R02346 | 0.58 |
| Hs.135805 | MIB2 | AA021134 | 0.58 |
| Hs.122514 | SLC25A37 | AA046639 | 0.59 |
| Hs.351306 | SLC16A4 | R73003 | 0.59 |
| Hs.651512 | CNN2 | AA284568 | 0.59 |
| Hs.170310 | CECR1 | R98295 | 0.60 |
| Hs.696648 | GP2 | AA844930 | 0.60 |
| Hs.278962 | SLC45A2 | N23139 | 0.60 |
| Hs.19977 | ZNF621 | H63518 | 0.60 |
| Hs.106124 | EPB49 | N55461 | 0.60 |
| Hs.474783 | TST | AA446748 | 0.60 |
| Hs.647051 | BCL7B | AA291513 | 0.60 |
| Hs.657504 | DNASE1 | R91033 | 0.61 |
| Hs.592286 | TES | T52325 | 0.61 |
| Hs.295923 | LONP2 | T71889 | 0.62 |
| Hs.696339 | RASA4 | AA663075 | 0.62 |
| Hs.438953 | SGCB | W81563 | 0.62 |
| Hs.1430 | F11 | R89539 | 0.62 |
| Hs.686384 | TAS2R20 | N24163 | 0.63 |
| Hs.527874 | ZFC3H1 | AA609585 | 0.63 |
| Hs.282067 | ZNF790 | AA151111 | 0.63 |
| Hs.486589 | HEBP2 | T68113 | 0.63 |
| Hs.690933 | RHOBTB3 | AA010222 | 0.63 |
| Hs.654162 | CPM | AA487192 | 0.63 |
| Hs.648240 | DOC2B | NM_003585 | 0.63 |
| Hs.580782 | MACF1 | AI017174 | 0.63 |
| Hs.292549 | DLG1 | H48711 | 0.64 |
| Hs.428360 | ABCA11P | H91281 | 0.64 |
| Hs.185674 | ZNF331 | N71714 | 0.64 |
| Hs.54780 | TTF1 | AA709143 | 0.64 |
| Hs.203772 | FRG1 | AA113339 | 0.64 |
| Hs.437966 | PEX2 | R88992 | 0.64 |
| Hs.419240 | SLC2A3 | AI148702 | 0.64 |
| Hs.292154 | RAG1AP1 | AV703538 | 0.64 |
| Hs.94395 | ABCD4 | R07661 | 0.65 |
| Hs.75969 | PNRC1 | BG435213 | 0.65 |
| Hs.462341 | MPRIP | N31673 | 0.65 |
| Hs.467304 | IL11 | NM_000641 | 0.65 |
| Hs.500916 | INA | BE781432 | 0.65 |
| Hs.175955 | YTHDC1 | N99803 | 0.65 |
| Hs.532315 | SLC31A1 | BG248634 | 0.66 |
| Hs.66726 | KCNJ9 | NM_004983 | 0.66 |
| Hs.335003 | ANKRD11 | N67832 | 0.66 |
| Hs.113094 | CORO2A | BC000010 | 0.66 |
| Hs.654387 | CPM | NM_001874 | 0.66 |
| Hs.943 | IL32 | AA458965 | 0.66 |
| Hs.500409 | GLUD1 | AA018372 | 0.67 |
| Hs.286226 | MYO1C | BE395925 | 0.67 |
| Hs.221847 | SLC38A2 | N94529 | 0.67 |
| Hs.654593 | IL10RB | T48767 | 0.67 |
| Hs.524368 | VDR | AA485226 | 0.68 |
| Hs.50130 | NDN | XM_007686 | 0.68 |
| Hs.166539 | ITGB3BP | H56981 | 0.68 |
| Hs.534538 | HSPB6 | AA284108 | 0.68 |
| Hs.472409 | POFUT1 | T91958 | 0.68 |
| Hs.167679 | SH3BP2 | R48132 | 0.68 |
| Hs.44070 | SFXN2 | AA476258 | 0.68 |
| Hs.129673 | EIF4A1 | AV756187 | 0.69 |
| Hs.654899 | CDS1 | AI635747 | 0.69 |
| Hs.172445 | PPFIBP1 | AA459403 | 0.69 |
| Hs.655405 | S1PR2 | AA460965 | 0.69 |
| Hs.80545 | RPL37 | W73010 | 0.69 |
| Hs.702022 | GTF2I | H70120 | 0.69 |
| Hs.110757 | RRP1 | AL526119 | 0.69 |
| Hs.435052 | ATP8A1 | T61475 | 0.69 |

-continued

| UniGene ID | Gene Symbol | Dot info | Fold Change |
| --- | --- | --- | --- |
| Hs.4779 | GATAD2B | R16112 | 0.69 |
| Hs.655788 | NDUFB2 | AA055474 | 0.70 |
| Hs.591572 | PCYOX1 | N45309 | 0.70 |
| Hs.574492 | NUP62 | NM_016553 | 0.71 |
| Hs.513530 | TGFB1I1 | AA454619 | 0.71 |
| Hs.123239 | ACRBP | AA443593 | 0.71 |
| Hs.654459 | TNFRSF9 | BG436824 | 0.71 |
| Hs.459211 | AKAP13 | AA147202 | 0.71 |
| Hs.282177 | PIP5K1C | AA482251 | 0.71 |
| Hs.591856 | UBR5 | W86992 | 0.72 |
| Hs.696281 | SYNC | T91057 | 0.72 |
| Hs.406234 | CHP | AA705060 | 0.72 |
| Hs.699303 | GOSR1 | AA481414 | 0.72 |
| Hs.193725 | PSMD5 | AA113407 | 0.73 |
| Hs.601206 | ANKRD17 | H61608 | 0.73 |
| Hs.59486 | HSDL2 | R01179 | 0.73 |
| Hs.521942 | ZNF517 | H51438 | 0.74 |

Discussion

In this study, a unique invasion gene signature for human breast cancer was derived. The results show that the migratory human breast tumor cells resemble in their mRNA expression cells of embryonic and tissue development, and that TGFβ signaling is a central regulator for the upregulated embryonic and migratory phenotypes. Expression of the human invasion signature also significantly associates with recurrence-free or metastasis-free survival in breast cancer patients, independent of molecular subtype. Finally, it is shown herein to show that blocking specific genes derived from this signature led to significant abrogation of invasion and tumor cell dissemination in both MDA-MB-231-derived and patient tissue-derived primary breast tumors. In the past, an invasion signature was identified in MTLn3 rat mammary tumor xenografts and MMTV-PyMT transgenic mammary tumor mice (44,45); however the human invasion signature consists of a unique gene list that is not evident in the rat and mouse tumor models. As an example, IL8, which was functionally validated herein as an important mediator of invasion and tumor cell dissemination in the human breast tumors in vivo, does not have a clear homolog in mice and rats and therefore was not previously discovered using the rodent models.

An added value of the human invasion signature is that it is specific to the initial steps of the metastatic cascade, migration and invasion inside the primary tumor, two processes that are initiated by chemotactic cues in specific tumor microenvironments. The present laboratory has data showing that such invasion gene profiles are partly transient; some of the mRNA changes seen during in vivo invasion are reversed after the cells are in the process of circulating in the bloodstream or after they have established metastatic growth in distant sites (S. Goswami, unpublished results). This agrees with the hypothesis of different gene programs being crucial for each step of the metastatic cascade. A recent intravital imaging report further supports this hypothesis: by using rat MTLn3 breast tumor cell xenografts in mice, Giamperi et al. have shown upregulation of TGFβ signaling upon migration of tumor cells towards blood vessels in the primary tumor (similar to the enrichment of TGFβ signaling reported here for the migratory human breast tumor cells), but subsequent downregulation of the same pathway for successful establishment of lung metastasis (33).

Interestingly, the unsupervised bioinformatics analysis implicates embryonic gene profiles being enriched in the human invasion signature, suggesting that human breast tumor cells recapitulate processes and reuse pathways of embryonic and tissue development during cancer invasion and dissemination. This hypothesis is consistent with the recent finding that, in a xenograft model of patient-derived pleural effusion breast tumor cells, the migratory tumor cell population, collected using the methods described here, is enriched by >2-fold in CD44-expressing cells, a breast cancer stem cell marker (46).

Example 2

Inhibition of specific genes from the human invasion signature abrogates invasion and hematogenous dissemination in breast tumors in vivo. Next the requirement of specific genes from the HIS was tested for invasion and dissemination of breast tumor cells in vivo. To more effectively model a potential clinical approach, and to avoid experimental artifacts resulting from adaptation to shRNAs in primary cells (patient-derived tumors were passaged only in mice as whole tissue chunks and never cultured), the effect of acute injection of specific pharmacological inhibitors or neutralizing antibodies into mice was evaluated with established tumors. The central regulator TGFβ pathway was focused on, as well as the top upregulated genes of the HIS. Specifically, IL8 and PTPN11 were targeted, as they were the two most upregulated genes by real-time PCR validation (FIG. 11), with a 56-fold and 80-fold mRNA expression increase in the migratory tumor cells respectively. IL8 (or CXCL8) was originally cloned as a factor attracting and activating neutrophils, which in turn promote angiogenesis and growth in tumors. IL8 stimulation has been shown to promote in vitro migration through matrigel in tumor cells lines, but its role in tumor cell migration and invasion in vivo has not been tested yet. PTPN11 (which encodes for the phosphatase Shp2) was first found as a gene of which germline mutations are linked to the developmental disorder syndromes Noonan and LEOPARD, but somatic mutations have also been associated with several types of malignancies. In relation to the mammary gland, deletion of PTPN11 in transgenic mice leads to impaired mammary gland development, its upregulation has been noted in infiltrating ductal carcinomas and its activity has been implicated in integrin signaling during in vitro migration through matrigel. However its role in invasion and dissemination of breast tumors in vivo has not been previously tested.

The inhibitors SB431542 (a small molecule specific inhibitor of the TGFβ receptor), NSC87877 (a small molecule specific inhibitor of PTPN11) were used, and a neutralizing antibody specific to human IL8 for the experiments. Because the focus of the study is migration and invasion, a drug treatment of only 4 hours was given to the mice before experimental assays so that an acute effect on migration can be measured without long-term effects on tumor growth. Invasion was measured by count of the total cells that chemotax and invade in the primary tumor towards a gradient source (EGF or FBS) with the in viva invasion assay. Intravasation and hematogenous dissemination was measured by count of the circulating tumor cells (CTCs) in the blood of tumor-bearing mice. When the inhibitors or neutralizing antibody were injected in the tumor-bearing mice, in vivo invasion and intravasation (i.e. number of CTCs) were significantly inhibited in MDA-MB-231 and HT17 and HT39 patient-derived tumors (FIG. 10). No significant difference in overall cell death was observed by histology in the treated tumors with the four-hour acute treatments. These data support that the genes identified by the HIS are potentially important mediators of breast cancer invasion and dissemination. As a negative control, an inhibitor to a gene was used that was not identified by the HIS, namely, MYC, a known oncogene recently identified as a master regulator of expression in "poor-outcome" cancer signatures. As hypothesized, acute treatment with 10058-F4, a small molecule inhibitor of Myc-Max interaction, did not significantly alter either in vivo invasion or intravasation in the human breast tumors (FIG. 10). BrdU incorporation (a proliferation marker) was significantly reduced in these same tumors, indicating that the inhibitor was indeed functional in vivo (FIG. 13). Most of the published signatures to date are isolated from whole patient samples, and therefore represent "whole-picture" information about the metastatic process, a summary of invasion, dissemination, and growth/proliferation. MYC is a central oncogene that is required for carcinogenesis, as well as growth of metastatic lesions after the tumor cells have reached the target organ, and therefore it is not surprising that it is a central regulator of earlier published signatures. The results show that MYC is not required for the isolated processes of invasion and intravasation, further suggesting that the HIS is a gene signature specific to the early metastatic steps of migration and invasion inside the primary tumor.

Methods & Materials

Cell culture. MDA-MB-231-GFP cells were cultured in DMEM (Invitrogen, Carlsbad, Calif.) with 10% fetal bovine serum (FBS) (cell line generated by stable transfection of plasmid expressing Green Fluorescent Protein (GFP) in parental ATCC line as described in (14).

Animal Models. All procedures were conducted in accordance with the National Institutes of Health regulations, and approved by the Albert Einstein College of Medicine animal use committee. For the MDA-MB-231 xenografts, a total of $2\times10^6$ MDA-MB-231-GFP cells per animal were resuspended in sterile PBS with 20% collagen I (BD Biosciences, Franklin Lakes, N.J.) and injected into the lower left mammary fat pad of severe combined immunodeficiency mice (SCID) (NCI, Frederick, Md.). All experiments were performed on tumors that were 1-1.2 cm in diameter. For the patient-derived tumors: All human tumor tissue was received as discard tissue under institutional IRB approval and without any patient identification. Tumor tissue was assigned a random number ID when received at the laboratory and implanted in mice within 2-3 hours from the operating room. The tissue was rinsed with sterile Hank's Balanced Salt Solution (HBSS, Invitrogen, Carlsbad, Calif.) cut in pieces of 2-3 mm and coated in matrigel (BD Biosciences, Franklin Lakes, N.J.). Two pieces of tumor were implanted surgically in both left and right lower mammary fat pads of SCID mice. The mice were supplemented with estrogen pellets (1.7 mg/pellet, 90-day release, Innovative Research of America, Sarasota, Fla.), unless the tumor was already known to be ER-negative. The mice were monitored for growth for up to 9 months, at which time if a tumor was not visible they were euthanized. For the tumors that grew, in vivo invasion was measured, and then the tumor was used to passage to new mice (surgical procedure same as before). Part of the tumor and the lungs of the mice were fixed for histology analysis. Staining for human cytokeratins was performed with the CAM5.2 anti-cytokeratin antibody (BD Biosciences) as per the company's instructions. For the blocking treatments of FIG. 5, mice were injected intraperitoneally four hours prior to the experiments with 100 mg/kg of SB431542 (Tocris, Ellisville, Mo.), or anti-IL8 antibody (MAB208, R&D Systems, Minneapolis, Minn.), or NSC87877 (Tocris, Ellisville, Mo.). Controls were same quantities of DMSO (Sigma) for the SB431542 experiment, of isotype control IgG (BD Biosciences) for the anti-IL8 experiment, and of water for the NSC87877 experiment.

In viva invasion assay. Cell collection into needles placed into live anesthetized animals was carried out as described previously (13). Migratory cells only enter the needles by active migration toward the chemotactic gradient. Cells are not passively collected in this assay and the cells collected are not a biopsy sample, because a block is used to prevent passive collection of cells and tissue during insertion of the needle into the primary tumor. Cell migration and chemotaxis have been demonstrated to be required for cell collection (15). Since the needles have matrigel and a chemotactic gradient, this assay is similar to a conventional matrigel invasion assay in that it measures the migration of tumor cells through a matrix and towards a chemotactic stimulus. However, because the cell migration happens from within the live primary tumor, this assay is truly in viva, it is subject to the tumor microenvironment, and better (16) recapitulates the properties of the primary tumor. After 4 hours of collection, the needles are removed and the total number of cells collected is determined by 4',6-diamidino-2-phenylindole (DAPI) staining.

The chemoattractants used in this study include human recombinant EGF (Invitrogen) at final concentration 25 nM, as well as 10% FBS serving as a general chemoattractant source. The effects of cell collection on gene expression were controlled for as described in FIG. 6.

Intravasation assay. The number of circulating tumor cells was measured in mice bearing a tumor of 1-1.2 cm, as previously described (48). Briefly, blood was drawn from the right heart ventricle of anesthetized mice and whole blood was plated in DMEM/20% FBS. Tumor cells were counted after one week. Cells counted from MDA-MB-23'-GFP xenograft mice were GFP positive confirming their identity as tumor cells. As a control, blood from non-tumor bearing mice was plated as well and absence of epithelial tumor cells was confirmed.

RNA extraction, amplification, probe labeling, and microarray hybridization. RNA extraction, reverse transcription, SMART PCR amplification, microarray probe labeling, hybridization, and image collection were performed exactly as described in previous studies (44, 45, 49). Six biological repeats were used for the invasive tumor cells and the average primary tumor cells respectively. Every sample was hybridized in one chip together with a common reference (human reference RNA from Clontech, amplified in the same conditions as the experimental sample). Custom printed 27K Human cDNA microarray chips were used for the sample and reference hybridization (microarray1k.aecom.yu.edu/). The primer sequences for RT-PCR validation in FIG. 2 are set forth in Table 9.

TABLE 9

Primer sequences for RT-PCR validation in FIG. 2.
(SEQ ID NO:s 1-48, respectively, left to right
then top to bottom)

| GENE | LEFT PRIMER | RIGHT PRIMER |
| --- | --- | --- |
| ARHGDIB | ctcggcctgaggagtatgag | gtggtcttgcttgtcatcgt |
| CAV1 | cgtctgtgacccactctttg | gatgcggacattgctgaata |
| CDC25A | cccaaactccactaccctga | gcggaacttcttcaggtctt |
| CDC42 | tacgaccgctgagttatcca | atctcaggcacccacttttc |

TABLE 9-continued

Primer sequences for RT-PCR validation in FIG. 2.
(SEQ ID NO:s 1-48, respectively, left to right then top to bottom)

| GENE | LEFT PRIMER | RIGHT PRIMER |
|---|---|---|
| DAZAP2 | tggtggaaggagggtatgat | aggaggtggaggaggaatgt |
| FADD | gacctccagaacaggagtgg | atgcgtctgagttccatgac |
| FOXM1 | tgatggatctcagcaccact | gggacggagatgaggtctaa |
| IFI16 | catggacgactgaccacaat | cctggtcttgatgaccttga |
| IL8 | ctgcgccaacacagaaatta | acttctccacaaccctctgc |
| KLF11 | gccggaagacctacttcaaa | gctgcagttgaaaggcttct |
| MSN | aaggagagtgaggctgtgga | gctctgccacatgaggtgta |
| NCL | ttcaacagtgaggaggatgc | agccaccttcacccttaggt |
| PHACTR2 | agaggcccacaactgaagaa | ggctgagctttctgctgagt |
| PKM2 | gggtgaactttgccatgaat | tgaccacatctcccttcttg |
| PTPN11 | atatggcgtcatgcgtgtta | tccgtattcccttgtccaac |
| SKP1 | accctcctcctcctgaagat | cttggtcccaaacagggata |
| SMAD2 | gtgcaatctttgtgcagagc | agcagcaaattcctggttgt |
| SNTB2 | ctgctgagctgatcaaggaa | cggtacaatatgctgctgga |
| TUBA1A | ccaagcgtaccatccagttt | agtgggaggctggtagttga |
| UBC | cgtgaagaccctgactggta | cttggatctttgccttgaca |
| VAMP7 | gctcgagccatgtgtatgaa | tccaccacagagaggtgaaa |
| XRCC5 | cctgaaagcccttcaagaga | agaggcttcctctttggtga |
| GAPDH | cgaccactttgtcaagctca | ccctgttgctgtagccaaat |
| B2M | gctcgcgctactctctcttt | ttcaatgtcggatggatgaa |

TABLE 10

Primer sequences for RT-PCR validation in FIG. 2.
(SEQ ID NO:s 49-114, respectively, left to right then top to bottom)

| GENE | Forward primer | Reverse primer |
|---|---|---|
| GAPDH | cgaccactttgtcaagctca | ccctgttgctgtagccaaat |
| B2M | gctcgcgctactctctcttt | ttcaatgtcggatggatgaa |
| ARHGDIB | ctcggcctgaggagtatgag | gtggtcttgcttgtcatcgt |
| CAPZA2 | tacgtcgacagttgccagtt | tctgcatctctttgccaatc |
| CAPZB | atatcgtcaatgggctgagg | ctcttcaaagcctccaccag |
| SNTB2 | ctgctgagctgatcaaggaa | cggtacaatatgctgctgga |
| PHACTR2 | agaggcccacaactgaagaa | ggctgagctttctgctgagt |
| TUBA1A | ccaagcgtaccatccagttt | agtgggaggctggtagttga |
| CAV1 | cgtctgtgacccactctttg | gatgcggacattgctgaata |
| CDC42 | tacgaccgctgagttatcca | atctcaggcacccactttc |
| IL8 | ctgcgccaacacagaaatta | acttctccacaaccctctgc |

TABLE 10-continued

Primer sequences for RT-PCR validation in FIG. 2.
(SEQ ID NO:s 49-114, respectively, left to right then top to bottom)

| GENE | Forward primer | Reverse primer |
|---|---|---|
| LSM3 | gacgacgtagaccagcaaca | cgaagctctcggtcatttct |
| MSN | aaggagagtgaggctgtgga | gctctgccacatgaggtgta |
| PTPN11 | atatggcgtcatgcgtgtta | tccgtattcccttgtccaac |
| SMAD2 | gtgcaatctttgtgcagagc | agcagcaaattcctggttgt |
| SNTB2 | ctgctgagctgatcaaggaa | cggtacaatatgctgctgga |
| FADD | gacctccagaacaggagtgg | atgcgtctgagttccatgac |
| KLF11 | gccggaagacctacttcaaa | gctgcagttgaaaggcttct |
| VAMP7 | gctcgagccatgtgtatgaa | tccaccacagagaggtgaaa |
| YWHAE | gcagaactggatacgctgag | cctgcatgtctgaagtccat |
| DAZAP2 | tggtggaaggagggtatgat | aggaggtggaggaggaatgt |
| FOXM1 | tgatggatctcagcaccact | gggacggagatgaggtctaa |
| CDC25A | cccaaactccactaccctga | gcggaacttcttcaggtctt |
| CKS1B | atagccaagctggtccctaa | tgtgaggttctggttcatgg |
| IFI16 | catggacgactgaccacaat | cctggtcttgatgaccttga |
| NCL | ttcaacagtgaggaggatgc | agccaccttcacccttaggt |
| NPM1 | ggtggttctcttcccaaagt | agcctcttggtcagtcatcc |
| POLR2G | tgattcagcaggacgatgag | tcagcttacaagcccaagt |
| S100A11 | tgccttcacaaagaaccaga | ccttgaggaaggagtcatgg |
| SKP1 | accctcctcctcctgaagat | cttggtcccaaacagggata |
| TRIM32 | tcgccagattagccacttct | tggagaatttccttgcgact |
| UBC | cgtgaagaccctgactggta | cttggatctttgccttgaca |
| XRCC5 | cctgaaagcccttcaagaga | agaggcttcctctttggtga |

Quality control and significance analysis of microarrays. The scanned images were analyzed using the software Genepix (Axon Instruments, Foster City, Calif.), and an absolute intensity value was obtained for both the channels. Data filtering and global LOWESS normalization were done as described previously (44,45). Statistical analysis was performed by significance analysis of microarrays (SAM) (50). A total of 443 significantly regulated transcripts were identified by SAM at a false discovery rate (FDR) of 5% when comparing migratory tumor cells to average primary tumor cells. Out of these transcripts, 185 encode for known protein products.

IPA and GSEA analysis of the human invasion signature. The full 443-gene list (185 annotated genes and ESTs of unknown gene product or function) that resulted from the SAM analysis of the microarrays was used for the IPA and GSEA analysis. The Ingenuity Pathways Knowledge Base (IPA) version 8.7 was used to identify enriched physiological and cellular functions and canonical pathways among differentially regulated transcripts of the human invasion signature (www.ingenuity.com/products/pathways_analysis.html). p values were calculated through IPA using a right-tailed Fisher's exact test. A cutoff of p<0.05 was used for significance, as suggested by the software. Gene set enrichment analysis (GSEA) (51,52) was used to identify KEGG pathways upregulated in the human invasion signature. The KEGG pathways gene set was downloaded from the GSEA Molecular Signatures Database (www.broadinstitute.org/gsea/msigdb). Statistical significance (17) was assessed using 1,000 gene set permutations. A cutoff of FDR<25% was used for significance, as suggested by the GSEA team in the GSEA website.

Real-time PCR confirmation. Quantitative PCR analysis was performed as described previously (14), using the Power SYBR Green PCR Core Reagents system (Applied Biosystems). The cDNA used as input for the PCR reactions was amplified with the same protocol as described above for with the microarrays (but from independent biological repeats). Each PCR reaction was performed in triplicate, and the mean threshold cycle (CT) values were used for analysis. All the genes tested were compared with two housekeeping genes (β-2 microglobulin and GAPDH) for the analysis. Results were evaluated with the ABI Prism SDS 2.1 software.

Biostatistics analysis of the human invasion signature. For the UNC cohort, patient gene expression and clinical data published in (18) were downloaded from genome.unc.edu. For the NKI cohort, patient gene expression and clinical data published in (53) were downloaded from microarray-pubs.stanford.edu/wound_NKI/explore. In both datasets, if multiple array probe sets referred to the same gene, the probe set with the greatest variation was selected to represent the gene. Clinical data associated with these cohorts are reported as recurrence free survival for the UNC group and as metastasis-free survival for the NKI group. The top 75-80 regulated genes in the human invasion signature were used for the analysis, trying to keep the gene lists as identical as possible for both UNC and NKI cohorts considering that spots corresponding to some of the genes could not always be found on the original patient microarrays. The analysis was also performed for the whole 185-signature gene list (FIG. 7). The method from Minn et al. was used (10) to investigate the relationship between the human invasion signature and recurrence-free or metastasis-free survival in UNC and NKI cohorts. A training testing method known as leave-one-out cross-validation was used to generate a risk index for each case. This risk index was defined as a linear combination of gene expression values weighted by their estimated univariate Cox model regression coefficients. In each round, the gene expression profile for each of gene belonging to the invasion signature was used to fit the univariate Cox proportional hazards regression model in all cases minus one (training sample). The coefficients of these models were used to calculate the risk index later on the single test case that had been removed earlier. If a risk index was in the top 20th percentile of the risk index scores of training sample, then it was assigned to a high-risk group. Otherwise, it was assigned to a low-risk group. Repeating this procedure as many independent times as the number of patient cases, the risk index value was determined for each case. All cases were assigned to a high- or low-risk group. Kaplan-Meier survival plots and log-rank tests were then used to assess whether the risk index assignment was validated. In the UNC database, to estimate the similarity of each subject's gene expression pattern to the human invasion signature, an R-value was calculated for each subject in relation to the human invasion signature following the method of Creighton et al. (19). The R value was defined as the Pearson's correlation between the human invasion signature pattern (using "1" and "−1" for up and down regulation respectively) and the primary tumor's expression values, resulting in high R values for the tumors which tend to have both high expression of the upregulated genes and low expression of the downregulated genes in the human invasion signature. Before computing the R-value, the gene (18) expression values were centered on the centroid mean of the comparison groups of interest. The R value for each patient was then calculated, plotted and grouped by breast cancer subtype.

Statistical Analysis of mouse experimental methods. Results shown are representative of at least four different mice per point for the in vivo experiments. All statistical analyses, unless otherwise stated, were assessed using unpaired, two-tailed Student's t test assuming equal variances. Differences were considered significant if the p value was <0.05. For the intravasation assay, the Mann Whitney Wilcoxon rank sum test was used in addition to the Student's t test.

REFERENCES

1. Perou, C. M., et al. Molecular portraits of human breast tumours. *Nature* 406, 747-752 (2000).
2. Sorlie, T., et al. Gene expression patterns of breast carcinomas distinguish tumor subclasses with clinical implications. *Proc. Natl. Acad. Sci. U.S.A.* 98, 10869-10874 (2001).
3. van de Vijver, M. J., et al. A gene-expression signature as a predictor of survival in breast cancer. *N. Engl. J. Med.* 347, 1999-2009 (2002).
4. van't Veer, L. J., et al., Gene expression profiling predicts clinical outcome abreast cancer. *Nature* 415, 530-536 (2002).
5. Sorlie, T., et al. Repeated observation of breast tumor subtypes in independent gene expression data sets. *Proc. Natl. Acad. Sci. U.S.A.* 100, 8418-8423 (2003).
6. Wang, Y., et al. Gene-expression profiles to predict distant metastasis of lymph-node-negative primary breast cancer. *Lancet* 365, 671-679 (2005).
7. Chang, H. Y., et al. Gene expression signature of fibroblast serum response predicts human cancer progression: similarities between tumors and wounds. *PLoS Biol* 2, E7 (2004).
8. Nguyen, D. X., Bos, P. D. & Massague, J. Metastasis: from dissemination to organ-specific colonization. *Nat Rev Cancer* 9, 274-284 (2009).
9. Kang, Y., et al. A multigenic program mediating breast cancer metastasis to bone. *Cancer Cell* 3, 537-549 (2003).
10. Minn, A. J., et al., Genes that mediate breast cancer metastasis to lung. *Nature* 436, 518-524 (2005).
11. Bos, P. D., et al. Genes that mediate breast cancer metastasis to the brain. *Nature* 459, 1005-1009 (2009).
12. Neve, R. M., et al. A collection of breast cancer cell lines for the study of functionally distinct cancer subtypes. *Cancer Cell* 10, 515-527 (2006).
13. Wyckoff, J. B., Segall, J. E. & Condeelis, J. S. The collection of the motile population of cells from a living tumor. *Cancer Res.* 60, 5401-5404 (2000).
14. Patsialou, A., et al. Invasion of human breast cancer cells in vivo requires both paracrine and autocrine loops involving the colony-stimulating factor-1 receptor. *Cancer Res.* 69, 9498-9506 (2009).
15. Wyckoff, J. et al. A paracrine loop between tumor cells and macrophages is required for tumor cell migration in mammary tumors. *Cancer Res.* 64, 7022-7029 (2004).
16. Ojalvo, L. S., Whittaker, C. A., Condeelis, J. S. & Pollard, J. W. Gene expression analysis of macrophages that facilitate tumor invasion supports a role for Wnt-signaling in mediating their activity in primary mammary tumors. *J. Immunol.* 184, 702-712 (2010).

17. Goswami, S., Wang, W., Wyckoff, J. B. & Condeelis, J. S. Breast cancer cells isolated by chemotaxis from primary tumors show increased survival and resistance to chemotherapy. *Cancer Res.* 64, 7664-7667 (2004).

18. Herschkowitz, J. I., et al. Identification of conserved gene expression features between murine mammary carcinoma models and human breast tumors. *Genome Biol* 8, R76 (2007).

19. Brenton, J. D., Carey, L. A., Ahmed, A. A. & Caldas, C. Molecular classification and molecular forecasting of breast cancer: ready for clinical application? *J. Clin. Oncol.* 23, 7350-7360 (2005).

20. Creighton, C. J., et al. Residual breast cancers after conventional therapy display mesenchymal as well as tumor-initiating features. *Proc. Natl. Acad. Sci. U.S.A.* 106, 13820-13825 (2009).

21. Moustakas, A. & Heldin, C. H. The regulation of TGFbeta signal transduction. *Development* 136, 3699-3714 (2009).

22. Sahai, E. & Marshall, C. J. RHO-GTPases and cancer. *Nat Rev Cancer* 2, 133-142 (2002).

23. Steffen, A., et al. MT1-MMP-dependent invasion is regulated by TI-VAMP/VAMP7. *Curr. Biol.* 18, 926-931 (2008).

24. Boutros, R., Lobjois, V. & Ducommun, B. CDC25 phosphatases in cancer cells: key players? Good targets? *Nat. Rev Cancer* 7, 495-507 (2007).

25. Matozaki, T., Murata, Y., Saito, Y., Okazawa, H. & Ohnishi, H. Protein tyrosine phosphatase SHP-2: a proto-oncogene product that promotes Ras activation. *Cancer Sci* 100, 1786-1793 (2009).

26. Waugh, D. J. & Wilson, C. The interleukin-8 pathway in cancer. *Clin. Cancer Res.* 14, 6735-6741 (2008).

27. Roche, D. D., Liu, K. J., Harland, R. M. & Monsoro-Burq, A. H. Dazap2 is required for FGF-mediated posterior neural patterning, independent of Wnt and Cdx function. *Dev. Biol.* 333, 26-36 (2009).

28. Asano, H., Li, X. S. & Stamatoyannopoulos, G. FKLF, a novel Kruppel-like factor that activates human embryonic and fetal beta-like globin genes. *Mol. Cell. Biol.* 19, 3571-3579 (1999).

29. Lanigan, F., O'Connor, D., Martin, F. & Gallagher, W. M. Molecular links between mammary gland development and breast cancer. *Cell. Mol. Life Sci.* 64, 3159-3184 (2007).

30. Padua, D. & Massague, J. Roles of TGFbeta in metastasis. *Cell Res.* 19, 89-102 (2009).

31. McCave, E. J., Cass, C. A., Burg, K. J. & Booth, B. W. The normal microenvironment directs mammary gland development. *J. Mammary Gland Biol. Neoplasia* 15, 291-299 (2010).

32. Shipitsin, M., et al. Molecular definition of breast tumor heterogeneity. *Cancer Cell* 11, 259-273 (2007).

33. Giampieri, S., et al. Localized and reversible TGFbeta signalling switches breast cancer cells from cohesive to single cell motility. *Nat Cell Biol* 11, 1287-1296 (2009).

34. Padua, D., et al. TGFbeta primes breast tumors for lung metastasis seeding through angiopoietin-like 4. *Cell* 133, 66-77 (2008).

35. Stover, D. G., Bierie, B. & Moses, H. L. A delicate balance: TGF-beta and the tumor microenvironment. *J. Cell. Biochem.* 101, 851-861 (2007).

36. Marangoni, E., et al. A new model of patient tumor-derived breast cancer xenografts for preclinical assays. *Clin. Cancer Res.* 13, 3989-3998 (2007).

37. Sakakibara, T., et al. Growth and metastasis of surgical specimens of human breast carcinomas in SCID mice. *Cancer J. Sci. Am.* 2, 291-300 (1996).

38. Halder, S. K., Beauchamp, R. D. & Datta, P. K. A specific inhibitor of TGF-beta receptor kinase, SB-431542, as a potent antitumor agent for human cancers. *Neoplasia* 7, 509-521 (2005).

39. Charafe-Jauffret, E., et al. Breast cancer cell lines contain functional cancer stem cells with metastatic capacity and a distinct molecular signature. *Cancer Res.* 69, 1302-1313 (2009).

40. Freund, A., et al. IL-8 expression and its possible relationship with estrogen-receptor-negative status of breast cancer cells. *Oncogene* 22, 256-265 (2003).

41. Grossmann, K. S., Rosario, M., Birchmeier, C. & Birchmeier, W. The tyrosine phosphatase Shp2 in development and cancer. *Adv. Cancer Res.* 106, 53-89 (2010).

42. Chan, G., Kalaitzidis, D. & Neel, B. G. The tyrosine phosphatase Shp2 (PTPN11) in cancer. *Cancer Metastasis Rev.* 27, 179-192 (2008).

43. Ke, Y., et al. Conditional deletion of Shp2 in the mammary gland leads to impaired lobulo-alveolar outgrowth and attenuated Stat5 activation. *J. Biol. Chem.* 281, 34374-34380 (2006).

44. Wang, W., et al. Identification and testing of a gene expression signature of invasive carcinoma cells within primary mammary tumors. *Cancer Res.* 64, 8585-8594 (2004).

45. Wang, W., et al. Coordinated regulation of pathways for enhanced cell motility and chemotaxis is conserved in rat and mouse mammary tumors. *Cancer Res.* 67, 3505-3511 (2007).

46. Liu, H., et al. Cancer stem cells from human breast tumors are involved in spontaneous metastases in orthotopic mouse models. *Proc. Natl. Acad. Sci. U.S.A.* 107, 18115-18120 (2010).

47. Ginestier, C., et al. CXCR1 blockade selectively targets human breast cancer stem cells in vitro and in xenografts. *J. Clin. Invest.* 120, 485-497 (2010).

48. Wyckoff, J. B., Jones, J. G., Condeelis, J. S. & Segall, J. E. A critical step in metastasis: in vivo analysis of intravasation at the primary tumor. *Cancer Res.* 60, 2504-2511 (2000).

49. Wang, W., et al. Gene expression analysis on small numbers of invasive cells collected by chemotaxis from primary mammary tumors of the mouse. *BMC Biotechnol* 3, 13 (2003).

50. Tusher, V. G., Tibshirani, R. & Chu, G. Significance analysis of microarrays applied to the ionizing radiation response. *Proc. Natl. Acad. Sci. U.S.A.* 98, 5116-5121 (2001).

51. Subramanian, A., et al. Gene set enrichment analysis: a knowledge-based approach for interpreting genome-wide expression profiles. *Proc. Natl. Acad. Sci. U.S.A.* 102, 15545-15550 (2005).

52. Mootha, V. K., et al. PGC-1 alpha-responsive genes involved in oxidative phosphorylation are coordinately downregulated in human diabetes. *Nat. Genet.* 34, 267-273 (2003).

53. Chang, H. Y., et al. Robustness, scalability, and integration of a wound-response gene expression signature in predicting breast cancer survival. *Proc. Natl. Acad. Sci. U.S.A.* 102, 3738-3743 (2005).

What is claimed is:

1. A method of treating a cancer in a subject comprising: identifying the subject to be (i) at risk of metastasis of a tumor of the cancer or (ii) at risk of invasion of a tumor, or (iii) at risk of recurrence of a tumor of the cancer after treatment of the tumor, wherein the subject is determined to be at risk by a method comprising:

(I) A) obtaining a sample of the tumor and determining the level of expression in the sample of the following genes (1) CSDE1, PGK1, FAU, DAZAP2, NPM1, SUMO1, ARHGDIB, TBCA, WBP5, MSN, S100A11, PTPN11, PRDX3, IMPDH2, RPL19, BTG1, SNTB2, NOP10, RPL37, UBC, RPS6, SET, STXBP2, ANXA5, NONO, STRBP, PSME2, YWHAE, SNRPD1, DUSP16, UCRC, ALDOA, XRCC5, PMAIP1, IFI16, DGUOK, TUBA3D, DCBLD2, PHACTR2, COX7B, MRPL27, SF3B2, IL8, ERH, LSM3, ATP5I, RPL12, MYL12A, CDC25A, GLO1, TUBA4A, GARS, RPL30, ATP5G1, PKM2, PSMB2, RPL11, SF3B14, EMP1, OSGEP, SPHK2, RPS24, DDAH1, ILF2, CDC42, SNRPD3, SDHD, FOXM1, RABIF, CALU, NCL, ITGAE, CAV1, PRDX5, and DNAJC8, and determining the level of expression of each and every one of the genes in (1) as upregulated relative to a predetermined control, so as to identify the subject having the tumor as being (i) at risk of metastasis of the tumor, (ii) at risk of invasion of the tumor, or (iii) at risk of recurrence of the tumor after treatment of the tumor, or B) obtaining a sample of the tumor and determining the level of expression in the sample of all of the following genes (2) GLUD1, LIMS1, MDM2, MLL4, and DPP9, and determining the level of expression of each and every one of the genes in (2) as downregulated relative to a predetermined control, so as to identify the subject having the tumor as being (i) at risk of metastasis of the tumor, (ii) at risk of invasion of the tumor, or (iii) at risk of recurrence of the tumor after treatment of the tumor, and (II) administering to the subject who has been identified as being at risk of metastasis, invasion or recurrence an anti-PTPN11 therapy, anti-IL8 therapy, anti-MYC therapy or anti-TGFB therapy so as to thereby treat the cancer in the subject.

2. The method of claim 1, wherein the cancer is a breast cancer.

3. The method of claim 1, wherein the subject is a human.

4. The method of claim 1, wherein determining the level of expression of the genes is effected by quantifying a) the level of mRNA transcripts of the genes or b) the level of unique fragments of mRNA transcripts of the genes in the sample.

5. The method of claim 4, wherein quantifying the level of mRNA transcripts of the genes comprises performing a quantitative polymerase chain reaction.

6. The method of claim 4, wherein the sample is obtained by micro-needle biopsy.

* * * * *